United States Patent
Takenaka et al.

(10) Patent No.: US 9,278,108 B2
(45) Date of Patent: Mar. 8, 2016

(54) HMGB1 BINDING NUCLEIC ACID MOLECULE AND APPLICATIONS THEREOF

(75) Inventors: Hiromi Takenaka, Tokyo (JP); Jou Akitomi, Tokyo (JP); Shintarou Katou, Tokyo (JP); Shotaro Tsuji, Yokohama (JP); Takashi Ohtsu, Yokohama (JP); Iwao Waga, Tokyo (JP)

(73) Assignees: NEC Solution Innovators, Ltd., Tokyo (JP); Kanagawa Prefectural Hospital Organization, Yokohama-shi, Kanagawa (JP)

( * ) Notice: Subject to any disclaimer, the term of this patent is extended or adjusted under 35 U.S.C. 154(b) by 774 days.

(21) Appl. No.: 13/383,826

(22) PCT Filed: Jul. 16, 2010

(86) PCT No.: PCT/JP2010/062104
§ 371 (c)(1),
(2), (4) Date: Apr. 27, 2012

(87) PCT Pub. No.: WO2011/007876
PCT Pub. Date: Jan. 20, 2011

(65) Prior Publication Data
US 2012/0208867 A1 Aug. 16, 2012

(30) Foreign Application Priority Data
Jul. 16, 2009 (JP) .................... 2009-167622

(51) Int. Cl.
| C12N 15/115 | (2010.01) |
| A61K 31/7088 | (2006.01) |
| A61K 31/7105 | (2006.01) |
| C07K 14/47 | (2006.01) |
| G01N 33/68 | (2006.01) |

(52) U.S. Cl.
CPC ......... *A61K 31/7088* (2013.01); *A61K 31/7105* (2013.01); *C07K 14/4703* (2013.01); *C12N 15/115* (2013.01); *G01N 33/6863* (2013.01); *C12N 2310/16* (2013.01)

(58) Field of Classification Search
None
See application file for complete search history.

(56) References Cited

U.S. PATENT DOCUMENTS

| 2004/0136979 A1 | 7/2004 | Bianchi et al. |
| 2005/0152903 A1 | 7/2005 | Newman et al. |
| 2006/0099207 A1 | 5/2006 | Wu et al. |
| 2008/0113385 A1 | 5/2008 | Newman et al. |
| 2008/0171052 A1 | 7/2008 | Bianchi et al. |
| 2008/0311122 A1 | 12/2008 | Wu et al. |
| 2009/0148453 A1 | 6/2009 | Newman et al. |
| 2009/0169546 A1 | 7/2009 | Wu et al. |
| 2009/0252739 A1 | 10/2009 | Nishibori et al. |
| 2010/0061987 A1 | 3/2010 | Wu et al. |
| 2010/0172896 A1 | 7/2010 | Bianchi et al. |
| 2010/0172909 A1 | 7/2010 | Nishibori et al. |
| 2010/0297107 A1 | 11/2010 | Bianchi et al. |
| 2011/0217292 A1 | 9/2011 | Newman et al. |
| 2011/0287023 A1 | 11/2011 | Wu et al. |

FOREIGN PATENT DOCUMENTS

| CN | 1537014 A | 10/2004 |
| CN | 1878793 A | 12/2006 |
| CN | 101132811 A | 2/2008 |
| JP | 3876325 B1 | 1/2007 |
| JP | 2008-520552 A | 6/2008 |
| WO | WO 02/074337 A1 | 9/2002 |
| WO | WO 2005/026209 A2 | 3/2005 |
| WO | WO 2007/001422 A2 | 1/2007 |
| WO | WO 2007/076200 A2 | 7/2007 |
| WO | WO 2007/084253 A2 | 7/2007 |

OTHER PUBLICATIONS

Gaillard et al. A high-sensitivity method for detection and measurement of HMGB1 protein concentration by high-affinity binding to DNA hemicatenanes. PLoS ONE, vol. 3, No. 8, p. e2855, Aug. 2008, printed as pp. 1/9-9/9.*
Paborsky et al. The single-stranded DNA aptamer-binding site of human thrombin. The Journal of Biological Chemistry, vol. 268, No. 28, ages 20808-20811, 1993.*
Stros, M. HMGB proteins: Interactions with DNA and chromatin. Biochimica et Biophysica Acta, vol. 1799, pp. 101-113, Jan.-Feb. 2010.*
Youn et al. Identification of lipopolysaccharide-binding peptide regions within HMGB1 and their effects on subclinical endotoxemia in a mouse model. European Journal of Immunology, vol. 41, pp. 2753-2762, 2011.*
Bunka et al. Development of aptamer therapeutics. Current Opinion in Pharmacology, vol. 10, No. 5, pp. 557-562, Jul. 17, 2010.*
Grove et al. Localized DNA flexibility contributes to target site selection by DNA-bending proteins. Journal of Molecular Biology, vol. 260, No. 2, pp. 120-125, Jul. 1996.*
NCBI Gene ID: 3146 (HMGB1 high mobility group box 1 [*Homo sapiens* (human)], printed from http://www.ncbi.nlm.nih.gov/gene/3146?report=full_report&format=text on Feb. 4, 2015 as pp. 1/7-7/7.*
Hamaguchi, et al.; "Aptamer Beacons for the Direct Detection of Proteins", Analytical Biochemistry, 2001, vol. 294, pp. 126-131.
Cui et al., "Specific Recognition of AT-Rich DNA Sequences by the Mammalian High Mobility Group Protein AT-hook 2: A SELEX Study", Biochemistry, vol. 46, No. 45, 2007, pp. 13059-13066.

(Continued)

*Primary Examiner* — Jennifer Dunston
(74) *Attorney, Agent, or Firm* — McGinn IP Law Group, PLLC

(57) ABSTRACT

A nucleic acid molecule that can bind to HMGB1 protein and applications thereof are provided. A nucleic acid molecule having a dissociation constant for HMGB1 protein of $5 \times 10^{-7}$ or less can be used as the nucleic acid molecule that can bind to HMGB1 protein. The HMGB1 binding nucleic acid molecule can bind to HMGB1 protein that is known to be a cause of diseases such as cancer and inflammation, and it is therefore possible to obtain an effect to prevent and an effect to treat such diseases by allowing the HMGB1 binding nucleic acid molecule to bind to HMGB1 protein in a living body.

13 Claims, 11 Drawing Sheets

(56) References Cited

OTHER PUBLICATIONS

Calogero, et al., "The lack of chromosomal protein Hmg1 does not disrupt cell growth but causes lethal hypoglycaemia in newborn mice", Nature Genetics, Jul. 1999, vol. 22, No. 3. pp. 276-280.

Calogero et al., "The lack of chromosomal protein Hmg1 does not disrupt cell growth but causes lethal hypoglycaemia in newborn mice", Nat. Genet., 1999, vol. 22, No. 3, pp. 276-280 (Abstract).

Bustin, "Regulation of DNA-Dependent Activities by the Functional Motifs of the High-Mobility-Group Chromosomal Proteins", Mol. Cell Biol., 1999, vol. 19, No. 8. pp. 5237-5246.

Andersson et al., "HMGB1 as a DNA-binding cytokine", J. Leukoc. Biol., 2002, vol. 72, pp. 1084-1091.

Klune et al., "HMGB1: Endogenous Danger Signaling", Mol. Med., 2008, vol. 14, pp. 476-484.

Ellerman et al., "Masquerader: High Mobility Group Box-1 and Cancer", Clin. Cancer Res., 2007, vol. 13; No. 10, pp. 2836-2848.

Liu et al., "Anti-high mobility group box 1 monoclonal antibody ameliorates brain infarction induced by transient ischemia in rats", FASEB J., 2007, vol. 21, pp. 3904-3916.

Keefe et al., "SELEX with modified nucleotides", Curr, Opin. Chem. Biol., 2008, vol. 12, No. 4, pp. 448-456.

Ohtsu et al., "RNA aptamers against HMGB1—the possibility to inhibit the cancer cell proliferation", Proceedings of the 68th Annual Meeting of the Japanese Cancer Association, 2009, p. 494, p. 1247.

Jayasena, "Aptamers: An Emerging Class of Molecules That Rival Antibodies in Diagnostics", 1999, Clinical Chemistry vol. 45, No. 9, pp. 1628-1650.

Jaouen et al., "Determinants of Specific Binding of HMGB1 Protein to Hemicatenated DNA Loops", J. Mol. Biol. 2005, vol. 353, No. 4, pp. 822-837.

Webb et al., "Structural Requirements for Cooperative Binding of HMG1 to DNA Minicircles", J. Mol. Biol. 2001, vol. 309, No. 1, pp. 79-88.

* cited by examiner

R8c6_1: (-18.5kcal/mol)

R8c6_1-18: (-14.0kcal/mol)

HMGB1 BINDING NUCLEIC ACID MOLECULE AND APPLICATIONS THEREOF

The present application is the national stage entry under 35 U.S.C. 371 of PCT/JP2010/062104, filed Jul. 16, 2009, which claims priority based on Japanese Patent Application No. 2009-467622 filed on Jul. 16, 2009, the contents of which are incorporated herein in its entirety.

Incorporated by reference herein is the sequence listing including in the text file having a file name "SequenceListing.txt" which was created on Apr. 27, 2012 and has a size of 23 KB.

TECHNICAL FIELD

The present invention relates to a nucleic acid molecule that binds to HMGB1 protein and applications thereof.

BACKGROUND ART

High-mobility group box 1 protein, i.e., HMGB1 protein (hereinafter referred to as "HMGB1"), is a protein essential for survival (Non-Patent Literature 1), and HMGB1 functions in a cell nucleus as a protein that forms a chromatin structure required for initiation of transcription (Non-Patent Literature 2). When HMGB1 is leaked or secreted out of a cell, HMGB1 functions as a cytokine that facilitates an inflammatory reaction, a morphological change of a cell, and migration of a cell (Non-Patent Literature 3). In recent years, an analysis of extracellular functions of HMGB1 has advanced, and it has been revealed that when autoimmune diseases, sepsis, traumatic shock, ischemia, and ischemia reperfusion disorders occur, HMGB1 aggravates inflammatory reactions or induces apoptosis. Accordingly; it has been demonstrated that HMGB1 serves as a target substance and a diagnostic marker of the treatment of these diseases (Non-Patent Literature 4). Moreover, regarding cancers, it has been reported that HMGB1 is involved in proliferation and metastasis infiltration of breast cancer, colon cancer, melanoma, prostatic cancer, pancreatic cancer, lung cancer, and the like, and the level of HMGB1 expression is increased compared with that in normal tissue (Non-Patent Literature 5). Under this circumstance, it has been desired that a substance that can bind to HMGB1 and neutralize the function thereof in order to prevent and treat the aforementioned diseases. However, only a diagnostic method that uses a monoclonal anti-HMGB1 antibody and a cerebral infarction model treatment in laboratory animals have been shown to be effective so far (Patent Literature 1 and 2, Non-Patent Literature 6).

CITATION LIST

Patent Literature

Patent Literature 1: Japanese Patent No. 3876325
Patent Literature 2: JP 2008-520552A

Non-Patent Literature

Non-Patent Literature 1: Calogero, S. et al., Nat. Genet. (1999) 22, 276-280
Non-Patent Literature 2: Bustin, M., Mol. Cell. Biol. (1999) 19, 523-5246
Non-Patent Literature 3: Andersson, U. et al., J. Leukoc. Biol. (2002) 72, 1084-1091
Non-Patent Literature 4: Klune, J. R. et al., Mol. Med. (2008) 14, 476-484.

Non-Patent Literature 5: Ellerman, J. E. et al., Clin. Cancer Res. (2007) 13, 2836-2848.
Non-Patent Literature 6: Liu, K. et al., FASEB J. (2007) 21, 3904-16.

SUMMARY OF INVENTION

Technical Problem

An objective of the present invention is to provide a nucleic acid molecule that can bind to HMGB1 as a substance usable in, for example, elucidation of pathogenic mechanisms of diseases in which HMGB1 is involved and which HMGB1 causes, and in a diagnosis and a treatment of such diseases, and to provide applications thereof.

Solution to Problem

Accordingly, the present inventors have prepared an RNA by an in vitro selection method using commercially available purified HMGB1 as a target substance. The HMGB1 binding nucleic acid molecule of the present invention is a binding nucleic acid molecule that can bind to HMGB1 protein (hereinafter referred to as HMGB1), characterized by having a dissociation constant for HMGB1 of $5\times10^{-7}$ or less.

The composition of the present invention is a composition containing the HMGB1 binding nucleic acid molecule of the present invention.

The detection reagent of the present invention is an HMGB1 detection reagent for detecting the aforementioned HMGB1, containing the aforementioned HMGB1 binding nucleic acid molecule of the present invention.

Advantageous Effects of Invention

The HMGB1 binding nucleic acid molecule of the present invention can bind to HMGB1. Therefore, the HMGB1 binding nucleic acid molecule of the present invention, for example, binds to HMGB1 and inhibits the function thereof thus enabling prevention and treatment of diseases such as those mentioned above that are caused by HMGB1. Moreover, with the HMGB1 binding nucleic acid molecule of the present invention, for example, determining the presence or absence of binding to HMGB1 enables detection of HMGB1 and thus an early diagnosis of a disease. Moreover; for example, expression of the HMGB1 binding nucleic acid molecule of the present invention in a cultured cell enables an experiment for inhibiting gene transcription, and use of the HMGB1 binding nucleic acid molecule of the present invention enables an experiment for inhibiting binding between extracellular HMGB1 and a receptor thereof, and accordingly, the HMGB1 binding nucleic acid molecule of the present invention can be used in elucidation of the functions of HMGB1. Therefore, the HMGB1 binding nucleic acid molecule of the present invention is also useful as a novel research tool.

DESCRIPTION OF EMBODIMENTS

<HMGB1 Binding Nucleic Acid Molecule>

Figure 1:
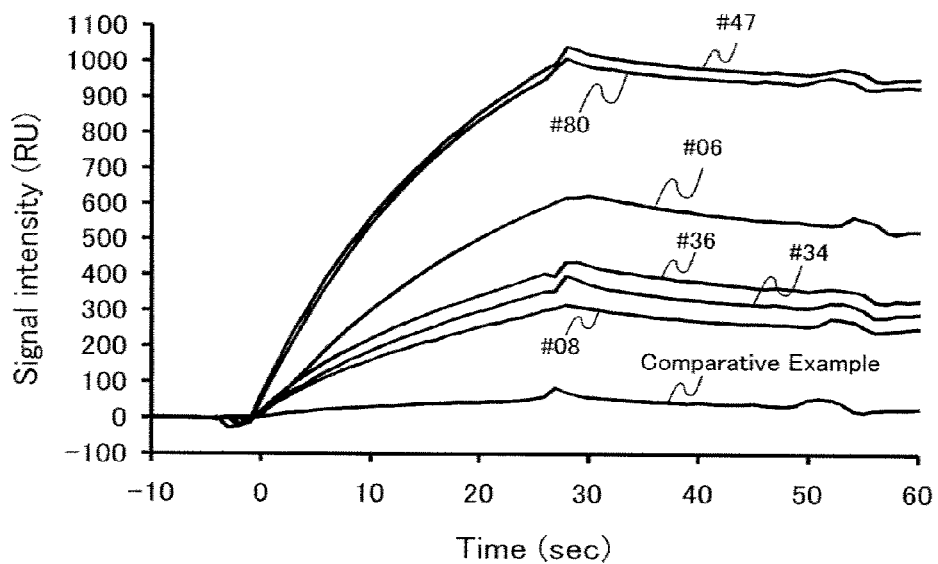
FIG. 1 is a graph showing the ability of each RNA aptamer to bind to His-tag-added HMGB1 in Example 1 of the present invention.

The HMGB1 binding nucleic acid molecule of the present invention is a nucleic acid molecule that can bind to HMGB1, characterized by having a dissociation constant for HMGB1 of $5 \times 10^{-7}$ or less. The HMGB1 binding nucleic acid molecule of the present invention is also referred to as, for example, an HMGB1 aptamer.

The phrase "can bind to HMGB1" as used herein may be paraphrased as having ability to bind to HMGB1 or having activity to bind to HMGB1 (HMGB1 binding activity). The HMGB1 binding nucleic acid molecule of the present invention, for example, binds specifically to HMGB1. The aforementioned binding between the HMGB1 binding nucleic acid molecule and HMGB1 can be determined by, for example, a surface plasmon resonance molecular interaction analysis or the like. For example, a BIACORE X (trade name, GE Healthcare UK Ltd.) can be used for the aforementioned analysis.

It is sufficient that the HMGB1 binding nucleic acid molecule of the present invention has a dissociation constant for HMGB1 of $5 \times 10^{-7}$ or less, and other configurations are not limited. The aforementioned dissociation constant for HMGB1 is not particularly limited, and the upper limit is, for example, on the order of $10^{-8}$, more preferably on the order of $10^{-10}$, and even more preferably on the order of $10^{-12}$. The range of the aforementioned dissociation constant is, for example, on the order of $10^{-14}$ to $10^{-8}$, preferably on the order of $10^{-14}$ to $10^{-10}$, and more preferably on the order of $10^{-14}$ to $10^{-12}$.

For example, the constitutional unit of the HMGB1 binding nucleic acid molecule of the present invention is not particularly limited. An example of the aforementioned constitutional unit may be a nucleotide residue, and examples of the aforementioned nucleotide residue include ribonucleotide residues and deoxyribonucleotide residues. The HMGB1 binding nucleic acid molecule of the present invention may be, for example, an RNA composed of a ribonucleotide residue or a DNA composed of a deoxyribonucleotide residue, with an RNA being preferable. The HMGB1 binding nucleic acid molecule of the present invention may contain, for example, both deoxyribonucleotide, which is a constitutional unit of a DNA, and ribonucleotide, which is a constitutional unit of an RNA. In this case, the HMGB1 binding nucleic acid molecule of the present invention may be, for example, an RNA containing a deoxyribonucleotide residue or may be an RNA containing a ribonucleotide residue.

The aforementioned nucleotide residue may be, for example, a modified nucleotide residue. In the aforementioned modified nucleotide residue, for example, the sugar moiety in the aforementioned nucleotide residue may be modified. Examples of the aforementioned sugar moiety include ribose residues and deoxyribose residues. The modification site in the aforementioned nucleotide residue is not particularly limited, and examples include the 2' position and/or the 4' position of the aforementioned sugar moiety. Examples of the aforementioned modification include methylation, fluorination, amination, thio-modification, and the like. Examples of the aforementioned modified nucleotide residue include modified nucleotide residues having a pyrimidine base (a pyrimidine nucleus) as a base and modified nucleotide residues having a purine base (a purine nucleus) as a base, with the former being preferable. Hereinafter, a nucleotide residue having a pyrimidine base is referred to as a pyrimidine nucleotide residue, a pyrimidine nucleotide residue that has been modified is referred to as a modified pyrimidine nucleotide residue, a nucleotide residue having a purine base is referred to as a purine nucleotide residue, and a purine nucleotide residue that has been modified is referred to as a modified purine nucleotide residue. Examples of the aforementioned pyrimidine nucleotide residue include a uracil nucleotide residue having uracil, a cytosine nucleotide residue having cytosine, a thymine nucleotide residue having thymine, and the like. Regarding the aforementioned modified nucleotide residue, in the case where the base is a pyrimidine base, it is preferable that, for example, the 2' position and/or the 4' position of the aforementioned sugar moiety are/is modified. Specific examples of the aforementioned modified nucleotide residue include 2'-methyluracil (a 2'-methylated-uracil nucleotide residue), 2'-methylcytosine (a 2'-methylated-cytosine nucleotide residue), 2'-fluorouracil (a 2'-fluorinated-uracil nucleotide residue), 2'-fluorocytosine (a 2'-fluorinated-cytosine nucleotide residue), 2'-aminouracil (a 2'-aminated uracil nucleotide residue), 2'-aminocytosine (a 2'-aminated-cytosine nucleotide residue), 2'-thiouracil (a 2'-thio-modified-uracil nucleotide residue), 2'-thiocytosine (a 2'-thio-modified-cytosine nucleotide residue), and the like in which the 2' position of a ribose residue is modified.

Regarding the HMGB1 binding nucleic acid molecule of the present invention, examples of the aforementioned constitutional unit include PNAs (peptide nucleic acids), LNAs (locked nucleic acids), ENAs (2'-O,4'-C-ethylenebridged nucleic acids), and like monomer residues. An example of the HMGB1 binding nucleic acid molecule of the present invention may be an RNA or a DNA that contains at least any of the monomer residues, i.e., PNAs, LNAs, and ENAs. In the case where the HMGB1 binding nucleic acid molecule of the present invention contains an aforementioned monomer residue, the number thereof is not particularly limited.

The HMGB1 binding nucleic acid molecule of the present invention may be, for example, a single-strand nucleic acid or may be a double-strand nucleic acid. Examples of the aforementioned single-strand nucleic acid include single-strand RNAs and single-strand DNAs. Examples of the aforementioned double-strand nucleic acid include double-strand RNAs, double-strand DNAs, and double-strand nucleic acids composed of an RNA and a DNA. In the case where the HMGB1 binding nucleic acid molecule of the present invention is a double-strand nucleic acid, for example, it may be processed into a single strand by denaturation or the like prior to use.

Regarding the HMGB1 binding nucleic acid molecule of the present invention, the bases may be, for example, naturally occurring bases (non-artificial bases), i.e., adenine (a), cytosine (c), guanine (g), thymine (t), and uracil (u), and may be artificial bases (non-naturally occurring bases). Examples of the aforementioned artificial bases include modified bases, altered bases, and the like, and it is preferable that the artificial bases function identically to the aforementioned naturally occurring bases (a, c, g, t, or u). Examples of the aforementioned identically functioning artificial bases include artificial bases that can bind to cytosine (c) instead of guanine (g), artificial bases that can bind to guanine (g) instead of cytosine (c), artificial bases that can bind to thymine (t) or uracil (u) instead of adenine (a), artificial bases that can bind to adenine (a) instead of thymine (t), artificial bases that can bind to adenine (a) instead of uracil (u), and the like. Examples of the aforementioned modified bases include methylated bases, fluorinated bases, aminated bases, thio-modified bases, and the like. Specific examples of the aforementioned modified bases include 2'-methyluracil, 2'-methylcytosine, 2'-fluorouracil, 2'-fluorocytosine, 2'-aminouracil, 2'-aminocytosine, 2-thiouracil, 2-thiocytosine, and the like. The bases represented by, for example, a, g, c, t, and u as used herein encompass, in addition to the aforementioned naturally occurring bases, the aforementioned artificial bases that function identically to the aforementioned respective naturally occurring bases.

It is preferable that the HMGB1 binding nucleic acid molecule of the present invention is, for example, resistant to a nuclease. The aforementioned nuclease is not particularly limited, and examples include exonucleases, endonucleases, and the like, and specific examples include ribonucleases (RNases), which are RNA-degrading enzymes, deoxyribonucleases (DNases), which are DNA-degrading enzymes, nucleases that act on both RNAs and DNAs, and the like. It is preferable that the HMGB1 binding nucleic acid molecule of the present invention is, as described above, an RNA. In the case where the HMGB1 binding nucleic acid molecule of the present invention is an RNA, it is preferable that the HMGB1 binding nucleic acid molecule is resistant to, for example, an RNA-degrading enzyme, i.e., an RNase. A technique for imparting the aforementioned nuclease resistance is not particularly limited, and an example may be a method that modifies nucleotide residues constituting the aforementioned nucleic acid molecule. Specifically, regarding the HMGB1 binding nucleic acid molecule of the present invention, it is preferable that, for example, nucleotide residues or some of the nucleotide residues constituting the aforementioned nucleic acid molecule are modified nucleotide residues. Examples of the aforementioned modified nucleotide residues include the modified nucleotide residues described above. Examples of the modified nucleotide residues include the aforementioned methylated nucleotide residues, the aforementioned fluorinated nucleotide residues, the aforementioned aminated nucleotide residues, the aforementioned thio-modified nucleotide residues, and the like, with the aforementioned fluorinated nucleotide residues being particularly preferable. Example of the aforementioned modified nucleotide residues may be the aforementioned pyrimidine nucleotide residues having a pyrimidine base as a base, and the aforementioned sugar residues (a ribose residue or a deoxyribose residue) are preferably modified.

In addition to the technique described above, another example of a technique for imparting the aforementioned nuclease resistance may be a method that processes nucleotide residues constituting the aforementioned nucleic acid molecule into LNAs. Specifically, regarding the HMGB1 binding nucleic acid molecule of the present invention, it is preferable that, for example, all nucleotide residues or some of the nucleotide residues constituting the aforementioned nucleic acid molecule are the aforementioned LNA residues. In addition to the technique described above, another example of a technique for imparting the aforementioned nuclease resistance may be a method that processes nucleotide residues constituting the aforementioned nucleic acid molecule, which is an RNA, into DNAs. Specifically, in the case where the HMGB1 binding nucleic acid molecule of the present invention is an RNA, for example, among all the nucleotide residues constituting the RNA, all or some of the nucleotide residues having uracil may be substituted with nucleotide residues having thymine, and specifically, may be substituted with the aforementioned deoxyribonucleotide residues having thymine. Also, in the case where the aforementioned nucleic acid molecule is an iRNA, all nucleotide residues or some of the nucleotide residues constituting the RNA may be deoxyribonucleotide residues and the aforementioned LNA residues.

In addition to the technique described above, another example of a technique for imparting the aforementioned nuclease resistance may be a method in which polyethylene glycol (PEG) or deoxythymidine is bound to the 5' end and/or 3' end. It is preferable that the aforementioned PEG has several tens of kDa.

The length of the HMGB1 binding nucleic acid molecule of the present invention is not particularly limited, and the overall length thereof is, for example, 20 to 160 bases long, preferably 30 to 120 bases long, and more preferably 40 to 100 bases long.

The HMGB1 binding nucleic acid molecule of the present invention is, for example, any of the nucleic acid molecules (A1), (A2), (B1) and (B2) below:

(A1) a nucleic acid molecule that contains a base sequence represented by any of SEQ ID NOs. 1 to 42, (A2) a nucleic acid molecule that contains a base sequence in which one or a plurality of bases are substituted, deleted, added, or inserted in regard to the base sequence represented by any of SEQ ID NOs. 1 to 42, and that can bind to HMGB1, (B1) a nucleic acid molecule that contains a base sequence represented by any of SEQ ID NOs. 45 to 81, and (B2) a nucleic acid molecule that contains a base sequence in which one or a plurality of bases are substituted, deleted, added, or inserted in regard to the base sequence represented by any of SEQ ID NOs. 45 to 81, and that can bind to HMGB1.

The aforementioned nucleic acid molecule (A1) will now be described. Hereinafter, the aforementioned nucleic acid molecule (A1) is referred to as an HMGB1 binding nucleic acid molecule (A1). Regarding the aforementioned HMGB1 binding nucleic acid molecule (A1), a base sequence represented by any of SEQ ID NOs. 1 to 42 is also referred to as a base sequence (A1). The aforementioned base sequence (A1) represented by any of SEQ ID NOs. 1 to 42 and the aforementioned HMGB1 binding nucleic acid molecule (A1) containing the base sequence (A1) may each be indicated by the nomenclature presented before a sequence ID number as shown below.

(A1) A Nucleic Acid Molecule that Contains a Base Sequence Represented by Any of SEQ ID NOs. 1 to 42

```
C_0
                                    (SEQ ID NO. 1)
mmhbuaagmcacguagmaccag C_1
                                    (SEQ ID NO. 2)
accguaagacacguagaaccag C_2
                                    (SEQ ID NO. 3)
aauuuaagccacguagaaccag C_3
                                    (SEQ ID NO. 4)
acaguaagacacguagcaccag C_4
                                    (SEQ ID NO. 5)
cauguaagccacguagaaccag

# 04
                                    (SEQ ID NO. 6)
ucccaugauuguucaggcacggccuuucgguucccucaau

# 08
                                    (SEQ ID NO. 7)
agucccuugacacguccguuucuaacuggaauagaggcc

# 12
                                    (SEQ ID NO. 8)
gggcugcaccucuccgcuacguugucguuggaggcaccau

# 43
                                    (SEQ ID NO. 9)
gguauuaaaacucccucguaggucauccgcccggccuagc

# 49
                                    (SEQ ID NO. 10)
cauccuuaucacauggucauccgcccggccaugcaauguu

# 32
                                    (SEQ ID NO. 11)
cauucuaaauucuaucaagggucauccgcccggcccgcau

# 58
                                    (SEQ ID NO. 12)
cauucuaaauucuaucaagggucauccgcccggccgcgcucgccaguca

# 01
                                    (SEQ ID NO. 13)
uggcauccuugcucacuccaggcuaaaccucucgguuccc

# 26
                                    (SEQ ID NO. 14)
ccaagcacuucaucgucuaggcaauugccucucgguaccc

# 73
                                    (SEQ ID NO. 15)
ccacaagcucgcacuaguuccaggcuuccucucgguaccc

# 77
                                    (SEQ ID NO. 16)
cauguauucugcacguuccagagaauccucucgguaccc

# 06
                                    (SEQ ID NO. 17)
uacacugcacgcuccgcuuugaacaucaauggaggcccug

# 22
                                    (SEQ ID NO. 18)
gcgcucgcucauagucaaggugaaaaccccauagagacu

# 10
                                    (SEQ ID NO. 19)
uagucaaggugaaaaccccauagagacu

# 21
                                    (SEQ ID NO. 20)
ggccugugcuaacaugagucauccguccggcucgcaacuc

# 36
                                    (SEQ ID NO. 21)
ccuagcacguccguuucuggaucugucaguuagaggccua

# 15
                                    (SEQ ID NO. 22)
gcaucaaccucuguaagagcgcgcuuugcuucaccaaaaa

# 23
                                    (SEQ ID NO. 23)
acguccuuaaaaucuuccuuaaccacgcccaggaucuua

# 34
                                    (SEQ ID NO. 24)
auucaccucagcauguccgcuugugacgauggaggcaccu

# 40
                                    (SEQ ID NO. 25)
gguccuuaaaaucuuccaaucuaaacgauccagacacggc

# 47
                                    (SEQ ID NO. 26)
aaaaacuacugccgaaccguaagacacguagaaccaggca

# 79
                                    (SEQ ID NO. 27)
gaccagguuccugacaucucugaacuauaccuccaaaacg

# 80
                                    (SEQ ID NO. 28)
caucugaauuuaagccacguagaaccaggcccuccacgcg

# 82
                                    (SEQ ID NO. 29)
uaauacgacucacuauagggacgcucacguacgcucagug R4_1
                                    (SEQ ID NO. 30)
aaugagggcccacuuccggaucuuugguuugcuuccuugc R4_4
                                    (SEQ ID NO. 31)
ucgcuuauggaugcccacuuccacucacuguccugcgcaa
```

-continued

R4_10
(SEQ ID NO. 32)
uauuaauaccucagcccucuucucuuagucuggugccgau

R4_11
(SEQ ID NO. 33)
ucucuuuucgaauuccguucuggcucacuccuugguauu

R4_12
(SEQ ID NO. 34)
cugacaucuuuuacacugauuucguuggcccacuucugu

R8c6_1
(SEQ ID NO. 35)
gaguacaguaagacacguagcaccagucugacguuugucg

R8c6_14
(SEQ ID NO. 36)
ugccaucaccauguaagccacguagaaccagcacuacuag

R8c9_1
(SEQ ID NO. 37)
ugagucuuauagccguccguuuacguuugucuagaggcca

R8c9_6
(SEQ ID NO. 38)
gcuucuugcauuguccgcuuaguuucuauggaggcauagu

R8c9_10
(SEQ ID NO. 39)
ccgaauauuuuugcaccguccgauugccaugcauugaggc

HMGB1R4_9068
(SEQ ID NO. 40)
ugauauuuaaauuuggccgcguuuaaaacaucccucacga

HMGB1R4_2478
(SEQ ID NO. 41)
gauuccguugcccuuccguugaacugugccaggcuuuuug

HMGB1R4_5108
(SEQ ID NO. 42)
accuuugccgcaucucacccacgucuugucaggccguuuc

In the aforementioned SEQ ID NO. 1, "m" is adenine or cytosine, "h" is adenine, cytosine, thymine, or uracil, and "b" is guanine, cytosine, thymine, or uracil. Examples of the base sequence represented by the aforementioned SEQ ID NO. 1 include the base sequences represented by SEQ ID NOs. 2 to 5 above. In the base sequences represented by the aforementioned SEQ ID NOs. 1 to 42 and SEQ ID NOs. 45 to 81, which will be presented below, uracil (u) may be thymine (t). In these base sequences, for example, one or two or more uracils may be thymines, or all uracils may be thymines. Accordingly, nucleic acid molecules composed of base sequences containing thymine or nucleic acid molecules containing the aforementioned base sequences can be regarded as examples of the nucleic acid molecule (A2), which will be described below.

The aforementioned HMGB1 binding nucleic acid molecule (A1) may be a nucleic acid molecule composed of the base sequence (A1) represented by any of SEQ ID NOs. 1 to 42, or may be a nucleic acid molecule containing the aforementioned base sequence (A1).

In the case where the aforementioned HMGB1 binding nucleic acid molecule (A1) contains the aforementioned base sequence (A1), for example, the HMGB1 binding nucleic acid molecule (A1) may further have a Y region and/or a Y' region, with the aforementioned base sequence (A1) being an X region. The aforementioned X region, the aforementioned Y region, and the aforementioned Y' region are, for example, as described below. The aforementioned Y region is not particularly limited, and examples include a sequence containing the base sequence represented by SEQ ID NO. 43 or 115, and a sequence composed of the aforementioned base sequence. Also, the aforementioned Y' region is not particularly limited, and examples include a sequence containing the base sequence represented by SEQ ID NO. 44 and a sequence composed of the aforementioned base sequence. Note that these sequences are examples and do not limit the present invention.

(SEQ ID NO. 43)
gggacgcucacguacgcuca (SEQ ID NO. 115)
acgcucacguacgcuca (SEQ ID NO. 44)
ucagugccuggacgugcagu In the case where the aforementioned HMGB1 binding nucleic acid molecule (A1) contains the aforementioned Y region, it is preferable that the aforementioned Y region is bound, for example, to the 5' side of the aforementioned base sequence (A1). In the case where the aforementioned HMGB1 binding nucleic acid molecule (A1) contains the aforementioned Y' region, it is preferable that the aforementioned Y region is bound, for example, to the 3' side of the aforementioned base sequence (A1). The aforementioned Y region and the aforementioned Y' region may be bound, for example, directly to the aforementioned base sequence (A1), or bound thereto via an intervening sequence.

In the case where the aforementioned HMGB1 binding nucleic acid molecule (A1) contains the aforementioned base sequence (A1) of any of SEQ ID NOs. 1 to 42, an example may be a nucleic acid molecule composed of a base sequence represented by any of SEQ ID NOs. 45 to 81 or a nucleic acid molecule containing the aforementioned base sequence. The base sequences of SEQ ID NOs. 45 to 81 shown below contain the aforementioned base sequences (A1) of SEQ ID NOs. 6 to 42, respectively and the respective underlined regions corresponds to the aforementioned base sequences of SEQ ID NOs. 6 to 42. The aforementioned base sequence of any of SEQ ID NOs. 45 to 81 and the aforementioned HMGB1 binding nucleic acid molecule (A1) containing the aforementioned base sequence may each be indicated by the nomenclature presented before a sequence ID number as shown below.

04
(SEQ ID NO. 45)
gggacgcucacguacgcuca<u>ucccaugauuguucaggcacggccuuucgg</u>

<u>uucccucaau</u>ucagugccuggacgugcagu

08
(SEQ ID NO. 46)
gggacgcucacguacgcuca<u>agucccuugacacguccguuuucuaacugg</u>

<u>aauagaggcc</u>ucagugccuggacgugcagu

12
(SEQ ID NO. 47)
gggacgcucacguacgcuca<u>gggcugcaccucuccgcuacguuugucguug</u>

<u>gaggccacau</u>ucagugccuggacgugcagu

43
(SEQ ID NO. 48)
gggacgcucacguacgcuca<u>gguauuaaaacucccucguaggucauccgc</u>

<u>ccggccuagc</u>ucagugccuggacgugcagu

49

(SEQ ID NO. 49)

gggacgcucacguacgcuca<u>cauccuuaucacauggucauccgcccggcc</u>

<u>augcaauguuu</u>cagugccuggacgugcagu

32

(SEQ ID NO. 50)

gggacgcucacguacgcuca<u>cauucuaaauucuaucaagggucauccgcc</u>

<u>cggcccgcau</u>ucagugccuggacgugcagu

58

(SEQ ID NO. 51)

gggacgcucacguacgcuca<u>cauucuaaauucuaucaagggucauccgcc</u>

<u>cggccgcgcucgccagucau</u>cagugccuggacgugcagu

01

(SEQ ID NO. 52)

gggacgcucacguacgcuca<u>uggcauccuugcucacuccaggcuaaaccu</u>

<u>ucggguuccc</u>ucagugccuggacgugcagu

26

(SEQ ID NO. 53)

gggacgcucacguacgcuca<u>ccaagcacuucaucgucuaggcaauugccu</u>

<u>cucgguaccc</u>ucagugccuggacgugcagu

73

(SEQ ID NO. 54)

gggacgcucacguacgcuca<u>ccacaagcucgcacuaguuccaggcuuccu</u>

<u>cucgguaccc</u>ucagugccuggacgugcagu

77

(SEQ ID NO. 55)

gggacgcucacguacgcuca<u>cauguauuucugcacguuccagagaauccu</u>

<u>cucgguaccc</u>ucagugccuggacgugcagu

06

(SEQ ID NO. 56)

gggacgcucacguacgcuca<u>uacacacugcacgcuccgcuuugaacaucaau</u>

<u>ggaggcccug</u>cagugccuggacgugcagu

22

(SEQ ID NO. 57)

gggacgcucacguacgcuca<u>gcgcucgcucauagucaaggugaaaacccc</u>

<u>cauagagacu</u>ucagugccuggacgugcagu

10

(SEQ ID NO. 58)

gggacgcucacguacgcuca<u>uagucaaggugaaaaccccccauagagacuu</u>cagugccuggacgugcagu

21

(SEQ ID NO. 59)

gggacgcucacguacgcuca<u>ggccugugcuaacaugagucauccguccgg</u>

<u>cucgcaacuc</u>ucagugccuggacgugcagu

36

(SEQ ID NO. 60)

gggacgcucacguacgcuca<u>ccuagcacguccguuucuggaucugucagu</u>

<u>uagaggccua</u>ucagugccuggacgugcagu

15

(SEQ ID NO. 61)

gggacgcucacguacgcuca<u>gcaucaaccucguaagagcgcgcuuugcu</u>

<u>ucaccaaaaau</u>cagugccuggacgugcagu

23

(SEQ ID NO. 62)

gggacgcucacguacgcuca<u>acggccuuaaaaaucuuccuuaaccacgcc</u>

<u>caggaucuua</u>ucagugccuggacgugcagu

34

(SEQ ID NO. 63)

gggacgcucacguacgcuca<u>auucaccucagcauguccgcuugugacgau</u>

<u>ggaggcaccu</u>ucagugccuggacgugcagu

40

(SEQ ID NO. 64)

gggacgcucacguacgcuca<u>gguccuuaaaaucuuccaaucuaaacgauc</u>

<u>cagacacggc</u>ucagugccuggacgugcagu

47

(SEQ ID NO. 65)

gggacgcucacguacgcuca<u>aaaaacuacugccgaaccguaagacacgua</u>

<u>gaaccaggca</u>ucagugccuggacgugcagu

79

(SEQ ID NO. 66)

gggacgcucacguacgcuca<u>gaccagguccugacaucucugaacuauac</u>

<u>cuccaaaacg</u>ucagugccuggacgugcagu

80

(SEQ ID NO. 67)

gggacgcucacguacgcuca<u>caucugaauuuaagccacguagaaccaggc</u>

<u>ccuccacgcg</u>ucagugccuggacgugcagu

82

(SEQ ID NO. 68)

gggacgcucacguacgcuca<u>uaauacgacucacuauagggacgcucacgu</u>

<u>acgc</u>ucagugccuggacgugcagu

R4_1

(SEQ ID NO. 69)

gggacgcucacguacgcuca<u>aaugagggcccacuuccggaucuuugguuu</u>

<u>gcuuccuugc</u>ucagugccuggacgugcagu

R4_4

(SEQ ID NO. 70)

gggacgcucacguacgcuca<u>ucgcuuauggaugcccacuuccacucacug</u>

<u>uccugcgcaa</u>ucagugccuggacgugcagu

R4_10

(SEQ ID NO. 71)

gggacgcucacguacgcuca<u>uauuaauaccucagcccucuucucuuaguc</u>

<u>uggugccgau</u>ucagugccuggacgugcagu

R4_11

(SEQ ID NO. 72)

gggacgcucacguacgcuca<u>ucucuuuucgaauuccguucuggcucacuc</u>

<u>cuuggguauu</u>ucagugccuggacgugcagu

R4_12

(SEQ ID NO. 73)

gggacgcucacguacgcuca<u>cugacaucuuuuacacugauuucuguuggc</u>

<u>ccacuucugu</u>ucagugccuggacgugcagu

R8c6_1

(SEQ ID NO. 74)

gggacgcucacguacgcuca<u>gaguacaguaagacacguagcaccagucug</u>

<u>acguuugucg</u>ucagugccuggacgugcagu

-continued

R8c6_14
(SEQ ID NO. 75)
gggacgcucacguacgcucaugccaucaccauguaagccacguagaacca gcacuacuagucagugccuggacgugcagu R8c9_1
(SEQ ID NO. 76)
gggacgcucacguacgcucaugagucuuauagccguccguuuacguuugu cuagaggccaucagugccuggacgugcagu R8c9_6
(SEQ ID NO. 77)
gggacgcucacguacgcucagcuucuugcauugcccgcuuaguuucuaug gaggcauagucagugccuggacgugcagu R8c9_10
(SEQ ID NO. 78)
gggacgcucacguacgcucaccgaauauuuugcaccguccgauugccau gcauugaggcucagugccuggacgugcagu HMGB1R4_9068
(SEQ ID NO. 79)
gggacgcucacguacgcucaugauauuuaaauuuggccgcguuuaaaaca uccccuacgaucagugccuggacgugcagu HMGB1R4_2478
(SEQ ID NO. 80)
gggacgcucacguacgcucagauuccguugcccuuccguugaacugugcc aggcuuuugucagugccuggacgugcagu HMGB1R4_5108
(SEQ ID NO. 81)
gggacgcucacguacgcucaaccuuugccgcaucucacccacgucuugc aggccguuucucagugccuggacgugcagu The aforementioned HMGB1 binding nucleic acid molecule (A1) may be, for example, a nucleic acid molecule composed of a base sequence from the 4th base on the 5' side to the terminal base on the 3' side of the aforementioned base sequence (A1) of any of SEQ ID NOs. 45 to 81, or a nucleic acid molecule containing the aforementioned base sequence. That is, regarding the aforementioned HMGB1 binding nucleic acid molecule (A1), for example, ggg at the 5' end may be deleted in the aforementioned base sequence (A1) of any of SEQ ID NOs. 45 to 81.

The aforementioned base sequence (A1) may contain, for example, the motif sequence represented by SEQ ID NO. 114. In the base sequence below, it is preferable that n is adenine (a), cytosine (c), guanine (g), uracil (u), or thymine (t); and n of the 5th base is adenine (a), n of the 13th base is cytosine (c), and n of the 17th base is adenine (a). Examples of the aforementioned base sequence (A1) containing the motif sequence include #47 (SEQ ID NO. 65), #80 (SEQ ID NO. 67), R8c6_1 (SEQ ID NO. 74), and R8c6_14 (SEQ ID NO. 75).

Motif Sequence (SEQ ID NO. 114)
uaagncacguagnaccng

In the aforementioned HMGB1 binding nucleic acid molecule (A1), the respective bases are, for example, the same as those described above. That is, the aforementioned bases may be, for example, the aforementioned naturally occurring bases (non-artificial bases), i.e., adenine (a), cytosine (c), guanine (g), thymine (t), and uracil (u), and may be the aforementioned artificial bases (non-naturally occurring bases). The aforementioned artificial bases are the same as those described above. In the aforementioned HMGB1 binding nucleic acid molecule (A1), the bases represented by, for example, a, g, c, t, and u encompass, in addition to the aforementioned naturally occurring bases, the aforementioned artificial bases that function identically to the aforementioned respective naturally occurring bases.

For example, the constitutional unit of the aforementioned HMGB1 binding nucleic acid molecule (A1) is not particularly limited and may be the same as above. That is, an example of the aforementioned constitutional unit may be a nucleotide residue, and examples of the aforementioned nucleotide residue include ribonucleotide residues and deoxyribonucleotide residues. The aforementioned HMGB1 binding nucleic acid molecule (A1) may be, for example, an RNA composed of a ribonucleotide residue or a DNA composed of a deoxyribonucleotide residue, with an RNA being preferable. Also, the aforementioned HMGB1 binding nucleic acid molecule (A1) may contain both deoxyribonucleotide, which is a constitutional unit of a DNA, and ribonucleotide, which is a constitutional unit of an RNA. The aforementioned base sequences of SEQ ID NOs. 1 to 42 and SEQ ID NOs. 45 to 81, for example, may each be sequences in which bases as described above are successively present, and the base sequences may be RNAs composed of ribonucleotide residues, DNAs composed of deoxyribonucleotide residues, RNAs containing deoxyribonucleotide residues, or RNAs containing ribonucleotide residues.

Regarding the aforementioned HMGB1 binding nucleic acid molecule (A1), examples of the aforementioned constitutional unit include monomer residues such as PNAs, LNAs, and ENAs as described above. An example of the aforementioned HMGB1 binding nucleic acid molecule (A1) may be an RNA or a DNA that contains at least any of the monomer residues, i.e., PNAs, LNAs, and ENAs. In the case where the aforementioned HMGB1 binding nucleic acid molecule (A1) contains an aforementioned monomer residue, the number thereof is not particularly limited.

It is preferable that the aforementioned HMGB1 binding nucleic acid molecule (A1) is, for example, resistant to a nuclease. A technique for imparting the aforementioned nuclease resistance is not particularly limited and may be the same as above. It is preferable that the aforementioned HMGB1 binding nucleic acid molecule (A1) is, as described above, an RNA. In the case where the aforementioned HMGB1 binding nucleic acid molecule (A1) is an RNA, it is preferable that it is resistant to, for example, an RNA-degrading enzyme. A technique for imparting RNA-degrading enzyme resistance is not particularly limited and may be the same as above.

In the case where the aforementioned HMGB1 binding nucleic acid molecule (A1) is an RNA, it is preferable as described above that, for example, all nucleotide residues or some of the nucleotide residues constituting the RNA are the aforementioned modified nucleotide residues. Example of the aforementioned modified nucleotide residues include the modified nucleotide residues described above. Also, in the case where the aforementioned HMGB1 binding nucleic acid molecule (A1) is an RNA, it is preferable as described above that, for example, all nucleotide residues or some of the nucleotide residues constituting the RNA are the aforementioned deoxyribonucleotide residues and/or the aforementioned LNA residues. Also, in the case where the aforementioned HMGB1 binding nucleic acid molecule (A1) is an RNA, as described above, for example, among the nucleotide residues constituting the RNA, all or some of the nucleotide residues having uracil may be substituted with nucleotide residues having thymine, and specifically, may be substituted with deoxyribonucleotide residues having the aforementioned thymine. In the case where the aforementioned HMGB1 binding nucleic acid molecule (A1) is an RNA, it is preferable as described above that, for example, the HMGB1 binding nucleic acid molecule (A1) has the aforementioned PEG or the aforementioned deoxythymidine at the 5' end and/or the 3' end thereof. Accordingly, nucleic acid molecules composed of base sequences substituted with thymine or nucleic acid molecules containing the aforementioned base sequences can be regarded as examples of the nucleic acid molecule (A2), which will be described below.

The length of the aforementioned HMGB1 binding nucleic acid molecule (A1) is not particularly limited, and the overall length thereof is, for example, 20 to 160 bases long, preferably 30 to 120 bases long, and more preferably 40 to 100 bases long.

Next, the aforementioned nucleic acid molecule (A2) will now be described. Hereinafter, the aforementioned nucleic acid molecule (A2) is referred to as an HMGB1 binding nucleic acid molecule (A2).

(A2) A Nucleic Acid Molecule that Contains a Base Sequence in which One or a Plurality of Bases are Substituted, Deleted, Added, or Inserted in Regard to the Base Sequence Represented by any of SEQ ID NOs. 1 to 42, and that can Bind to HMGB1

The aforementioned HMGB1 binding nucleic acid molecule (A2) may be a nucleic acid molecule containing the aforementioned base sequence that is, for example, substituted, or may be a nucleic acid molecule composed of the aforementioned base sequence that is, for example, substituted. Regarding the aforementioned HMGB1 binding nucleic acid molecule (A2), the aforementioned base sequence that is, for example, substituted is also referred to as a base sequence (A2).

The phrase "one or a plurality of" is not particularly limited. Regarding the aforementioned base sequence of any of SEQ ID NOs. 1 to 42, the phrase "one or a plurality of" refers to, for example, 1 to 5, preferably 1 to 4, more preferably 1 to 3, even more preferably 1 or 2, and particularly preferably 1. Also, regarding the full-length sequence of the aforementioned HMGB1 binding nucleic acid sequence (A1), the phrase "one or a plurality of" refers to for example, 1 to 5, preferably 1 to 4, more preferably 1 to 3, even more preferably 1 or 2, and particularly preferably 1. A base used for the aforementioned substitution, addition, or insertion is not particularly limited, and may be, for example, the aforementioned naturally occurring base or may be the aforementioned artificial base. For substitution, addition, or insertion of the aforementioned base, for example, the aforementioned nucleotide residue may be used, or the aforementioned monomer residue may be used.

The HMGB1 binding nucleic acid molecule of the present invention may be, for example, the nucleic acid molecule (A3) below. Hereinafter, the aforementioned nucleic acid molecule (A3) is referred to as an HMGB1 binding nucleic acid molecule (A3).

(A3) A Nucleic Acid Molecule that Contains a Base Sequence having 60% or Greater Homology (Identity) to a Base Sequence Represented by any of SEQ ID NOs. 1 to 42 and that can Bind to HMGB1

The aforementioned HMGB1 binding nucleic acid molecule (A3) may be a nucleic acid molecule containing a base sequence having the aforementioned homology, or may be a nucleic acid molecule composed of a base sequence having the aforementioned homology. Regarding the aforementioned HMGB1 binding nucleic acid molecule (A3), a base sequence having the aforementioned homology is also referred to as a base sequence (A3).

The aforementioned homology is, for example, 70% or greater, preferably 80% or greater, more preferably 90% or greater, even more preferably 95% or greater, and particularly preferably 99% or greater. The aforementioned HMGB1 binding nucleic acid molecule (A3) may be, for example, a nucleic acid molecule that contains a base sequence having 60% or greater homology to the full-length sequence of the aforementioned HMGB1 binding nucleic acid sequence (A1), and that can bind to HMGB1. In this case, the aforementioned homology is, for example, 70% or greater, preferably 80% or greater, more preferably 90% or greater, even more preferably 95% or greater, and particularly preferably 99% or greater. The aforementioned homology can be obtained by, for example, calculating it using a BLAST or the like under default conditions.

The HMGB1 binding nucleic acid molecule of the present invention may be, for example, the nucleic acid molecule (A4) below. Hereinafter, the aforementioned nucleic acid molecule (A4) is referred to as an HMGB1 binding nucleic acid molecule (A4).

(A4) A Nucleic Acid Molecule that Contains a Base Sequence that Hybridizes with a Base Sequence Represented by any of SEQ ID NOs. 1 to 42 under Stringent Conditions or a Base Sequence that is Complementary to the Aforementioned Base Sequence, and that can Bind to HMGB1

The aforementioned HMGB1 binding nucleic acid molecule (A4) may be a nucleic acid molecule composed of the aforementioned hybridizing base sequence, or may be a nucleic acid molecule containing the aforementioned base sequence. Also, the aforementioned HMGB1 binding nucleic acid molecule (A4) may be a nucleic acid molecule composed of the aforementioned complementary base sequence, or may be a nucleic acid molecule containing the aforementioned complementary base sequence. Regarding the aforementioned HMGB1 binding nucleic acid molecule (A4), the aforementioned hybridizing base sequence and the aforementioned complementary base sequence are also referred to as base sequences (A4).

Regarding the aforementioned HMGB1 binding nucleic acid molecule (A4), the phrase "hybridizes under stringent conditions" refers to, for example, hybridization experiment conditions well-known to those skilled in the art. Specifically, the term "stringent conditions" refers to conditions where, for example, a base sequence can be identified by performing hybridization at 60 to 68° C. in the presence of 0.7 to 1 mol/L of NaCl and then washing at 65 to 68° C. using a 0.1 to 2-fold SSC solution. 1×SSC is composed of 150 mmol/L of NaCl and 15 mmol/L of sodium citrate. The aforementioned HMGB1 binding nucleic acid molecule (A4) may be, for example, a nucleic acid molecule that contains a base sequence that hybridizes with the full-length base of the aforementioned HMGB1 binding nucleic acid molecule (A1) under stringent conditions and that binds to HMGB1.

Regarding the aforementioned HMGB1 binding nucleic acid molecules (A2) to (A4), for example, base, constitutional unit, length, and imparting nuclease resistance, and other features are the same as those described for the aforementioned HMGB1 binding nucleic acid molecule (A1) unless specified otherwise.

Next, the aforementioned nucleic acid molecule (B1) will now be described. Hereinafter, the aforementioned nucleic acid molecule (B1) is referred to as an HMGB1 binding nucleic acid molecule (B1). Regarding the aforementioned HMGB1 binding nucleic acid molecule (B1), a base sequence represented by any of SEQ ID NOs. 45 to 81 is also referred to as a base sequence (B1).

(B1) A Nucleic Acid Molecule that Contains a Base Sequence Represented by any of SEQ ID NOs. 45 to 81

The base sequences represented by SEQ ID NOs. 45 to 81 are as described above. The base sequence represented by any of SEQ ID NOs. 45 to 81 contained in the HMGB1 binding nucleic acid molecule (B1) may be indicated by the nomenclature presented before a sequence ID number shown above. The aforementioned HMGB1 binding nucleic acid molecule (B1) may be, for example, a nucleic acid molecule composed of the base sequence (B1) represented by any of SEQ ID NOs. 45 to 81, or may be a nucleic acid molecule containing the aforementioned base sequence (B1).

The aforementioned HMGB1 binding nucleic acid molecule (B1) may be, for example, a nucleic acid molecule composed of a base sequence from the 4th base on the 5' side to the terminal base on the 3' side of the aforementioned base sequence (B1) of any of SEQ ID NOs. 45 to 81, or a nucleic acid molecule containing the aforementioned base sequence. That is, regarding the aforementioned HMGB1 binding nucleic acid molecule (B1), for example, ggg at the 5' end may be deleted in the aforementioned base sequence (B1) of any of SEQ ID NOs. 45 to 81.

The aforementioned base sequence (B1) may contain, for example, the motif sequence represented by SEQ ID NO. 114. In the base sequence below, it is preferable that n is adenine (a), cytosine (c), guanine (g), uracil (u), or thymine (t); and n of the 5th base is adenine (a), n of the 13th base is cytosine (c), and n of the 17th base is adenine (a). Examples of the aforementioned base sequence (B1) containing the motif sequence include #47 (SEQ ID NO. 65), #80 (SEQ ID NO. 67), R8c6_1 (SEQ ID NO. 74), and R8c6_14 (SEQ ID NO. 75).

Motif Sequence (SEQ ID NO. 114)
uaagncacguagnaccng

Figure 11:
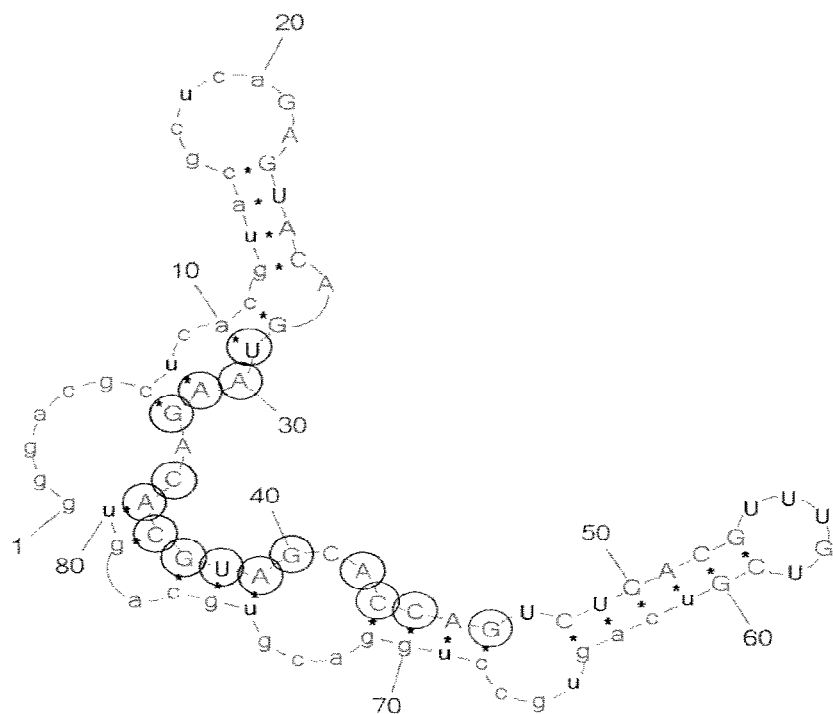
FIG. 11 is a diagram showing estimated secondary structures of RNA aptamers R8c6_1 (SEQ ID NO. 74) and R8c6_18 (SEQ ID NO. 87) of the present invention.
Figure 11:
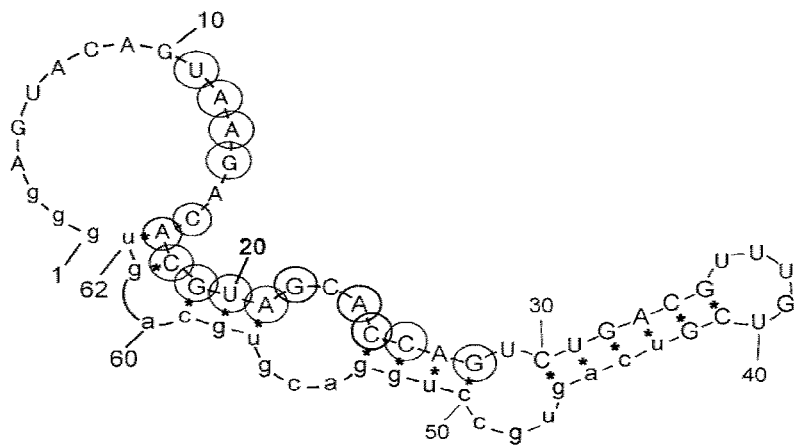

FIG. 11 shows an estimated secondary structure of the aforementioned R8c6_1 (SEQ ID No. 74). In the diagram, the circled bases correspond to the aforementioned motif sequence. In the estimated secondary structure of FIG. 11, the bases corresponding to "n" in the aforementioned motif sequence are not circled.

In the aforementioned HMGB1 binding nucleic acid molecule (B1), the respective bases are, for example, the same as those described above. That is, the aforementioned bases may be, for example, the aforementioned naturally occurring bases (non-artificial bases), i.e., adenine (a), cytosine (c), guanine (g), thymine (t), and uracil (u), and may be the aforementioned artificial bases (non-naturally occurring bases). The aforementioned artificial bases are the same as those described above. In the aforementioned HMGB1 binding nucleic acid molecule (B11), the bases represented by, for example, a, g, c, t, and u encompass, in addition to the aforementioned naturally occurring bases, the aforementioned artificial bases that function identically to the aforementioned respective naturally occurring bases.

For example, the constitutional unit of the aforementioned HMGB1 binding nucleic acid molecule (B1) is not particularly limited and may be the same as above. That is, an example of the aforementioned constitutional unit may be a nucleotide residue, and examples of the aforementioned nucleotide residue include ribonucleotide residues and deoxyribonucleotide residues. The aforementioned HMGB1 binding nucleic acid molecule (B1) may be, for example, an RNA composed of a ribonucleotide residue or a RNA composed of a deoxyribonucleotide residue, with an RNA being preferable. The aforementioned HMGB1 binding nucleic acid molecule (B1) may contain both deoxyribonucleotide, which is a constitutional unit of a DNA, and ribonucleotide, which is a constitutional unit of an RNA. It is sufficient that the aforementioned base sequences of SEQ ID NOs. 45 to 81 each are, for example, sequences in which bases as described above are successively present, and the base sequences may be RNAs composed of ribonucleotide residues, DNAs composed of deoxyribonucleotide residues, RNAs containing deoxyribonucleotide residues, or RNAs containing ribonucleotide residues.

Regarding the aforementioned HMGB1 binding nucleic acid molecule (B1), examples of the aforementioned constitutional unit include monomer residues such as PNAs, LNAs, and ENAs as described above. An example of the aforementioned HMGB1 binding nucleic acid molecule (B1) may be an RNA or a DNA that contains at least any of the monomer residues PNAs, LNAs, and ENAs. In the case where the aforementioned HMGB1 binding nucleic acid molecule (B1) contains an aforementioned monomer residue, the number thereof is not particularly limited.

It is preferable that the aforementioned HMGB1 binding nucleic acid molecule (B1) is, for example, resistant to a nuclease as described above. A technique for imparting the aforementioned nuclease resistance is not particularly limited and may be the same as above. It is preferable that the aforementioned HMGB1 binding nucleic acid molecule (B1) is, as described above, an RNA. In the case where the aforementioned HMGB1 binding nucleic acid molecule (B1) is an RNA, it is preferable that it is resistant to, for example, an RNA-degrading enzyme. A technique for imparting RNA-degrading enzyme resistance is not particularly limited and may be the same as above.

In the case where the aforementioned HMGB1 binding nucleic acid molecule (B1) is an RNA, it is preferable that, for example, all nucleotide residues or some of the nucleotide residues constituting the RNA are the aforementioned modified nucleotide residues as described above. Examples of the aforementioned modified nucleotide residues may be the modified nucleotide residues described above. Also, in the case where the aforementioned HMGB1 binding nucleic acid molecule (B1) is an RNA, it is preferable that, for example, all nucleotide residues or some of the nucleotide residues constituting the RNA are the aforementioned deoxyribonucleotide residues and/or the aforementioned LNA residues as described above. Also, in the case where the aforementioned HMGB1 binding nucleic acid molecule (B1) is an RNA, for example, among the nucleotide residues constituting the RNA, all or some of the nucleotide residues having uracil may be substituted with nucleotide residues having thymine, and specifically, may be substituted with the aforementioned deoxyribonucleotide residues having thymine as described above. In the case where the aforementioned HMGB1 binding nucleic acid molecule (B1) is an RNA, it is preferable that, for example, the HMGB1 binding nucleic acid molecule (B1) has the aforementioned PEG or the aforementioned deoxythymidine at the 5' end and/or the 3' end thereof, as described above. Accordingly nucleic acid molecules composed of base sequences substituted with thymine or nucleic acid molecules containing the aforementioned base sequences can be regarded as examples of the nucleic acid molecule (B2), which will be described below.

The length of the aforementioned HMGB1 binding nucleic acid molecule (B1) is not particularly limited, and the overall length thereof is, for example, 20 to 160 bases long, preferably 30 to 120 bases long, and more preferably 40 to 100 bases long.

It is preferable that the aforementioned HMGB1 binding nucleic acid molecule (B1) is, in particular, a nucleic acid molecule (b1) below. Hereinafter, the aforementioned nucleic acid molecule (b1) is also referred to as an HMGB1 binding nucleic acid molecule (b1). The aforementioned HMGB1 nucleic acid molecule (b1) may be, for example, a nucleic acid molecule composed of the base sequence SEQ ID No. 74, or may be a nucleic acid molecule containing the aforementioned base sequence.

(b1) A Nucleic Acid Molecule that Contains the Base Sequence Represented by SEQ ID NO. 74

Next, the aforementioned nucleic acid molecule (B2) will now be described. Hereinafter, the aforementioned nucleic acid molecule (B2) is referred to as an HMGB1 binding nucleic acid molecule (B2).

(B2) A Nucleic Acid Molecule that Contains a Base Sequence in which One or a Plurality of Bases are Substituted, Deleted, Added, or Inserted in Regard to the Base Sequence Represented by any of SEQ ID NOs. 45 to 81, and that can Bind to HMGB1

The aforementioned HMGB1 binding nucleic acid molecule (B2) may be a nucleic acid molecule containing the aforementioned base sequence that is, for example, substituted, or may be a nucleic acid molecule composed of the aforementioned base sequence that is, for example, substituted. Regarding the aforementioned HMGB1 binding nucleic acid molecule (B2), the aforementioned base sequence that is, for example, substituted is also referred to as a base sequence (B2).

The phrase "one or a plurality of" is not particularly limited, and it is sufficient that the aforementioned HMGB1 binding nucleic acid molecule (B2) can bind to HMGB1. In the base sequence of any of SEQ ID NOs. 45 to 81, the number of the aforementioned substituted bases is, for example, 1 to 5, preferably 1 to 4, more preferably 1 to 3, even more preferably 1 or 2, and particularly preferably 1. In the base sequence of any of SEQ ID NOs. 45 to 81, the number of the aforementioned added or inserted bases is, for example, 1 to 5, preferably 1 to 4, more preferably 1 to 3, even more preferably 1 or 2, and particularly preferably 1. In the base sequence of any of SEQ ID NOs. 45 to 81, the number of the aforementioned deleted bases is not particularly limited, and it is, for example, 1 to 46, 1 to 43, 1 to 21, 1 to 18, 1 to 4, 1 to 3, 2, or 1.

The length of the aforementioned HMGB1 binding nucleic acid molecule (B2) is not particularly limited, and the overall length thereof is, for example, 20 to 160 bases long, preferably 30 to 120 bases long, and more preferably 40 to 100 bases long.

Encompassed within the aforementioned HMGB1 binding nucleic acid molecule (B2), for example, a nucleic acid molecule that contains a base sequence in which one or a plurality of bases are deleted in regard to the base sequence represented by any of SEQ ID NOs. 45 to 81 and that can bind to HMGB1 can also be regarded as a shortened nucleic acid molecule obtained by shortening the aforementioned HMGB1 binding nucleic acid molecule (B1). The aforementioned shortened nucleic acid molecule is also referred to as a shortened HMGB1 binding nucleic acid molecule (B2). The aforementioned shortened HMGB1 binding nucleic acid molecule may be, as shown in (B2) above, a nucleic acid molecule that contains a base sequence in which not only one or a plurality of bases are deleted, but also, for example, one or a plurality of bases are substituted, added, or inserted in regard to the base sequence represented by any of SEQ ID NOs. 45 to 81 and that can bind to HMGB1.

The aforementioned shortened HMGB1 binding nucleic acid molecule (B2) may be, as described above, a nucleic acid molecule containing the aforementioned base sequence having a deletion, or may be a nucleic acid molecule composed of the aforementioned base sequence having a deletion. Regarding the aforementioned shortened HMGB1 binding nucleic acid molecule (B2), the aforementioned base sequence having a deletion is also referred to as a shortened base sequence. The number of deleted bases is not particularly limited and, for example, it is the same as above.

The aforementioned shortened HMGB1 binding nucleic acid molecule (B2) is, for example, a nucleic acid molecule composed of a base sequence from the 4th base on the 5' side to the terminal base on the 3' side of a base sequence of any of SEQ ID NOs. 45 to 81, or a nucleic acid molecule containing the aforementioned base sequence. That is, the aforementioned shortened HMGB1 binding nucleic acid molecule (B2) is, for example, a nucleic acid molecule composed of a base sequence (B1) of any of SEQ ID NOs. 45 to 81 in which ggg at the 5' end are deleted, or a nucleic acid molecule containing the aforementioned base sequence.

The length of the aforementioned shortened HMGB1 binding nucleic acid molecule (B2) is not particularly limited, and the overall length thereof is, for example, 20 to 160 bases long, preferably 30 to 120 bases long, and more preferably 40 to 100 bases long.

As the aforementioned shortened HMGB1 binding nucleic acid molecule (B2), for example, a nucleic acid molecule that contains a base sequence in which one or a plurality of bases are deleted in regard to the base sequence represented by SEQ ID NO. 74 and that can bind to HMGB1 is preferable, and specifically, the nucleic acid molecule (b2) below is preferable. Hereinafter, the aforementioned nucleic acid molecule (b2) is also referred to as a shortened HMGB1 binding nucleic acid molecule (b2).

(b2) A Nucleic Acid Molecule that Contains a Partial Sequence having 11 or more Consecutive Bases of the Base Sequence Represented by SEQ ID NO. 74 and that can Bind to HMGB1

Regarding the aforementioned shortened HMGB1 binding nucleic acid molecule (b2), the aforementioned partial sequence having 11 or more consecutive bases is hereinafter also referred to as a consecutive partial sequence. The aforementioned shortened HMGB1 binding nucleic acid molecule (b2) may be a nucleic acid molecule composed of the aforementioned consecutive partial sequence, or may be a nucleic acid molecule containing the aforementioned consecutive partial sequence. The aforementioned shortened HMGB1 binding nucleic acid molecule (b2) may be, for example, a nucleic acid molecule that contains a base sequence in which not only one or a plurality of bases are deleted, but also, for example, one or a plurality of bases are substituted, added, or inserted in regard to the base sequence represented by SEQ ID NO. 74 and that can bind to HMGB1 as described above.

The aforementioned consecutive partial sequence having 11 or more consecutive bases of the aforementioned base sequence of SEQ ID NO. 74 may be included one time or two or more times in the aforementioned shortened HMGB1 binding nucleic acid molecule (b2).

The length of the aforementioned consecutive partial sequence is 11 bases or longer as described above. The length of the aforementioned consecutive partial sequence is not particularly limited, and for example, may be 12 bases or longer, may be 14 bases or longer, and may be 16 bases or longer. The upper limit of the length of the aforementioned consecutive partial sequence is not particularly limited, and it is 80 bases or less, and preferably 79 bases or less.

The aforementioned consecutive partial sequence is not particularly limited, and examples include a y sequence, an x sequence, and a y' sequence as shown below. Examples of the aforementioned y sequence include a region covering the 1st to 20th bases and a region covering the 4th to 20th bases in the aforementioned base sequence of SEQ ID NO. 74. Examples of the aforementioned x sequence include regions covering the 21st to 60th bases, 22nd to 60th bases, 24th to 60th bases, 25th to 60th bases, 29th to 60th bases, 34th to 60th bases, 38th to 60th bases, 22nd to 48th bases, 22nd to 47th bases, 25th to 47th bases, 26th to 47th bases, 27th to 47th bases, 28th to 47th bases, 29th to 47th bases, 30th to 47th bases, 31st to 47th bases, 34th to 47th bases, 29th to 44th bases, 29th to 40th bases, 29th to 46th bases, 25th to 46th bases, 26th to 46th bases, 27th to 46th bases, 28th to 46th bases, and 29th to 46th bases in the aforementioned base sequence of SEQ ID NO. 74. Examples of the aforementioned y' sequence include regions covering the 61st to 80th bases, 61st to 79th bases, 61st to 77th bases, 61st to 76th bases, 61st to 78th bases, 64th to 80th bases, 65th to 80th bases, 70th to 80th bases, and 64th to 77th bases in the aforementioned base sequence of SEQ ID NO. 74.

A base sequence composed of the aforementioned consecutive partial sequence and a base sequence containing the aforementioned consecutive partial sequence are hereinafter also referred to as a base sequence (b2) collectively. The aforementioned shortened HMGB1 binding nucleic acid molecule (b2), for example, may be a nucleic acid molecule composed of the aforementioned base sequence (b2), or may be a nucleic acid molecule containing the aforementioned base sequence (b2). Examples of the aforementioned base sequence (b2) include a base sequence containing the aforementioned x sequence and the aforementioned y' sequence, and a base sequence containing the aforementioned y sequence, the aforementioned x sequence, and the aforementioned y' sequence. It is preferable that, for example, the aforementioned base sequence (b2) contains the aforementioned y sequence on the 5' side of the aforementioned x sequence, and the aforementioned y' sequence on the 3' side of the aforementioned x sequence. Regarding the aforementioned base sequence (b2), for example, ggg at the 5' end may be deleted in the aforementioned y sequence.

Examples of the aforementioned base sequence (b2) includes base sequences represented by SEQ ID NOs. 83 to 113. These base sequences are shown in Table 1 below. In Table 1 below, each base sequence is presented so as to correspond to the base sequence of SEQ ID NO. 74. Regarding each base sequence, in comparison to the base sequence of SEQ ID NO. 74, a deleted portion is blank, and a different base is underlined. The base sequences of SEQ ID NOs. 83 to 113 encompassed within the aforementioned shortened HMGB1 binding nucleic acid molecule (b2) may respectively be indicated by the nomenclatures shown in Table 1 below.

TABLE 1

| Aptamer | Sequence | SEQ No. |
|---|---|---|
| R8c6_1 | GGGACGCUCACGUACGCUCA GAGUACAGUAAGACACGUAGCACCAGUCUGACGUUUGUCG UCAGUGCCUGGACGUGCAGU | 74 |
| R8c6_1-1 | GGGACGCUCACGUACGCUCA GAGUACAGUAAGACACGUAGCACCAGUCUGACGUUUGUCG UCAGUGCCUGGACGUGCAG | 83 |
| R8c6_1-3 | GGGACGCUCACGUACGCUCA GAGUACAGUAAGACACGUAGCACCAGUCUGACGUUUGUCG UCAGUGCCUGGACGUGC | 84 |
| R8c6_1-4 | GGGACGCUCACGUACGCUCA GAGGACAGUAAGACACGUAGCACCAGUCUGACGUUUGUCG UCAGUGCCUGGACGUG | 85 |
| R8c6_1-15 | GGG                  CA GAGUACAGUAAGACACGUAGCACCAGUCUGACGUUUGUCG UCAGUGCCUGGACGUGCAGU | 86 |
| R8c6_1-18 | GGG                     AGUACAGUAAGACACGUAGCACCAGUCUGACGUUUGUCG UCAGUGCCUGGACGUGCAGU | 87 |
| R6c6_1-20 | GGG                       UACAGUAAGACACGUAGCACCAGUCUGACGUUUGUCG UCAGUGCCUGGACGUGCAGU | 88 |
| R8c6_1-21 | GGG                        ACAGUAAGACACGUAGCACCAGUCUGACGUUUGUCG UCAGUGCCUGGACGUGCAGU | 89 |
| R8c6_1-25 | GGG                            UAAGACACGUAGCACCAGUCUGACGUUUGUCG UCAGUGCCUGGACGUGCAGU | 90 |
| R8c6_1-30 | GGG                                 CACGUAGCACCAGUCUGACGUUUGUCG UCAGUGCCUGGACGUGCAGU | 91 |
| R8c6_1-34CC | GGG                                      UAGCACCAGUCUGACGUUUGUCG UCAGUGCCUGGACGUGCACC | 92 |
| R8c6_1-18 | GGG                     AGUACAGUAAGACACGUAGCACCAGUCUGACGUUUGUCG UCAGUGCCUGGACGUGCAGU | 87 |
| R8c6_1-18-S2 | GGG                  AGUACAGUAAGACACGUAGCACCAGUC G CGUUUGUCG   C GUGCCUGGACGUGCAGU | 93 |
| R8c6_1-18-S4 | GGG                  AGUACAGUAAGACACGUAGCACCAGUC   GUUUGUCG     UGCCUGGACGUGCAGU | 94 |
| R8c6_1-18-S6 | GGG                  AGUACAGUAAGACACGUAGCACCAGU                  GUGCCUGGACGUGCAGU | 95 |
| R8c6_1-21-S6 | GGG                     ACAGUAAGACACGUAGCACCAGU                  GUGCCUGGACGUGCAGU | 96 |
| R8c6_1-22-S6 | GGG                      CAGUAAGACACGUAGCACCAGU                  GUGCCUGGACGUGCAGU | 97 |
| R8c6_1-23-S6 | GGG                       AGUAAGACACGUAGCACCAGU                  GUGCCUGGACGUGCAGU | 98 |
| R8c6_1-24-S6 | GGG                        GUAAGACACGUAGCACCAGU                  GUGCCUGGACGUGCAGU | 99 |
| R8c6_1-25-S6 | GGG                         UAAGACACGUAGCACCAGU                  GUGCCUGGACGUGCAGU | 100 |
| R8c6_1-26-S6 | GGG                          AAGACACGUAGCACCAGU                  GUGCCUGGACGUGCAGU | 101 |
| R8c6_1-27-S6 | GGG                           AGACACGUAGCACCAGU                  GUGCCUGGACGUGCAGU | 102 |
| R8c6_1-25-S6A | GGG                         UAAG CACGUAGCACCAGU                  GUGCCUGGACGUGCAGU | 103 |

TABLE 1-continued

| Aptamer | Sequence | | | SEQ No. |
|---|---|---|---|---|
| R8c6_1-25-S6A2 | GGG | UAAGACACGUAGCACC GU | GUGCC GGACGUGGAGU | 104 |
| R8c6_1-25-S6A3 | GGG | UAAGACACGUAGCACCAGU | GUGCCUGGACGUGC GU | 105 |
| R8c6_1-25-S6C | GGG | UAAGACACGUAG ACCAGU | GUGCCUGGACGUGCAGU | 106 |
| R8c6_1-25-S6C2 | GGG | UAAGACACGUAGCACCAGU | GUGCCUGGA GUGCAGU | 107 |
| R9c6_1-21-S8 | GGG | ACAGUAAGACACGUAGCACCAG | UGCCUGGACGUGCAGU | 108 |
| R8c6_1-22-S8 | GGG | CAGUAAGACACGUAGCACCAG | UGCCUGGACGUGCAGU | 109 |
| R8c6_1-23-S8 | GGG | AGUAAGACACGUAGCACCAG | UGCCUGGACGUGCAGU | 110 |
| R8c6_1-24-S8 | GGG | GUAAGACACGUAGCACCAG | UGCCUGGACGUGCAGU | 111 |
| R8c6_1-25-S8 | GGG | UAAGACACGUAGCACCAG | UGCCUGGACGUGCAGU | 112 |
| R8c6_1-25-S8CA | GGG | UAAGACACGUAGAACCAG | UGACUGGAAGUGCAGU | 113 |

The aforementioned shortened HMGB1 binding nucleic acid molecule (b2) may be, for example, a nucleic acid molecule composed of a base sequence represented by any of SEQ ID NOs. 83 to 113, or may be a nucleic acid molecule containing a nucleic acid molecule composed of a base sequence represented by any of SEQ ID NOs. 83 to 113.

The aforementioned shortened HMGB1 binding nucleic acid molecule (b2) may be, for example, a nucleic acid molecule composed of a base sequence from the 4th base on the 5' side to the terminal base on the 3' side of the base sequence (b2) of any of SEQ ID NO. 74 and SEQ ID NOs. 83 to 113, or a nucleic acid molecule containing the aforementioned base sequence. That is, regarding the aforementioned shortened HMGB1 binding nucleic acid molecule (b2), for example, ggg at the 5' end may be deleted in the aforementioned base sequence of any of SEQ ID NO. 74 and SEQ ID NOs. 83 to 113.

The aforementioned base sequence (b2) may contain, for example, the motif sequence represented by SEQ ID NO. 114. In the base sequence below, it is preferable that n is adenine (a), cytosine (c), guanine (g), uracil (u), or thymine (t); and n of the 5th base is adenine (a), n of the 13th base is cytosine (c), and n of the 17th base is adenine (a). Examples of the base sequence (b2) containing the aforementioned motif sequence include R8c6_1-1 (SEQ ID NO. 83), R8c6_1-3 (SEQ ID NO. 84), R8c6_1-4 (SEQ ID NO. 85), R8c6_1-15 (SEQ ID NO. 86), R8c6_1-18 (SEQ ID NO. 87), R8c6_1-20 (SEQ ID NO. 88), R8c6_1-21 (SEQ ID NO. 89), R8c6_1-25 (SEQ ID NO. 90), R8c6_1-18-S2 (SEQ ID NO. 93), R8c6_1-18-S4 (SEQ ID NO. 94), R8c6_1-18-S6 (SEQ ID NO. 95), R8c6_1-21-S6 (SEQ ID NO. 96), R8c6_1-22-S6 (SEQ ID NO. 97), R8c6_1-23-S6 (SEQ ID NO. 98), R8c6_1-24-S6 (SEQ ID NO. 99), R8c6_1-25-S6 (SEQ ID NO. 100), R8c6_1-25-S6A3 (SEQ ID NO. 105), R8c6_1-25-S6C2 (SEQ ID NO. 107), R8c6_1-21-S8 (SEQ ID NO. 108), R8c6_1-22-S8 (SEQ ID NO. 109), R8c6_1-23-S8 (SEQ ID NO. 110), R8c6_1-24-S8 (SEQ ID NO. 111), R8c6_1-25-S8 (SEQ ID NO. 112), and the like. Examples of the base sequence (b2) containing a portion of the aforementioned motif sequences include R8c6_1-30 (SEQ ID NO. 91), R8c6_1-34CC (SEQ ID NO. 92), R8c6_1-26-S6 (SEQ ID NO. 101), R8-c6_1-25-S6A2 (SEQ ID NO. 104), R8c6_1-25-S6C (SEQ ID NO. 106), and the like.

Motif Sequence (SEQ ID NO. 114)
uaagncacguagnaccng

Figure 20:
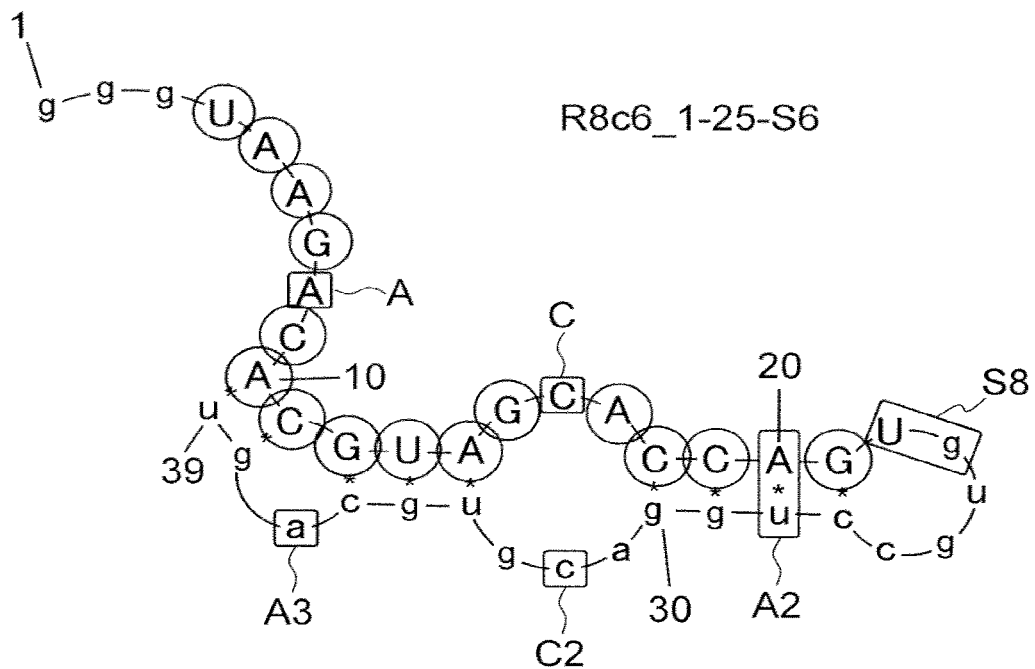
FIG. 20 is a diagram illustrating SEQ ID No. 100, and showing an estimated secondary structure of an RNA aptamer R8c6_1-25-S6 of the present invention.

FIG. 11 shows an estimated secondary structure of the aforementioned R8c6_1-18 (SEQ ID NO. 74). In the diagram, the circled bases correspond to the aforementioned motif sequence. In the aforementioned estimated secondary structure, the bases corresponding to "n" in the aforementioned motif sequence are not circled. FIG. 20 shows an estimated secondary structure of the aforementioned R8c6_1-25-S6 (SEQ ID NO. 100). In the diagram, the circled bases correspond to the aforementioned motif sequence. In the aforementioned estimated secondary structure, the bases corresponding to "n" in the aforementioned motif sequence are not circled.

The length of the aforementioned shortened HMGB1 binding nucleic acid molecule (b2) is not particularly limited, and the overall length thereof is, for example, to 160 bases long, preferably 30 to 120 bases long, and more preferably 40 to 100 bases long. Regarding the aforementioned shortened HMGB1 binding nucleic acid molecule (b2), the overall length thereof is not particularly limited, and the lower limit is, for example, 20 bases long or longer, 30 bases long or longer, 34 bases long or longer, 37 bases long or longer, and 40 bases long or longer, and the upper limit is, for example, 160 bases long or less, 120 bases long or less, 100 bases long or less, 80 bases long or less, and preferably 79 bases long or less.

The aforementioned shortened HMGB1 binding nucleic acid molecule (B2) may be, for example, a nucleic acid molecule that contains a base sequence in which one or a plurality of bases are substituted, deleted, added, or inserted in regard to the aforementioned consecutive partial sequence of the aforementioned shortened HMGB1 binding nucleic acid molecule (b2), and that can bind to HMGB1. A specific example may be a nucleic acid molecule that contains a base sequence in which one or a plurality of bases are substituted, deleted, added, or inserted in regard to the base sequence represented by any sequence ID number of SEQ ID NOs. 83 to 113, and that can bind to HMGB1. In the base sequence of any of SEQ ID NOs. 83 to 113, the number of the aforementioned, substituted bases is not particularly limited, and, for example, it is 1 to 5, preferably 1 to 4, more preferably 1 to 3, even more preferably 1 or 2, and particularly preferably 1.

The HMGB1 binding nucleic acid molecule of the present invention may be, for example, the nucleic acid molecule (B3) below. Hereinafter, the aforementioned nucleic acid molecule (B3) is referred to as an HMGB1 binding nucleic acid molecule (B13).

(B3) A Nucleic Acid Molecule that Contains a Base Sequence having 60% or Greater Homology (Identity) to the Base Sequence Represented by any of SEQ ID NOs. 45 to 81 and that can Bind to HMGB1

The aforementioned HMGB1 binding nucleic acid molecule (B3) may be a nucleic acid molecule containing a base sequence having the aforementioned homology, or may be a nucleic acid molecule composed of a base sequence having the aforementioned homology. The aforementioned homology is, for example, 70% or greater, preferably 80% or greater, more preferably 90% or greater, even more preferably 95% or greater, and particularly preferably 99% or greater. The aforementioned HMGB1 binding nucleic acid molecule (B3) may be, for example, a nucleic acid molecule that contains a base sequence having 60% or greater homology to the full-length sequence of the aforementioned HMGB1 binding nucleic acid sequence (B1), and that can bind to HMGB1. In this case, the aforementioned homology is, for example, 70% or greater, preferably 80% or greater, more preferably 90% or greater, even more preferably 95% or greater, and particularly preferably 99% or greater. The aforementioned homology can be obtained by, for example, calculating it using a BLAST or the like under default conditions.

The HMGB1 binding nucleic acid molecule of the present invention may be, for example, the nucleic acid molecule (B4) below. Hereinafter, the aforementioned nucleic acid molecule (B4) is referred to as an HMGB1 binding nucleic acid molecule (B4).

(B4) A Nucleic Acid Molecule that Contains a Base Sequence that Hybridizes with a Base Sequence Represented by any of SEQ ID NOs. 45 to 81 under Stringent Conditions or a Base Sequence that is Complementary to the Aforementioned Base Sequence, and that can Bind to HMGB1

The aforementioned HMGB1 binding nucleic acid molecule (B4) may be a nucleic acid molecule composed of the aforementioned hybridizing base sequence, or may be a nucleic acid molecule containing the aforementioned base sequence. Also, the aforementioned HMGB1 binding nucleic acid molecule (B4) may be a nucleic acid molecule composed of the aforementioned complementary base sequence, or may be a nucleic acid molecule containing the aforementioned complementary base sequence.

Regarding the aforementioned HMGB1 binding nucleic acid molecule (B4), the phrase "hybridizes under stringent conditions" refers to, for example, hybridization experiment conditions well-known to those skilled in the art. Specifically, the term "stringent conditions" refers to conditions where, for example, a base sequence can be identified by performing hybridization at 60 to 68° C. in the presence of 0.7 to 1 mol/L of NaCl and then washing at 65 to 68° C. using a 0.1 to 2-fold SSC solution. 1×SSC is composed of 150 mmol/L of NaCl and 15 mmol/L of sodium citrate. The aforementioned HMGB1 binding nucleic acid molecule (B4) may be, for example, a nucleic acid molecule that contains a base sequence that hybridizes with the full-length base of the aforementioned HMGB1 binding nucleic acid molecule (B1) under stringent conditions, and that binds to HMGB1.

Regarding the aforementioned HMGB1 binding nucleic acid molecules (B2) to (B4), for example, base, constitutional unit, length, and imparting nuclease resistance, and other features are the same as those described for the aforementioned HMGB1 binding nucleic acid molecule (B1) unless specified otherwise.

The HMGB1 binding nucleic acid molecule of the present invention may be, for example, a single-strand nucleic acid or may be a double-strand nucleic acid as described above. In the case where the HMGB1 binding nucleic acid molecule of the present invention is the aforementioned double-strand nucleic acid, it is preferable that, for example, one strand is a nucleic acid molecule of any of the aforementioned (A1) to (A4) and the aforementioned (B1) to (B4), and the other strand is a nucleic acid molecule composed of a base sequence complementary to the nucleic acid molecule of any of the aforementioned (A1) to (A4) and the aforementioned (B1) to (B4) or a nucleic acid molecule containing the aforementioned base sequence.

For example, when the MGB1 binding nucleic acid molecule of the present invention is used, a linker sequence such as polyadenine or the like may be further bound thereto insofar as the ability to bind to MGB1 is not adversely affected.

A method for producing the HMGB1 binding nucleic acid molecule of the present invention is not limited in any way, and the HMGB1 binding nucleic acid molecule can be synthesized by a known method such as a nucleic acid synthesizing method that takes advantage of chemical synthesis.

The HMGB1 binding nucleic acid molecule of the present invention may be, for example, a nucleic acid molecule composed of a base sequence represented by any of SEQ ID NOs. 1 to 42, or may be a nucleic acid molecule containing the aforementioned base sequence, as described above. In the latter case, the HMGB1 binding nucleic acid molecule of the present invention may contain, for example, a base sequence other than the aforementioned base sequence represented by any sequence ID number of SEQ ID NOs. 1 to 42. An example of one such embodiment of the HMGB1 binding nucleic acid molecule of the present invention may be, for example, a nucleic acid molecule that contains a Y region, an X region, and a Y' region and in which the aforementioned Y region, the aforementioned X region, and the aforementioned Y' region are connected from the 5' end. It is preferable that, in the aforementioned HMGB1 binding nucleic acid molecule of this embodiment, the aforementioned X region contains the aforementioned base sequence represented by any sequence ID number of SEQ ID NOs. 1 to 12, and the aforementioned Y region and the aforementioned Y' region are both composed of any base sequences.

The number of bases in the aforementioned X region is not particularly limited, and it is, for example, 10 to 60 bases, preferably 15 to 50 bases, and more preferably 20 to 40 bases. The number of bases in each of the aforementioned Y region and the aforementioned Y' region is not particularly limited, and it is, for example, 10 to 50 bases, preferably 15 to 40 bases, and more preferably 20 to 30 bases. The total number of bases in the HMGB1 binding nucleic acid molecule of the present invention is not particularly limited, and it is, for example, 20 to 160 bases, preferably to 120 bases, and more preferably 40 to 100 bases.

Neither the base sequence of the aforementioned Y region nor the base sequence of the aforementioned Y region is particularly limited, and it is preferable that, for example, they contain a primer binding sequence to which a primer can anneal, a polymerase recognition sequence that a polymerase can recognize, and the like. In the case where a large amount of nucleic acid molecules that can bind to a target is produced, more efficient production can be attained by, for example, a nucleic acid amplification method than the aforementioned chemical synthesis. Accordingly, in the case where the HMGB1 binding nucleic acid molecule of the present invention is amplified by a nucleic acid amplification method, it is preferable that the HMGB1 binding nucleic acid molecule of the present invention contains, for example, a primer binding sequence to which a primer can hybridize and a polymerase recognition sequence that a polymerase can recognize. It is preferable that the HMGB1 binding nucleic acid molecule of the present invention contains, for example, the aforementioned primer binding sequence and the aforementioned polymerase recognition sequence in at least one of upstream of the 5' side of the aforementioned X region, i.e., in the aforementioned Y region, and downstream of the 3' side of the aforementioned X region, i.e., in the aforementioned Y' region. The aforementioned polymerase recognition region can be suitably determined according to, for example, the type of polymerase used in nucleic acid amplification. In the case where the HMGB1 binding nucleic acid molecule of the present invention is an RNA, it is preferable that the aforementioned polymerase recognition sequence is, for example, a DNA-dependent RNA polymerase recognition sequence (hereinafter also referred to as an "RNA polymerase recognition sequence"), and a specific example may be a T7 promoter that is a T7 RNA polymerase recognition sequence or the like. In the case where the HMGB1 binding nucleic acid molecule of the present invention is an RNA, it is preferable that the aforementioned Y region on the 5' side contains, for example, the aforementioned RNA polymerase recognition sequence and the aforementioned primer binding sequence (hereinafter also referred to as a "5' side primer region") in this order. And it is preferable that the aforementioned X region is connected to the 3' side of the Y region. Moreover, it is preferable that the aforementioned Y region is connected to the 3' side of the aforementioned X region, and the aforementioned Y region contains a primer binding sequence (hereinafter also referred to as a "3' side primer region"). It is preferable that the aforementioned 5' side primer region in the aforementioned RNA is, for example, a sequence complementary to the 3' side of a DNA antisense strand synthesized using the aforementioned RNA as a template, i.e., a sequence identical to a primer that can bind to the 3' side of the aforementioned antisense strand. The HMGB1 binding nucleic acid molecule of the present invention may further have, for example, a region that assists binding to HMGB1. In the HMGB1 binding nucleic acid molecule of the present invention, for example, the aforementioned Y region and the aforementioned X region, as well as the aforementioned X region and the aforementioned Y region, may be immediately adjacent to each other or indirectly adjacent to each other via an intervening sequence.

A method for preparing the HMGB1 binding nucleic acid molecule of the present invention by nucleic acid amplification is not particularly limited. In the case where the HMGB1 binding nucleic acid molecule of the present invention is an RNA, it can be prepared using, for example, a DNA as a template. Hereinafter, a DNA strand that serves as an RNA template is also referred to as an antisense strand, and a DNA strand containing a sequence in which uracil (u) of the aforementioned RNA is substituted by thymine (t) is also referred to as a sense strand. It is preferable that the aforementioned template DNA contains, for example, one of a DNA (antisense strand) in which uracil (u) of a strand complementary to the aforementioned X region in the aforementioned RNA is substituted by thymine (t) and a DNA (sense strand) containing a sequence in which uracil (u) of the aforementioned X region is substituted by thymine (t). The aforementioned RNA can be amplified by using these DNAs as templates and performing nucleic acid amplification with a DNA-dependent DNA polymerase, and then using the resulting DNA amplification product as a template and further performing RNA transcription with a DNA-dependent RNA polymerase. Also, the aforementioned RNA may be amplified by using the aforementioned RNA as a template and preparing a cDNA by a reverse transcription reaction with an RNA-dependent DNA polymerase, using the aforementioned cDNA as a template and performing nucleic acid amplification of a DNA by PCR or the like, and using the resulting DNA amplification product as a template and further performing RNA transcription with a DNA-dependent RNA polymerase.

In the case where the HMGB1 binding nucleic acid molecule of the present invention is a DNA, the DNA can be amplified by, for example, a polymerase chain reaction (PCR) method or the like.

Regarding the HMGB1 binding nucleic acid molecule of the present invention, an example of the aforementioned X region may be the x sequence presented above.

Regarding the HMGB1 binding nucleic acid molecule of the present invention, as described above, neither the base sequences of the aforementioned Y region nor the aforementioned Y' region is particularly limited, and they can both be determined liberally. Examples of the sequence of the aforementioned Y region include a sequence containing a base sequence represented by either SEQ ID NO. 43 or SEQ ID NO. 115 and a sequence composed of the aforementioned base sequence. Also, an example of the aforementioned Y region may be the y sequence presented above. These sequences are examples and do not limit the present invention.

(SEQ ID NO. 43)
gggacgcucacguacgcuca (SEQ ID NO. 115)
acgcucacguacgcuca

Examples of the sequence of the aforementioned Y' region include a sequence containing the base sequence represented by SEQ ID NO. 44 and a sequence composed of the aforementioned base sequence. Also, an example of the aforementioned Y' region may be the y' sequence presented above. These sequences are examples and do not limit the present invention.

ucagugccuggacgugcagu (SEQ ID NO. 44)

The HMGB1 binding nucleic acid molecule of the present invention may have, for example, a secondary structure due to self-annealing. An example of the aforementioned secondary structure may be a stem-loop structure. The stem-loop structure may be formed due to, for example, the formation of a double strand by any of the aforementioned Y region, the aforementioned X region, and the aforementioned Y' region. Specifically, for example, the stem-loop structure may be formed due to the formation of a double strand between a part of the aforementioned Y region and a part of the aforementioned X region, or the stem-loop structure may be formed due to the formation of a double strand between a part of the aforementioned Y' region and a part of the aforementioned X region. Moreover, it is also possible that a part of the aforementioned Y region and a part of the aforementioned Y' region each form a double strand with a part of the aforementioned X region, thereby forming the stem-loop structure. The stem-loop structure may be formed due to the formation of a double strand inside the aforementioned Y region, and the stem-loop structure may be formed due to the formation of a double strand inside the Y' region, or the stem-loop structure may be formed inside the aforementioned Y region and the aforementioned Y' region.

Since the HMGB1 binding nucleic acid molecule of the present invention can bind to HMGB1, it can be used as, for example, a neutralizer that neutralizes the function of HMGB1 due to binding to HMGB1.

Since the HMGB1 binding nucleic acid molecule of the present invention can bind to HMGB1 as described above, it can be used as, for example, a inhibitor that inhibits the function of HMGB1 due to binding to HMGB1.

Since the HMGB1 binding nucleic acid molecule of the present invention can bind to HMGB1 as described above, it can be used as a pharmaceutical product for preventing or treating a disease caused by expression of HMGB1. The aforementioned pharmaceutical product of the present invention can be used as, for example, an anti-cancer agent, an anti-inflammatory agent, an anti-apoplexy agent, and the like.

It is sufficient that the neutralizer of the present invention, the inhibitor of the present invention, and the pharmaceutical product of the present invention contain the HMGB1 binding nucleic acid molecule of the present invention, and other configurations are not limited in any way. The neutralizer of the present invention, the inhibitor of the present invention, and the pharmaceutical product of the present invention may each contain, in addition to the HMGB1 binding nucleic acid molecule of the present invention, for example, a carrier or the like, and for example, they may have the same configuration as the composition presented below and can be used in the same manner.

<Composition>

The composition of the present invention is characterized by, as described above, containing the HMGB1 binding nucleic acid molecule of the present invention. It is sufficient that the composition of the present invention contains the aforementioned HMGB1 binding nucleic acid molecule of the present invention, and other configurations are not limited in any way.

Since the composition of the present invention can bind to HMGB1 as described above, it can be used as, for example, a neutralizer that neutralizes the function of HMGB1 due to binding to HMGB1.

Since the composition of the present invention can bind to HMGB1 as described above, it can be used as, for example, a inhibitor that inhibits the function of HMGB1 due to binding to HMGB1.

Since the composition of the present invention can bind to HMGB1 as described above, it can be used as a pharmaceutical product for preventing or treating a disease caused by expression of HMGB1. The aforementioned pharmaceutical product of the present invention can be used as, for example, an anti-cancer agent, an anti-inflammatory agent, an anti-apoplexy agent, and the like.

The subject to which the composition of the present invention is applied is not particularly limited, and can be suitably determined according to the intended use thereof. Examples of the subject of application include cells, tissues, living bodies, and the like. The origin of the aforementioned cells and tissues and the kind of the living bodies are not particularly limited. Examples of the aforementioned living bodies include organisms having an HMGB1 gene and/or an HMGB1 orthologous gene, and specific examples include animals such as humans, non-human mammals excluding humans, birds, and fish. In the case of administration into the living body, the administration method is not particularly limited, and examples include oral administration and parenteral administration. Examples of the aforementioned parenteral administration include intravenous administration, arterial administration, lymphatic administration, intramuscular administration, subcutaneous administration, rectal administration, dermal administration, intraperitoneal administration, local administration, and the like.

The composition of the present invention may also contain, for example, various additives in addition to the HMGB1 binding nucleic acid molecule of the present invention. The aforementioned additives are not particularly limited, and can be suitably determined according to, for example, the intended use of the composition of the present invention.

In the case where the HMGB1 binding nucleic acid molecule of the present invention is delivered, for example, to a cell or tissue, inside a living body, or the like, it is preferable that the composition of the present invention further contains a carrier as the aforementioned additive. The aforementioned carrier is not particularly limited, and examples include nanoparticles, liposomes, micelles, reversed micelles, polycations, cytopermeabile peptides, magnetic particles, calcium phosphate, and the like. The aforementioned nanoparticles are not particularly limited, and examples include nano carbon such as carbon nanohorn and carbon nanotube. These carriers may be used singly or may be used as a combination of two or more. Examples of the aforementioned additives include buffers, metal salts, surfactants, and the like.

<Detection Reagent>

The detection reagent of the present invention is an HMGB1 detection reagent for detecting the aforementioned HMGB1, characterized by containing the aforementioned HMGB1 binding nucleic acid molecule of the present invention. It is sufficient for the present invention that the detection reagent contains the aforementioned HMGB1 binding nucleic acid molecule of the present invention, and other configurations are not limited in any way.

The HMGB1 binding nucleic acid molecule of the present invention can bind to HMGB1 as described above. Therefore, for example, by checking the presence or absence of binding between the HMGB1 binding nucleic acid molecule of the present invention and HMGB1 using the detection reagent of the present invention, HMGB1 in a sample can be qualitatively or quantitatively measured. The method for checking the presence or absence of binding between the aforementioned HMGB1 binding nucleic acid molecule and HMGB1 is not particularly limited, and known methods for detecting binding between a nucleic acid and a protein can be used. Accordingly, use of the detection reagent of the present invention enables HMGB1 to be readily detected, and thus the detection reagent is useful, for example, in the biochemistry and clinical fields.

<Treatment Method>

The treatment method of the present invention is characterized by including the step of administering the HMGB1 binding nucleic acid molecule of the present invention into a subject having the aforementioned disease in which HMGB1 is involved. The aforementioned disease in which HMGB1 is involved is not particularly limited, and examples include at least one disease selected from the group consisting of cancer, inflammation, and apoplexy. Examples of the aforementioned cancer include breast cancer, colon cancer, melanoma, prostatic cancer, pancreatic cancer, lung cancer, and the like. The treatment method of the present invention enables, for example, prevention of the aforementioned disease, inhibition of progression of the aforementioned disease, treatment of the aforementioned disease, or the like. The treatment method of the present invention also encompasses a prevention method, and may include the step of administering the HMGB1 binding nucleic acid molecule of the present invention into a subject at a risk of the aforementioned disease. A method for administering the HMGB1 binding nucleic acid molecule of the present invention, administration conditions, and the like are not particularly limited, and are as described above. The aforementioned administration subject (for example, a patient) also is not particularly limited. Examples of the aforementioned living bodies include organisms having an HMGB1 gene and/or an HMGB1 orthologous gene, and specific examples include animals such as humans, non-human mammals excluding humans, birds, and fish. In the aforementioned administering step, for example, the composition of the present invention may be administered.

The present invention is characterized by being a nucleic acid molecule for use in treatment of the aforementioned disease in which HMGB1 is involved. The aforementioned nucleic acid molecule is the aforementioned HMGB1 binding nucleic acid molecule of the present invention. The aforementioned HMGB1 binding nucleic acid molecule of the present invention is as described above. Moreover, the present invention is characterized by being a composition for use in treatment of the aforementioned disease in which HMGB1 is involved. The composition is the aforementioned composition of the present invention containing the aforementioned HMGB1 binding nucleic acid molecule of the present invention. The aforementioned composition of the present invention is as described above.

EXAMPLES

Next, the examples of the present invention shall be described. The present invention, however, is not limited by the following examples. Commercially available reagents were used according to their protocols unless specified otherwise.

Example 1

RNA aptamers that can bind to HMGB1 were prepared, and the ability of each RNA aptamer to bind to HMGB1 was examined.

(1) RNA Aptamers

RNA aptamers #47 (SEQ ID NO. 65), #80 (SEQ ID NO. 67), #06 (SEQ ID NO. 56), #36 (SEQ ID NO. 60), #34 (SEQ ID NO. 63), #08 (SEQ ID NO. 46), and #10 (SEQ ID NO. 58) were prepared according to a known nucleic acid synthesizing method, and used as RNA aptamers of the example. An RNA library (40N) containing a plurality of RNAs composed of the oligonucleotide represented by SEQ ID NO. 82 below containing a 40-base-long random sequence was used as the RNA of a comparative example (the same also applies below). In SEQ ID NO. 82, "n" is adenine, guanine, cytosine, thymine, or uracil.

```
40N
                                            (SEQ ID NO. 82)
gggacgcucacguacgcucannnnnnnnnnnnnnnnnnnnnnnnnnnnnnn nnnnnnnnnnucagugccuggacgugcagu
```

(2) Ability to Bind to His-tag-added HMGB1

The ability of each of the aforementioned RNA aptamers to bind to HMGB1 in which His-tag was added to the N-terminus (His-tag-added HMGB1) was examined. For the analysis of the aforementioned binding ability, a BIACORE (registered trademark) X (manufactured by GE Healthcare) was used according to its instruction manual.

First, a sensor chip (trade name: Sensor Chip SA, manufactured by GE Healthcare) specially made for a BIACORE was set on the aforementioned BIACORE (registered trademark) X. Biotinylate deoxythymidine (5 µmol/L) was injected into the flow cell 2 of the aforementioned sensor chip using a running buffer and subjected to binding until the signal intensity (RU: resonance unit) reached about 1000 RU. For the aforementioned biotinylated deoxythymidine, 20-base-long deoxythymidine in which the 5' end was biotinylated was used. Then, 10 µg/mL of an RNA aptamer was injected at a flow rate of 20 µL/min for 1 min into the aforementioned flow cells 1 and 2 of the aforementioned chip using a running buffer and subjected to binding until the signal intensity reached about 1000 RU. Next, 675 nmol/L of the aforementioned His-tag-added HMGB1 was injected at a flow rate of 20 µL/min for 30 sec using the aforementioned running buffer, and under the same conditions the aforementioned running buffer was allowed to flow continuously for washing. Simultaneously with the injection of the aforementioned His-tag-added HMGB1 and washing with the aforementioned running buffer, signal intensity was measured. The aforementioned running buffer was composed of 20 mmol/L of HEPES, 500 mmol/L of NaCl, 0.1 mmol/L of $MgCl_2$, and 0.1% Triton X-100 (registered trademark), with the pH thereof being 7.2. As a blocking agent for suppressing non-specific binding, tRNA was used in a concentration of 1 mg/mL. In a comparative example, signal intensity was measured in the same manner except that the aforementioned comparative example RNA was used in place of the aforementioned example RNA aptamers. FIG. 1 shows the results.

FIG. 1 is a graph showing the ability of each RNA aptamer to bind to the aforementioned His-tag-added HMGB1. In the graph of FIG. 1, the vertical axis indicates the signal intensity (RU) measured by the aforementioned BIACORE (registered trademark) X, and the horizontal axis indicates the analysis time (sec). In the horizontal axis, the time from −10 sec to 0 sec is the time of pre-washing with the aforementioned running buffer, the time at 0 sec is when the injection of the aforementioned His-tag-added HMGB1 was started, the time from 0 sec to 30 sec is the injection time of the aforementioned His-tag-added HMGB1, and the time from 30 sec onward is the time of washing with the aforementioned running buffer.

As shown in FIG. 1, in the case where the aforementioned RNA of the comparative example was used, no increase in signal intensity was observed, and it was thus found that the RNA did not bind to the aforementioned His-tag-added HMGB1. In contrast, an increase in signal intensity was observed with each RNA aptamer of the example, and it was thus found that the RNA aptamers were bound to the aforementioned His-tag-added HMGB1.

Then, from the resulting signal intensities, the dissociation constant between each RNA aptamer and the aforementioned His-tag-added HMGB1 was obtained. The results are shown in Table 2 below. As shown in Table 2 below, while the dissociation constant of the aforementioned RNA of the comparative example was $1.04 \times 10^{-6}$, the aforementioned RNA aptamers of the example each showed a superior dissociation constant value of on the order of $10^{-1}$ to $10^{-7}$, and it was thus found that the RNA aptamers had excellent ability to bind to the aforementioned His-tag-added HMGB1. In particular, the #06 and #08 RNA aptamers had a dissociation constant on the order of $10^{-10}$ and $10^{-11}$, respectively, thus demonstrating a sufficiently lower order of magnitude than that of a generally attained order of magnitude of antibodies ($10^{-9}$ order), i.e., a sufficiently high level of binding ability. Moreover, the #47 and #80 RNA aptamers showed on the order of $10^{-12}$ and 10$^{-13}$, respectively, and these orders of magnitude are at a level that had not been reported at the time of the filing of the present application.

TABLE 21

| No. | | Dissociation constant |
|---|---|---|
| Comparative example RNA | | $1.04 \times 10^{-6}$ |
| Example RNA aptamer | #06 | $4.38 \times 10^{-10}$ |
| | #08 | $1.57 \times 10^{-11}$ |
| | #10 | $3.24 \times 10^{-7}$ |
| | #47 | $6.09 \times 10^{-12}$ |
| | #80 | $3.90 \times 10^{-13}$ |
| | R8c6_1 | $7.52 \times 10^{-14}$ |

(3) Ability to Bind to HMGB1

Figure 2:
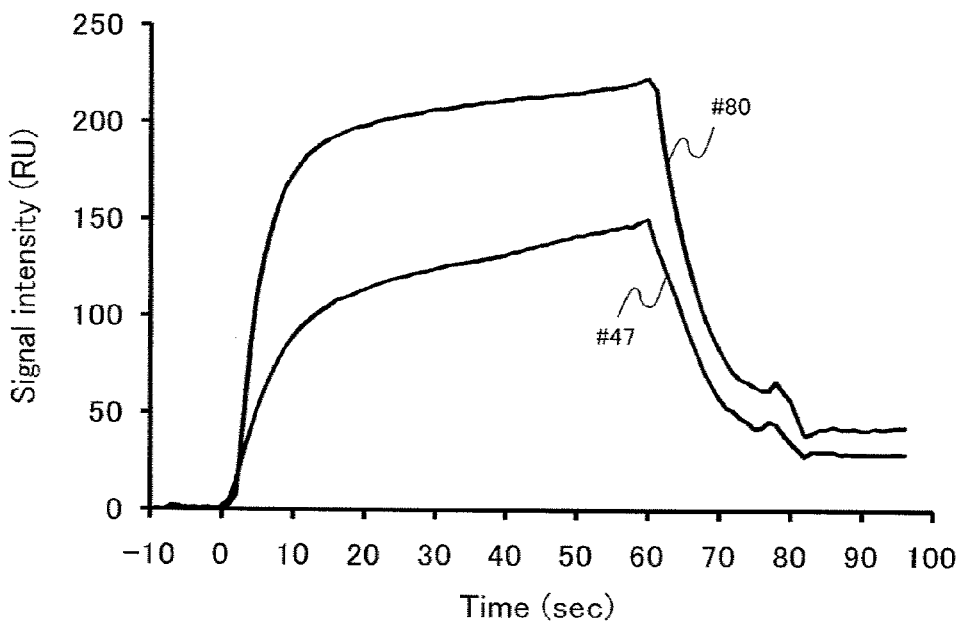
FIG. 2 is a graph showing the ability of each RNA aptamer to bind to HMGB1 in Example 1 of the present invention.

The ability of each of the aforementioned RNA aptamers to bind to HMGB1 in which no His-tag was added to the N-terminus was examined. An analysis of the aforementioned binding ability was carried out in the same manner as in (2) above except that 1 μmol/L of the aforementioned HMGB1 was used in place of the aforementioned His-tag-added HGB1 and the injection time of the aforementioned HMGB1 was 60 sec. FIG. 2 shows the results.

FIG. 2 is a graph showing the ability of each RNA aptamer to bind to the aforementioned HMGB1. In the graph of FIG. 2, the vertical axis indicates the signal intensity (RU) measured by the aforementioned BIACORE (registered trademark) X, and the horizontal axis indicates the analysis time (se). In the horizontal axis, the time from −10 sec to 0 see is the time of pre-washing with the aforementioned running buffer, the time at 0 see is when the injection of the aforementioned HMGB1 was started, the time from 0 sec to 60 see is the injection time of the aforementioned HMGB1, and the time from 60 sec onward is the time of washing with the aforementioned running buffer.

As shown in FIG. 2, each RNA aptamer of the example also showed a high level of ability to bind to HMGB1 to which His-tag was not added. It was found from this result that the RNA aptamers of the example are RNA aptamers that bind to, not His-tag, but HMGB1.

(4) Ability to Bind to His-tag

Figure 3:
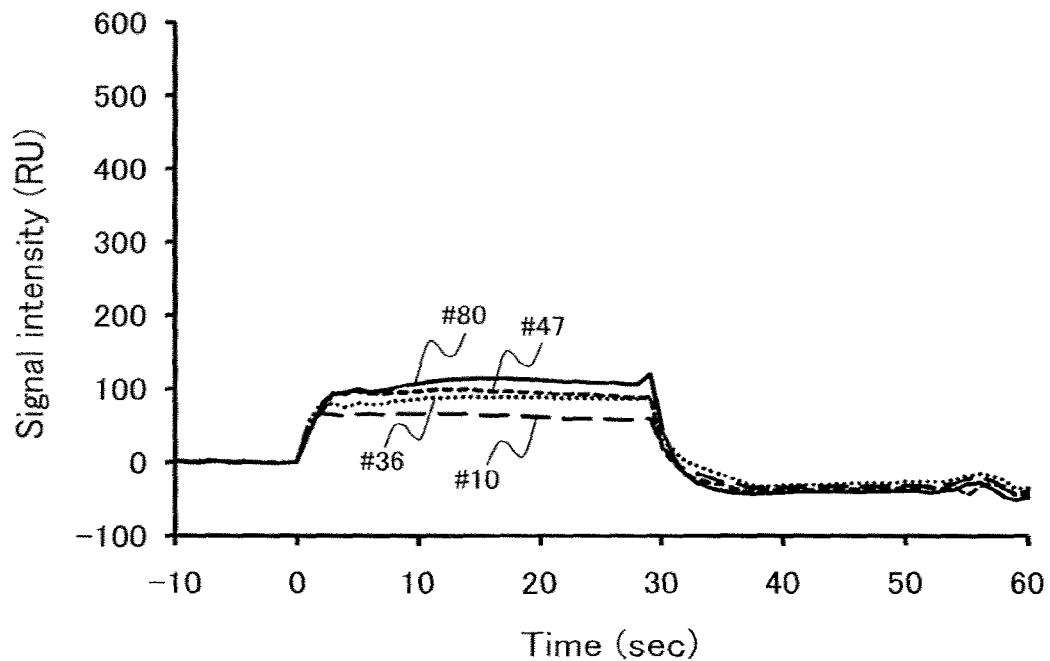
FIG. 3 is a graph showing the ability of each RNA aptamer to bind to His-tag-added MIF protein in Example 1 of the present invention.

The ability of each of the aforementioned RNA aptamers to bind to His-tag was examined. An analysis of the aforementioned binding ability was carried out in the same manner as in (2) above except that 300 nmol/L of the aforementioned His-tag-added MIF protein was used in place of the aforementioned His-tag-added HMGB1. FIG. 3 shows the results.

FIG. 3 is a graph showing the ability of each RNA aptamer to bind to the aforementioned His-tag-added MIF protein. In the graph of FIG. 3, the vertical axis indicates the signal intensity (RU) measured by the aforementioned BIACORE (registered trademark) X, and the horizontal axis indicates the analysis time (sec). In the horizontal axis, the time from −10 sec to 0 sec is the time of pre-washing with the aforementioned running buffer, the time at 0 sec is when the injection of the aforementioned His-tag-added MIF protein was started, the time from 0 sec to 30 sec is the injection time of the aforementioned His-tag-added MIF protein, and the time from 30 sec onward is the time of washing with the aforementioned running buffer.

As shown in FIG. 3, each RNA aptamer of the example showed a slight increase in signal intensity during injection of His-tag-added MIF protein (0 sec to 30 set), but the signal intensity did not increase over time, and a rapid decrease in signal intensity was observed due to washing performed after 30 sec, and eventually the signal intensity reached 0. This demonstrated that none of the RNA aptamers of the example binds to His-tag.

(5) Ability to Bind to HMGB1 under Physiological Conditions of Living Body

Figure 4:
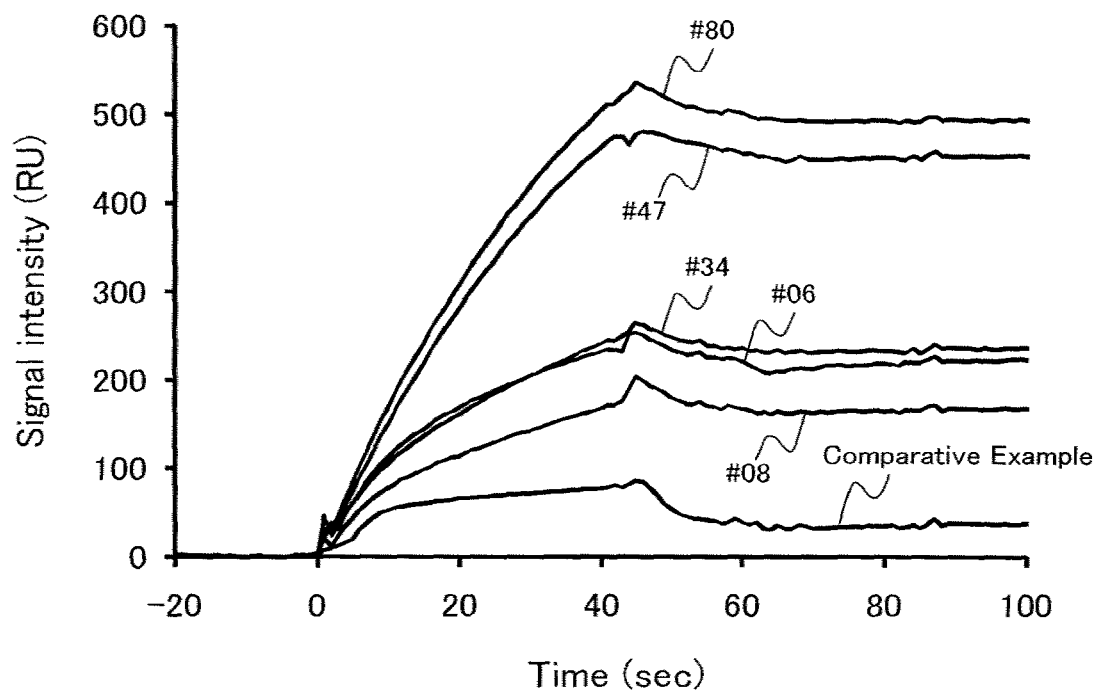
FIG. 4 is a graph showing the ability of each RNA aptamer to bind to HMGB1 under physiological conditions in Example 1 of the present invention.

The ability of each of the aforementioned RNA aptamers to bind to HMGB1 under physiological conditions was examined. An analysis of binding ability was carried out in the same manner as in (2) above except that the 500 mmol/L NaCl concentration of the aforementioned running buffer was changed so as to conform to the physiology condition of a living body of 150 mmol/L, and the injection time of the aforementioned His-tag-added HMGB1 was 45 sec. FIG. 4 shows the results.

FIG. 4 is a graph showing the ability of each RNA aptamer to bind to the aforementioned HMGB1 under physiological conditions. In the graph of FIG. 4, the vertical axis indicates the signal intensity (RU) measured by the aforementioned BIACORE (registered trademark) X, and the horizontal axis indicates the analysis time (sec). In the horizontal axis, the time from −20 sec to 0 sec is the time of pre-washing with the aforementioned running buffer, the time at 0 sec is when the injection of the aforementioned HMGB1 was started, the time from 0 sec to 45 sec is the injection time of the aforementioned HMGB1, and the time from 45 sec onward is the time of washing with the aforementioned running buffer.

As shown in FIG. 4, each RNA aptamer of the example also showed a high level of ability to bind to the aforementioned HMGB1 under physiological conditions. It was found from this result that the RNA aptamers of the example are aptamers that bind to HMGB1 also under physiological conditions. Accordingly, it can be said that, for example, even when the RNA aptamer of the present invention is administered into a living body, the RNA aptamer can bind to HMGB1 in the living body while demonstrating excellent binding ability.

Example 2

RNA aptamers that can bind to HMGB1 were prepared, and the ability of each RNA aptamer to bind to HMGB1 was examined.

(1) RNA Aptamers

RNA aptamers R8c6_1 (SEQ ID NO. 74) and R8c6_14 (SEQ ID NO. 75) were prepared according to a known nucleic acid synthesizing method, and used as RNA aptamers of the example.

(2) Ability to Bind to His-tag-added HMGB1

Figure 5:
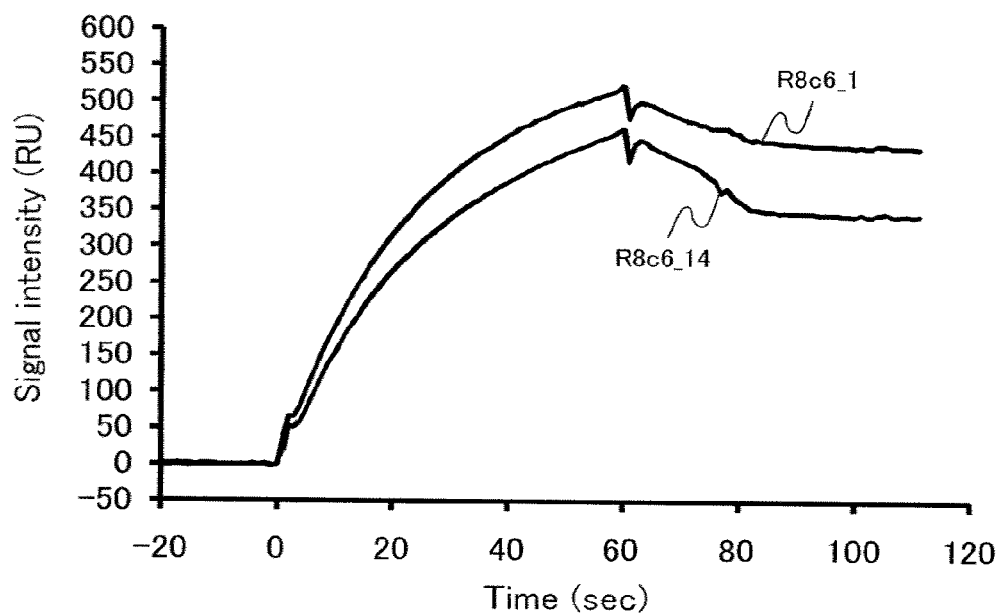
FIG. 5 is a graph showing the ability of each RNA aptamer to bind to His-tag-added HMGB1 in Example 2 of the present invention.

An analysis of ability to bind to His-tag added HMGB1 was carried out in the same manner as in (2) above of the aforementioned Example 1 except that the RNA aptamers prepared in (1) above were used, the concentration of the aforementioned His-tag added HMGB1 was 1 μmol/L, and the injection time was 60 seconds. FIG. 5 shows the results.

FIG. 5 is a graph showing the ability of each RNA aptamer to bind to the aforementioned His-tag-added HMGB1. In the graph of FIG. 5, the vertical axis indicates the signal intensity (RU) measured by the aforementioned BIACORE (registered trademark) X, and the horizontal axis indicates the analysis time (sec). In the horizontal axis, the time from −20 sec to 0 sec is the time of pre-washing with the aforementioned running buffer, the time at 0 sec is when the injection of the aforementioned His-tag-added HMGB1 was started, the time from 0 sec to 60 sec is the injection time of the aforementioned His-tag-added HMGB1, and the time from 60 sec onward is the time of washing with the aforementioned running buffer.

As shown in FIG. 5, an increase in signal intensity was observed with each RNA aptamer of the example, and it was thus found that the RNA aptamers were bound to the aforementioned HMGB1. Moreover the R8c6_1 and R8c6_14 RNA aptamers had a very low dissociation constant of $7.52 \times 10^{-14}$ and $1.06 \times 10^{-13}$, respectively, demonstrating greatly superior binding ability.

Example 3

The RNA aptamer having R8c6_1 (SEQ ID NO. 74) was further shortened, and the ability to bind to HMGB1 was examined.
(1) RNA Aptamers
The RNA aptamers shown in Table 3 below were each prepared according to a known nucleic acid synthesizing method, and used as RNA aptamers of the example. Each of the aforementioned RNA aptamers was a base sequence prepared by deleting a 5' side region or a 3' side region from R8c6_1.

R8c6_1-18, R8c6_1-20, and R8c6_1-21 in which 5' sides of R8c6_1 were deleted demonstrated binding ability superior to R8c6_1.

Example 4

RNA aptamers prepared by shortening R8c6_1 (SEQ ID NO. 74) were fluorinated, and their binding ability to HMGB1 was examined.
(1) RNA Aptamers
RNA aptamers as shown in Table 3 above of the aforementioned Example 3 were each prepared according to a known nucleic acid synthesizing method using 2'-fluoro-CTP and 2'-fluoro-UTP in which the 2' position of the ribose residue was fluorinated (the same also applies below), and used as fluorinated RNA aptamers of the example. The aforementioned fluorinated RNA aptamers have base sequences as shown in Table 3 above but the cytosine nucleotide residue and the uracil nucleotide residue are fluorinated. The fluorinated RNA aptamers were respectively designated as 2'F-R

TABLE 3

| Aptamer | Sequence | SEQ No. |
| --- | --- | --- |
| R8c6_1 | GGGACGCUCACGUACGCUCA GAGUACAGUAAGACACGUAGCACCAGUCUGACGUUUGUCG UCAGUGCCUGGACGUGCAGU | 74 |
| R8c6_1-1 | GGGACGCUCACGUACGCUCA GAGUACAGUAAGACACGUAGCACCAGUCUGACGUUUGUCG UCAGUGCCUGGACGUGCAG | 83 |
| R8c6_1-3 | GGGACGCUCACGUACGCUCA GAGUACAGUAAGACACGUAGCACCAGUCUGACGUUUGUCG UCAGUGCCUGGACGUGC | 84 |
| R8c6_1-4 | GGGACGCUCACGUACGCUCA GAGUACAGUAAGACACGUAGCACCAGUCUGACGUUUGUCG UCAGUGCCUGGACGUG | 85 |
| R8c6_1-15 | GGG CA GAGUACAGUAAGACACGUAGCACCAGUCUGACGUUUGUCG UCAGUGCCUGGACGUGCAGU | 86 |
| R8c6_1-18 | GGG AGUACAGUAAGACAGGUAGCACCAGUCUGACGUUUGUCG UCAGUGCCUGGACGUGCAGU | 87 |
| R8c6_1-20 | GGG UACAGUAAGACACGUAGCACCAGUCUGACGUUUGUCG UCAGUGCCUGGACGUGCAGU | 88 |
| R8c6_1-21 | GGG ACAGUAAGACACGUAGCACCAGUCUGACGUUUGUCG UCAGUGCCUGGACGUGCAGU | 89 |

(2) Ability to Bind to His-tag-added HMGB1

Figure 6:
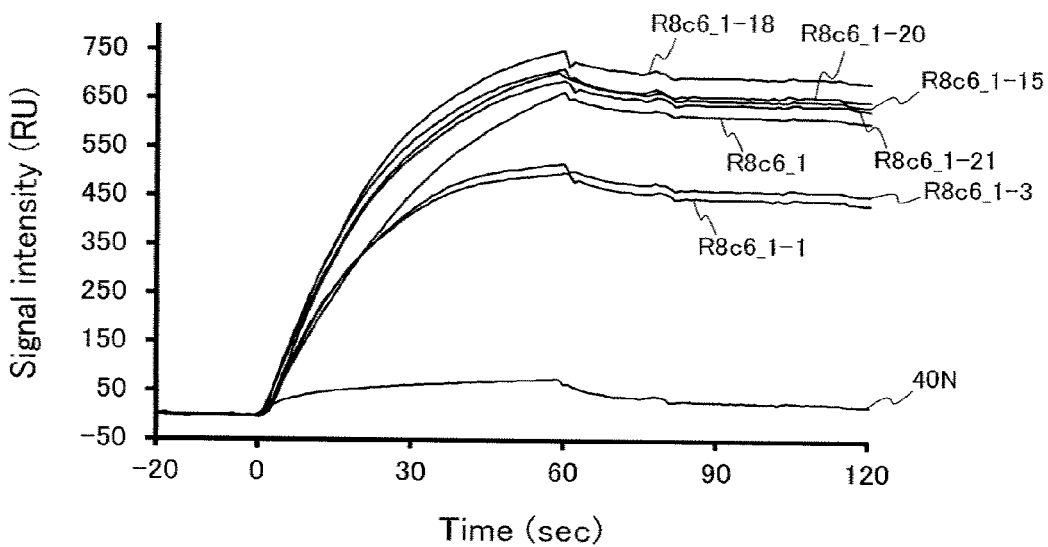
FIG. 6 is a graph showing the ability of each RNA aptamer to bind to His-tag-added HMGB1 in Example 3 of the present invention.

An analysis of ability to bind to His-tag-added HMGB1 was carried out in the same manner as in (2) above of the aforementioned Example 1 except that the aforementioned RNA aptamers were used, the concentration of the aforementioned His-tag-added HMGB1 was 635 nmol/L, and the injection time of the aforementioned His-tag-added HMGB1 was 60 seconds. Also, an analysis was carried on the aforementioned 40N as a comparative example in the same manner. FIG. 6 shows the results.

FIG. 6 is a graph showing the ability of each RNA aptamer to bind to the aforementioned His-tag-added HMGB1. In the graph of FIG. 6, the vertical axis indicates the signal intensity (RU) measured by the aforementioned BIACORE (registered trademark) X, and the horizontal axis indicates the analysis time (sec). In the horizontal axis, the time from −20 sec to 0 sec is the time of pre-washing with the aforementioned running buffer, the time at 0 sec is when the injection of the aforementioned His-tag-added HMGB1 was started, the time from 0 sec to 60 sec is the injection time of the aforementioned His-tag-added HMGB1, and the time from 60 sec onward is the time of washing with the aforementioned running buffer.

As shown in FIG. 6, the RNA aptamers prepared by shortening R8c6_1 each exhibited an increase in signal intensity, and it was thus found that the RNA aptamers were bound to the aforementioned HMGB1. In particular, R8c6_1-15, 8c6_1, 2'F-R 8c6_1-1, 2'F-R &6_1-4, 2'F-R8c6_1-15, 2'F-R8c6_1-18, 2'F-R8c6_1-21. Moreover, fluorinated 40N (2'F-40N) was prepared by fluorinating the cytosine nucleotide residue and the uracil nucleotide residue of the aforementioned 40N, and used as a comparative example (the same also applies below).
(2) Ability to Bind to His-tag-added HMGB1

Figure 7:
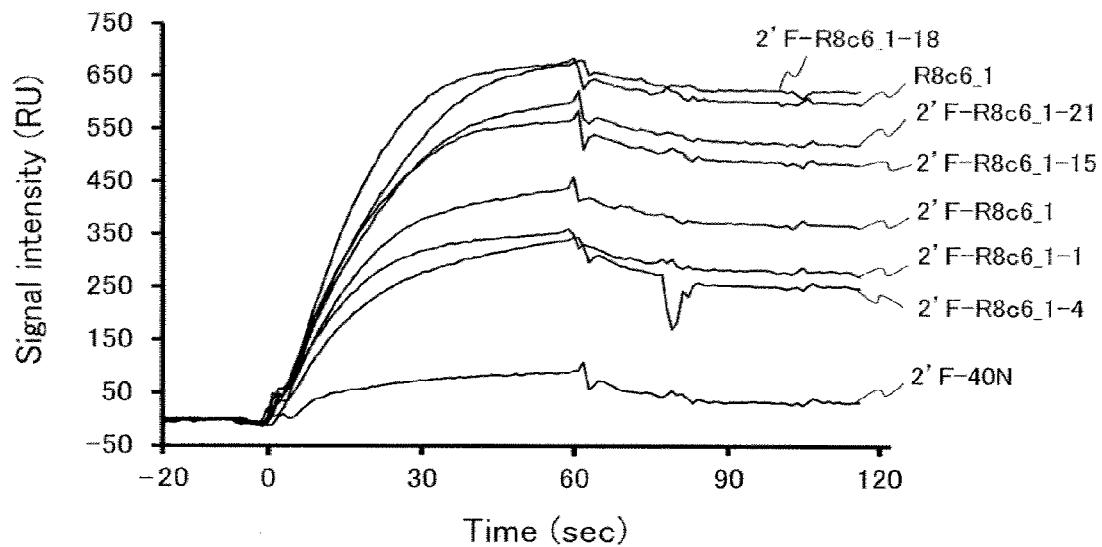
FIG. 7 is a graph showing the ability of each RNA aptamer to bind to His-tag-added HMGB1 in Example 4 of the present invention.

An analysis of ability to bind to His-tag-added HMGB1 was carried out in the same manner as in (2) above of the aforementioned Example 1 except that the aforementioned fluorinated RNA aptamers were used, the concentration of His-tag-added HMGB1 was 200 nmol/L, and the injection time of the aforementioned His-tag-added HMGB1 was 60 seconds. Also, an analysis was carried out in the same manner on the aforementioned 2'F-40N and unmodified R8c6_1 that was not fluorinated. FIG. 7 shows the results.

FIG. 7 is a graph showing the ability of each fluorinated RNA aptamer to bind to the aforementioned HMGB1. In the graph of FIG. 7, the vertical axis indicates the signal intensity (RU) measured by the aforementioned BIACORE (registered trademark) X, and the horizontal axis indicates the analysis time (sec). In the horizontal axis, the time from −20 sec to 0 sec is the time of pre-washing with the aforementioned running buffer, the time at 0 sec is when the injection of the aforementioned HMGB1 was started, the time from 0 sec to 60 sec is the injection time of the aforementioned HMGB1, and the time from 60 sec onward is the time of washing with the aforementioned running buffer.

As shown in FIG. 7, the aforementioned fluorinated RNA aptamers prepared by shortening R8c6_1 each exhibited an increase in signal intensity, and it was thus found that the RNA aptamers were bound to the aforementioned HMGB1. In particular, 2'F-R8c6_1-18 demonstrated excellent binding ability comparable to unmodified R8c6_1. It is known that fluorinated RNA aptamers usually exhibit RNase resistance. Accordingly, the aforementioned fluorinated RNA aptamers having ability to bind to HMGB1 are unlikely to decompose, for example, even when administered into a living body, and it can therefore be said that the RNA aptamers are useful as, for example, pharmaceutical products or the like.

Example 5

R8c6_1 (SEQ ID NO. 74) and R8c6_1-18 (SEQ ID NO. 87), which is a shortened RNA aptamer thereof, were both fluorinated, and their ability to bind to HMGB1 was examined.

(1) RNA Aptamers

The aforementioned R8c6_1 and R8c6_1-18 RNA aptamers were both prepared according to a known nucleic acid synthesizing method using the aforementioned 2'-fluoro-CTP and the aforementioned 2'-fluoro-UTP, and used as fluorinated RNA aptamers of the example. The aforementioned fluorinated RNA aptamers have the same base sequences as those of R8c6_1 (SEQ ID NO. 74) and R8c6_1-18 (SEQ ID NO. 87) except that the cytosine nucleotide residue and the uracil nucleotide residue are fluorinated. The fluorinated RNA aptamers were respectively designated as 2'F-R8c6_1 and 2'F-R8c6_1-18.

(2) Ability to Bind to His-tag-added HMGB1

Figure 8:
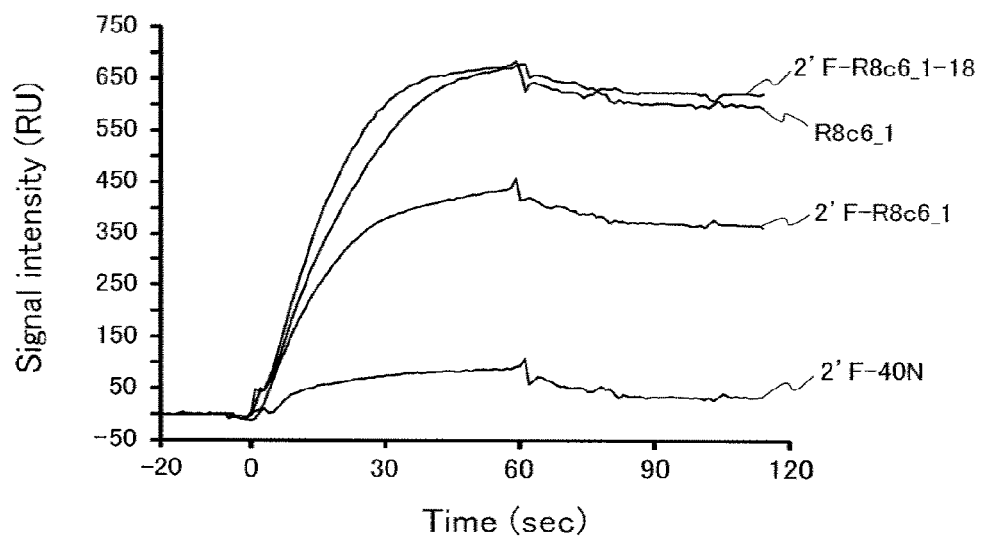
FIG. 8 is a graph showing the ability of each RNA aptamer to bind to His-tag-added HMGB1 in Example 5 of the present invention.

An analysis of ability to bind to His-tag-added HMGB1 was carried out in the same manner as in (2) above of the aforementioned Example 1 except that the aforementioned fluorinated RNA aptamers were used, the concentration of His-tag-added HMGB1 was 200 nmol/L, the concentration of NaCl in the aforementioned running buffer was 150 mmol/L, and the injection time of the aforementioned His-tag-added HMGB1 was 60 seconds. Also, an analysis was carried out in the same manner on the aforementioned 2'F-40N and unmodified R8c6_1 that was not fluorinated. FIG. 8 shows the results.

FIG. 8 is a graph showing the ability of each fluorinated RNA aptamer to bind to the aforementioned His-tag-added HMGB1. In the graph of FIG. 8, the vertical axis indicates the signal intensity (RU) measured by the aforementioned BIACORE (registered trademark) X, and the horizontal axis indicates the analysis time (sec). In the horizontal axis, the time from −20 sec to 0 sec is the time of pre-washing with the aforementioned running buffer, the time at 0 sec is when the injection of the aforementioned His-tag-added HMGB1 was started, the time from 0 sec to 60 sec is the injection time of the aforementioned His-tag-added HMGB1, and the time from 60 sec onward is the time of washing with the aforementioned running buffer.

As shown in FIG. 8, the aforementioned fluorinated RNA aptamers each exhibited an increase in signal intensity, and it was thus found that the RNA aptamers were bound to the aforementioned HMGB1. In particular, 2'F-R8c6_1-18 demonstrated excellent binding ability comparable to unmodified R8c6_1.

Example 6

Inhibition of binding between HMGB1 and a receptor TLR-2 by R8c6_1-18 (SEQ ID NO. 87) was examined.

(1) Pull-down Assay

Figure 9:
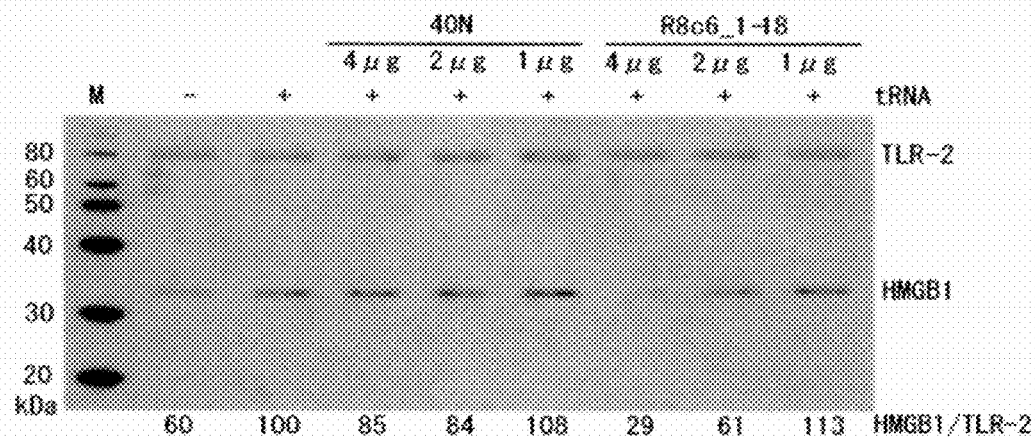
FIG. 9 is an image of a pull-down assay showing binding between HMGB1 and TLR-2 in Example 6 of the present invention.

TLR-2 in which His-tag was added to the N-terminus (His-tag-added TLR-2) was used. 2 μg of His-tag-added TLR-2, 2 μg of HMGB1, and a specific amount of R8c6_1-18 were added to 50 μL of a binding buffer, and this mixture was incubated at 4° C. for 20 min. R8c6_1-18 was added in amounts of 1 μg, 2 μg, and 4 μg. The aforementioned binding buffer had the same composition as the aforementioned running buffer, and 1 mg/mL of tRNA was added thereto or tRNA was not added thereto. 1 μL of $Co^{2+}$-bound agarose beads (trade name: BD TALON (registered trademark) Metal Affinity Resin, manufactured by BD Biosciences) was added to the aforementioned mixture, and the mixture was incubated at 4° C. for 20 min. After incubation, the aforementioned agarose beads were washed, and Western blotting was carried out using an anti-HMGB1 antibody (trade name: Rabbit polyclonal to HMGB1, manufactured by abcam). Also, an analysis was carried on the aforementioned 40N as a comparative example in the same manner. FIG. 9 shows the results.

FIG. 9 is an image of a pull-down assay showing binding between HMGB1 and TLR-2. In FIG. 9, tRNA "−" indicates the use of the aforementioned binding buffer to which tRNA was not added, and tRNA "+" indicates the use of the aforementioned binding buffer to which tRNA was added. In FIG. 9, from left, the lane "M" shows the results of a molecular weight marker, the lane "−" shows the results of an assay in which neither tRNA nor an RNA aptamer was added, the lane "+" shows the results of an assay in which tRNA was added and RNA aptamer was not added, the lanes "40N" show the respective results of assays in which 40N was added in amounts of 4 μg, 2 μg, and 1 μg, and the lanes "R8c6_1-18" show the respective results of assays in which R8c6_1-18 was added in amounts of 4 μg, 2 μg, and 1 μg. Regarding the results of each lane, the detected HMGB1 amounts were corrected with the TLR-2 amount, and values relative to the corrected value of the lane "+" are shown below the respective lanes, with the corrected value of the lane "+" being 100.

As shown in FIG. 9, in the case where 40N of the comparative example was added, the amount of HMGB1 did not change regardless of an increase in the amount of 40N added. In contrast, in the case where R8c6_1-18 was added, the amount of HMGB1 was decreased as the amount of R8c6_1-18 added was increased. It can be understood from these results that binding between HMGB1 and TLR-2 is inhibited by R8c6_1-18. Accordingly, it can be said that the HMGB1 binding nucleic acid molecule of the present invention is useful for, for example, treatment of a disease in which HMGB1 is involved.

Example 7

RNA aptamers were fluorinated, and their binding ability to HMGB1 was examined.

(1) RNA Aptamers

The RNA aptamers shown in Table 4 below were each prepared according to a known nucleic acid synthesizing method using the aforementioned 2'-fluoro-CTP and the aforementioned 2'-fluoro-UTP, and used as fluorinated RNA aptamers of the example. The aforementioned fluorinated RNA aptamers have base sequences as shown in Table 4 below but the cytosine nucleotide residue and/or the uracil nucleotide residue are/is fluorinated. The RNA aptamers in which the uracil nucleotide residue and the cytosine nucleotide residue were fluorinated were respectively designated as 2'F-CU-R 8c6_1, 2'F-CU-#06, 2'F-CU-CU#80, and 2'F-CU-R4_9068. The RNA aptamers in which only the cytosine nucleotide residue was fluorinated were respectively designated as 2'F-C-R 8c6_1, 2'F-C-#06, 2'F-C-#80, and 2'F-C-R4_9068. The RNA aptamers in which only the uracil nucleotide residue was fluorinated were respectively designated as 2'F-U-R 8c6_1, 2'F-U-#06, 2'F-U-#80, and 2'F-U-R4_9068.

RNA aptamers in which only the cytosine nucleotide residue was fluorinated, the term "2'F-U-modified" is for the results of RNA aptamers in which only the uracil nucleotide residue was fluorinated, and the term "non-modified" is for the results of unmodified RNA aptamers R8c6_1 and unmodified 40N.

Figure 10:
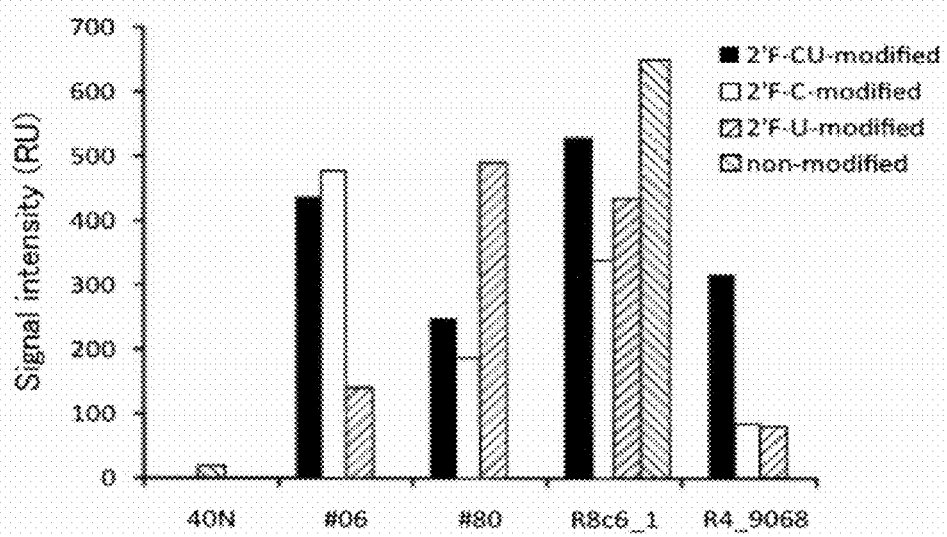
FIG. 10 is a graph showing the ability of each RNA aptamer to bind to His-tag-added HMGB1 in Example 7 of the present invention.

As shown in FIG. 10, the fluorinated RNA aptamers each exhibited a higher increase in signal intensity than the unmodified 40N of a comparative example, and it was thus found that the RNA aptamers were bound to the aforementioned HMGB1. In particular, 2'F-CU-R 8c6_1, 2'F-C-

TABLE 4

| Aptamer | Sequence | SEQ No. |
|---|---|---|
| R8c6_1 | GGGACGCUCACGUACGCUCA GAGUACAGUAAGACACGUAGCACCAGUCUGACGUUUGUCG UCAGUGCCUGGACGUGCAGU | 74 |
| # 06 | GGGACGCUCACGUACGCUCA UACACUGCACGCUCCGCUUUGAACAUCAAUGGAGGCCCUG UCAGUGCCUGGACGUGCAGU | 56 |
| # 80 | GGGACGCUCACGUACGCUCA CAUCUGAAUUUAAGCCACGUAGAACCAGGCCCUCCACGCG UCAGUGCCUGGACGUGCAGU | 67 |
| HMGB1R4_9068 | GGGACGCUCACGUACGCUCA UGAUAUUUAAAUUUGGCCGCGUUUAAAACAUCCCCUACGA UCAGUGCCUGGACGUGCAGU | 79 |
| HMGB1R4_2478 | GGGACGCUCACGUACGCUCA GAUUCCGUUGCCCUUCCGUUGAACUGUGCCAGGCUUUUUG UCAGUGCCUGGACGUGCAGU | 80 |

(2) Ability to Bind to His-tag-added HMGB1

An analysis of ability to bind to the aforementioned His-tag-added HMGB1 (manufactured by Sigma) was carried out in the same manner as in (2) above of the aforementioned Example 1 except that the aforementioned fluorinated RNA aptamers were used, the concentration of the aforementioned His-tag-added HMGB1 was 200 nmol/L, the concentration of NaCl in the aforementioned running buffer was 150 mmol/L, and the injection time of the aforementioned His-tag-added HMGB1 was 60 seconds. Also, an analysis was carried out in the same manner on unmodified R8c6_1 that was not fluorinated. Also, an analysis was carried in the same manner as a comparative example on the aforementioned 40N that was not fluorinated. FIG. 10 shows the results.

FIG. 10 is a graph showing the ability of each fluorinated RNA aptamer to bind to the aforementioned His-tag-added HMGB1. In the graph of FIG. 10, the vertical axis indicates the signal intensity (RU) measured by the aforementioned BIACORE (registered trademark) X at the end of His-tag-added HMGB1 injection. The aforementioned graph shows from left the results of 40N, #06, #80, R8c6_1, and HMGB1R4_9068. In the graph, the term "2'F-CU-modified" is for the results of RNA aptamers in which both the cytosine nucleotide residue and the uracil nucleotide residue were fluorinated, the term "2'F-C-modified" is for the results of R8c6_1, and 2'F-U-R 8c6_1 demonstrated excellent binding ability, and especially 2'F-CU-8c6_1 demonstrated binding ability comparable to unmodified R8c6_1.

Example 8

The secondary structures of R8c6_1 (SEQ ID NO. 74) and R8c6_1-18 (SEQ ID NO. 87) were estimated. The secondary structures thereof are shown in FIG. 11.

Example 9

The RNA aptamer having R8c6_1 (SEQ ID NO. 74) was further shortened, and the ability to bind to HMGB1 was examined.
(1) RNA Aptamers The RNA aptamers shown in Tables 5 and 6 below were prepared according to a known nucleic acid synthesizing method, and used as RNA aptamers of the example.

TABLE 5

| Aptamer | Sequence | SEQ No. |
|---|---|---|
| R8c6_1 | GGGACGCUCACGUACGCUCA GAGUACAGUAAGACACGUAGCACCAGUCUGACGUUUGUCG UCAGUGCCUGGACGUGCAGU | 74 |
| R8c6_1-25 | GGG UAAGACACGUAGCACCAGUCUGACGUUUGUCG UCAGUGCCUGGACGUGCAGU | 90 |
| R8c6_1-30 | GGG CACGUAGCACCAGUCUGACGUUUGUCG UCAGUGCCUGGACGUGCAGU | 91 |
| R8c6_1-34CC | GGG UAGCACCAGUCUGACGUUUGUCG UCAGUGCCUGGACGUGC<u>CC</u> | 92 |
| R8c6_1-18 | GGG AGUACAGUAAGACACGUAGCACCAGUCUGACGUUUGUCG UCAGUGCCUGGACGUGCAGU | 87 |
| R8c6_1-18-S2 | GGG AGUACAGUAAGACACGUAGCACCAGUC G CGUUUGUCG C GUGCCUGGACGUGCAGU | 93 |
| R8c6_1-18-S4 | GGG AGUACAGUAAGACACGUAGCACCAGUC GUUUGUCG UGCCUGGACGUGCAGU | 94 |
| R8c6_1-18-S6 | GGG AGUACAGUAAGACACGUAGCACCAGU GUGCCUGGACGUGCAGU | 95 |

Figure 18:
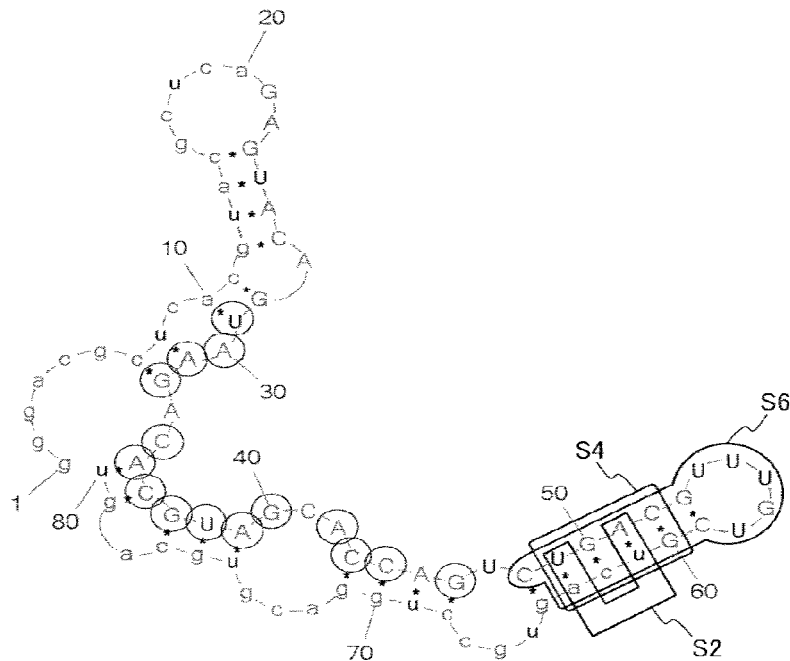
FIG. 18 is a diagram illustrating SEQ ID No. 74, and showing an estimated secondary structure of an RNA aptamer R8c6_1 of the present invention.
Figure 19:
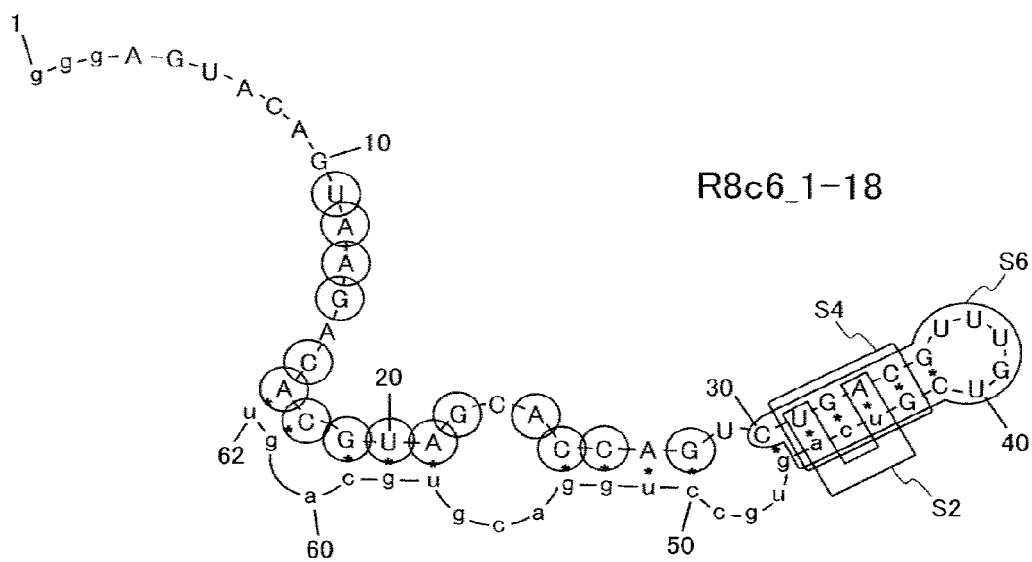
FIG. 19 is a diagram illustrating SEQ ID No. 87, and showing an estimated secondary structure of an RNA aptamer R8c6_1-18 of the present invention.

The RNA aptamers of Table 5 are aptamers prepared by shortening R8c6_1. FIG. 18 shows a schematic illustration of an estimated secondary structure of R8c6_1, and FIG. 19 shows that of R8c6_1-18. In the aforementioned Table 5, R8c6_1-25 and R8c6_1-18 are base sequences each prepared by deleting a 5' side region from R8c6_1. R8c6_1-18-S2, R8c6_1-18-S4, and R8c6_1-18-S6 are base sequences each prepared by deleting a 5' side region from R8c6_1 as with R8c6_1-18 and further deleting an S2, S4, or S6 region shown in FIG. 18. In the estimated secondary structure of R8c6_1, S2 and S4 are base-pair regions each forming a stem structure, and S6 is a region forming a stem-loop structure.

intensity, and it was thus found that the RNA aptamers were bound to the aforementioned HMGB1. In particular, R8c6_1-18-S2 and R8c6_1-25 demonstrated binding ability superior to R8c6_1.

TABLE 6

| Aptamer | Sequence | | SEQ No. |
|---|---|---|---|
| R8c6_1-25 | GGG UAAGACACGUAGCACCAGUCUGACGUUUGUCG | UCAGUGCCUGGACGUGCAGU | 90 |
| R8c6_1-25-S6 | GGG UAAGACACGUAGCACCAGU | GUGCCUGGACGUGCAGU | 100 |
| R8c6_1-25-S6A | GGG UAAG CACGUAGCACCAGU | GUGCCUGGACGUGCAGU | 103 |
| R8c6_1-25-S6A2 | GGG UAAGACACGUAGCACC GU | GUGCC GGACGUGCAGU | 104 |
| R8c6_1-25-S6A3 | GGG UAAGACACGUAGCACCAGU | GUGCCUGGACGUGC GU | 105 |
| R8c6_1-25-S6C | GGG UAAGACACGUAG ACCAGU | GUGCCUGGACGUGCAGU | 106 |
| R8c6_1-25-S6C2 | GGG UAAGACACGUAGCACCAGU | GUGCCUGGA GUGCAGU | 107 |
| R8c6_1-25-S8 | GGG UAAGACACGUAGCACCAG | UGCCUGGACGUGCAGU | 112 |
| R8c6_1-26-S6 | GGG AAGACACGUAGCACCAGU | GUGCCUGGACGUGCAGU | 101 |
| R8c6_1-27-S6 | GGG AGACACGUAGCACCAGU | GUGCCUGGACGUGCAGU | 102 |

The RNA aptamers of Table 6 above are aptamers prepared by further shortening R8c6_1-25-S6 of Table 5 above. FIG. 20 shows a schematic illustration of an estimated secondary structure of R8c6_1-25S6. R8c6_1-25-S6A2, R8c6_1-25-S6C, and R8c6_1-25-8 are base sequences prepared by deleting the A2, C, and S8 regions shown in FIG. 20, respectively. The R8c6_1-26-S6 sequences are base sequences each prepared by deleting one base on the 5' side of R8c6_1-25-S6.

(2) Ability to Bind to His-tag-added HMGB1

Figure 12:
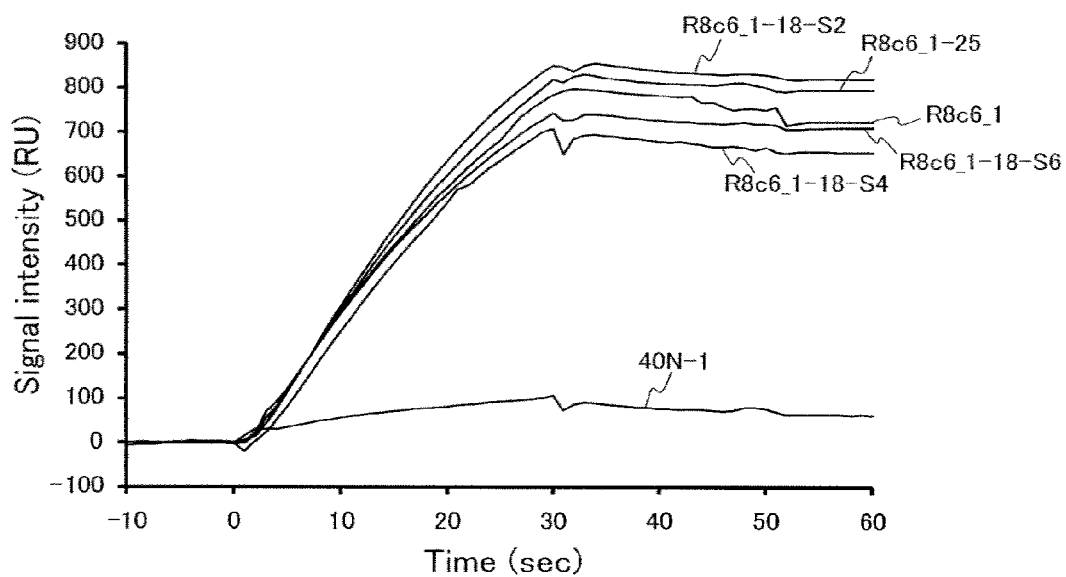
FIG. 12 is a graph showing the ability of each RNA aptamer to bind to His-tag-added HMGB1 in Example 9 of the present invention.
Figure 13:
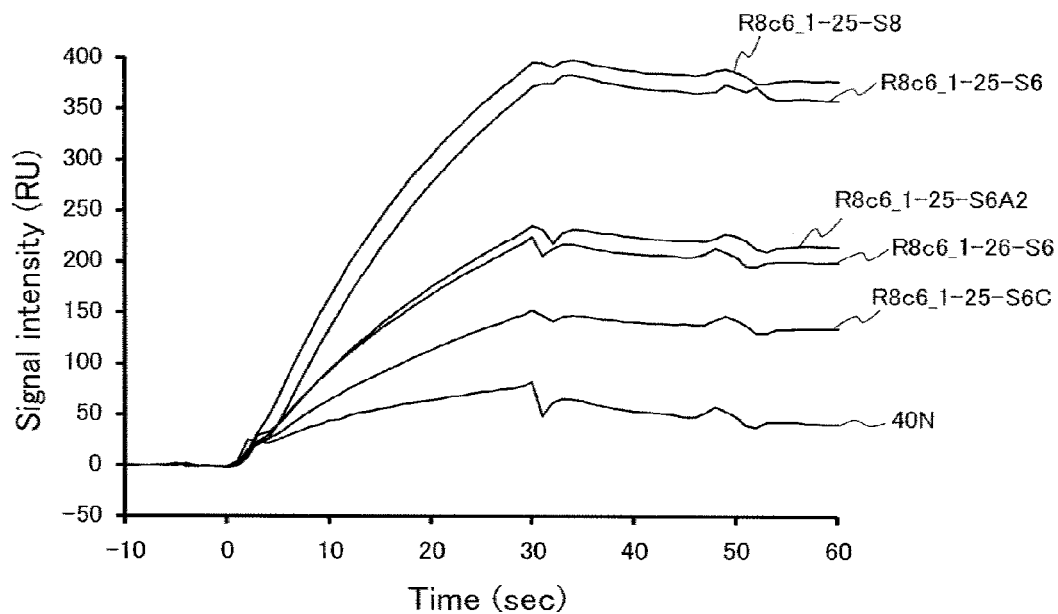
FIG. 13 is a graph showing the ability of each RNA aptamer to bind to His-tag-added HMGB1 in Example 9 of the present invention.

An analysis of ability to bind to His-tag added HMGB1 was carried out in the same manner as in (2) above of the aforementioned Example 1 except that the aforementioned RNA aptamers were used, and the concentration of the aforementioned His-tag-added HMGB1 was 160 nmol/L. Also, an analysis was carried on the aforementioned 40N as a comparative example in the same manner. FIGS. 12 and 13 show the results.

FIGS. 12 and 13 are graphs both showing the ability of each RNA aptamer to bind to the aforementioned His-tag-added HMGB1. In the graphs of FIGS. 12 and 13, the vertical axis indicates the signal intensity (RU) measured by the aforementioned BIACORE (registered trademark) X, and the horizontal axis indicates the analysis time (sec). In the horizontal axis, the time from −10 sec to 0 sec is the time of pre-washing with the aforementioned running buffer, the time at 0 sec is when the injection of the aforementioned His-tag-added HMGB1 was started, the time from 0 sec to 30 sec is the injection time of the aforementioned His-tag-added HMGB1, and the time from 30 sec onward is the time of washing with the aforementioned running buffer.

As shown in FIG. 12, the RNA aptamers prepared by shortening R8c6_1 each exhibited an increase in signal Moreover, as shown in FIG. 13, the RNA aptamers prepared by further shortening R8c6_1-25, which is an RNA aptamer prepared by shortening R8c6_1, each exhibited an increase in signal intensity, and it was thus found that the RNA aptamers were bound to the aforementioned HMGB1.

Example 10

RNA aptamers were fluorinated, and their binding ability to HMGB1 was examined.

(1) RNA Aptamers

The RNA aptamers shown in Table 7 below were each prepared according to a known nucleic acid synthesizing method using the aforementioned 2'-fluoro-CTP and the aforementioned 2'-fluoro-UTP, and used as fluorinated RNA aptamers of the example. The aforementioned fluorinated RNA aptamers have base sequences as shown in Table 7 above but the cytosine nucleotide residue and the uracil nucleotide residue are fluorinated. The RNA aptamers in which the uracil nucleotide residue and the cytosine nucleotide residue were fluorinated were respectively designated as 2'F-R8c6_1-18-S6, 2'F-R8c6_1-25, 2'F-R8c6_1-25-S6, 2'F-R8c6_1-25-S6A, 2'F-R8c6_1-25-S6A2, 2'F-R8c6_1-25-S6C, 2'F-R8c6_1-25-S6C, 2'F-R8c6_1-25-S6C2, and 2'F-R8c6_1-25-S8. Also, the aforementioned 40N was fluorinated in the same manner using the aforementioned 2'-fluoro-CTP and the aforementioned 2'-fluoro-UTP.

TABLE 7

| Aptamer | Sequence | | SEQ No. |
|---|---|---|---|
| R8c6_1-18-S6 | GGG AGUACAGUAAGACACGUAGCACCAGU | GUGCCUGGACGUGCAGU | 95 |
| R8c6_1-25 | GGG UAAGACACGUAGCACCAGUCUGACGUUUGUCG | UCAGUGCCUGGACGUGCAGU | 90 |

TABLE 7-continued

| Aptamer | Sequence | | SEQ No. |
|---|---|---|---|
| R8c6_1-26-S6 | GGG     AAGACACGUAGCACCAGU | GUGCCUGGACGUGCAGU | 101 |
| R8c6_1-25-S6A | GGG    UAAG CACGUAGCACCAGU | GUGCCUGGACGUGCAGU | 103 |
| R8c6_1-25-S6A2 | GGG    UAAGACACGUAGCACC GU | GUGCC GGACGUGCAGU | 104 |
| R8c6_1-25-S6A3 | GGG    UAAGACACGUAGCACCAGU | GUGCCUGGACGUGC GU | 105 |
| R8c6_1-25-S6C | GGG    UAAGACACGUAG ACCAGU | GUGCCUGGACGUGCAGU | 106 |
| R8c6_1-25-S6C2 | GGG    UAAGACACGUAGCACCAGU | GUGCCUGGA GUGCAGU | 107 |
| R8c6_1-25-S8 | GGG    UAAGACACGUAGCACCAG | UGCCUGGACGUGCAGU | 112 |

(2) Ability to Bind to His-tag-added HMGB1

Figure 14:
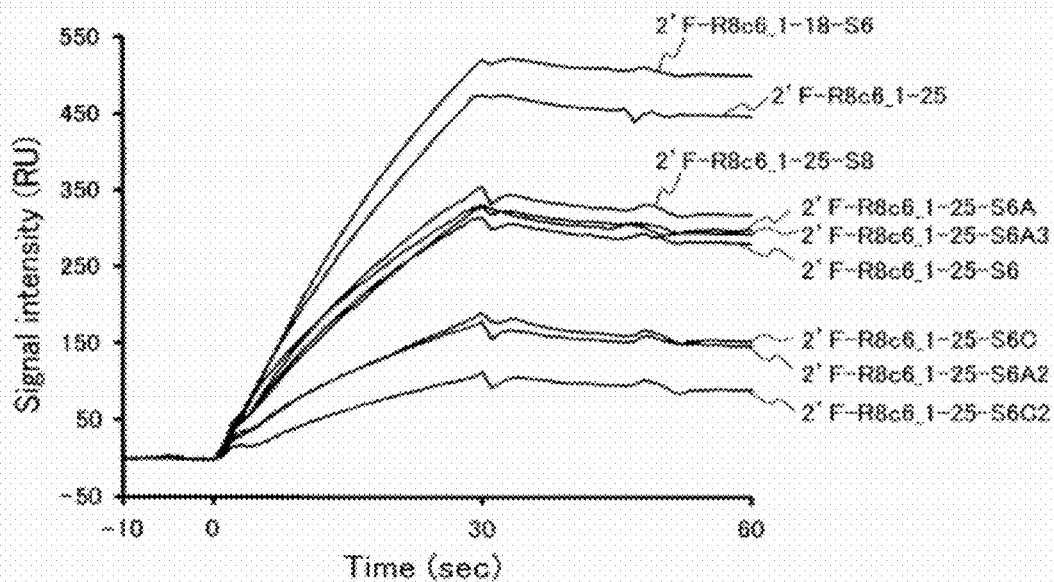
FIG. 14 is a graph showing the ability of each RNA aptamer to bind to His-tag-added HMGB1 in Example 10 of the present invention.

An analysis of ability to bind to His-tag added HMGB1 was carried out in the same manner as in (2) above of the aforementioned Example 1 except that the aforementioned RNA aptamers were used, and the concentration of the aforementioned His-tag-added HMGB1 was 150 nmol/L. FIG. 14 shows the results.

FIG. 14 is a graph showing the ability of each fluorinated RNA aptamer to bind to the aforementioned His-tag-added HMGB1. In the graph of FIG. 14, the vertical axis indicates the signal intensity (RU) measured by the aforementioned BIACORE (registered trademark) X, and the horizontal axis indicates the analysis time (sec). In the horizontal axis, the time from −10 sec to 0 sec is the time of pre-washing with the aforementioned running buffer, the time at 0 sec is when the injection of the aforementioned His-tag-added HMGB1 was started, the time from 0 sec to 30 sec is the injection time of the aforementioned His-tag-added HMGB1, and the time from 30 sec onward is the time of washing with the aforementioned running buffer.

As shown in FIG. 14, the aforementioned shortened fluorinated RNA aptamers each exhibited an increase in signal intensity, and it was thus found that the RNA aptamers were bound to the aforementioned HMGB1. In particular, 2'F-R8c6_1-18-S6 and 2'-R8c6_1-25 demonstrated excellent binding ability.

Example 11

The RNA aptamer having R8c6_1 (SEQ ID NO. 74) was further shortened, and the ability to bind to HMGB1 was examined.

(1) RNA Aptamers

The RNA aptamers shown in Table 8 below were each prepared according to a known nucleic acid synthesizing method, and used as RNA aptamers of the example.

TABLE 8

| Aptamer | Sequence | | SEQ No. |
|---|---|---|---|
| R8c6_1-18 | GGG AGUACAGUAAGACACGUAGCACCAGUCUGACGUUUGUCG UCAGUGCCUGGACGUGCAGU | | 87 |
| R8c6_1-18-S6 | GGG AGUACAGUAAGACACGUAGCACCAGU | GUGCCUGGACGUGCAGU | 95 |
| R8c6_1-21-S6 | GGG     ACAGUAAGACACGUAGCACCAGU | GUGCCUGGACGUGCAGU | 96 |
| R8c6_1-22-S6 | GGG      CAGUAAGACACGUAGCACCAGU | GUGCCUGGACGUGCAGU | 97 |
| R8c6_1-23-S6 | GGG       AGUAAGACACGUAGCACCAGU | GUGCCUGGACGUGCAGU | 98 |
| R8c6_1-24-S6 | GGG        GUAAGACACGUAGCACCAGU | GUGCCUGGACGUGCAGU | 99 |
| R8c6_1-21-S8 | GGG     ACAGUAAGACACGUAGCACCAG | UGCCUGGACGUGCAGU | 108 |
| R8c6_1-22-S8 | GGG      CAGUAAGACACGUAGCACCAG | UGCCUGGACGUGCAGU | 109 |
| R8c6_1-23-S8 | GGG       AGUAAGACACGUAGCACCAG | UGCCUGGACGUGCAGU | 110 |
| R8c6_1-24-S8 | GGG        GUAAGACACGUAGCACCAG | UGCCUGGACGUGCAGU | 111 |
| R8c6_1-25-S8CA | GGG         UAAGACACGUAGAACCAG | UGACUGGAAGUGCAGU | 113 |

The RNA aptamers of Table 8 are aptamers prepared by shortening R8c6_1. R8c6_1-21-S6, R8c6_1-22-S6, R8c6_1-23-S6, and R8c6_1-24-S6 are base sequences were each prepared by deleting a 5' side region from the aforementioned R8c6_1-18-S6. R8c6_1-21-S8, R8c6_1-22-S8, R8c6_1-23-S8, and R8c6_1-24-S8 have the same 5' side sequence as R8c6_1-21-S6, R8c6_1-22-S6, R8c6_1-23-S6, and R8c6_1-24-S6, respectively, and are base sequences in which the same region as the aforementioned S8 shown in the aforementioned FIG. 20 is deleted.

(2) Ability to Bind to His-tag-added HMGB1

Figure 15:
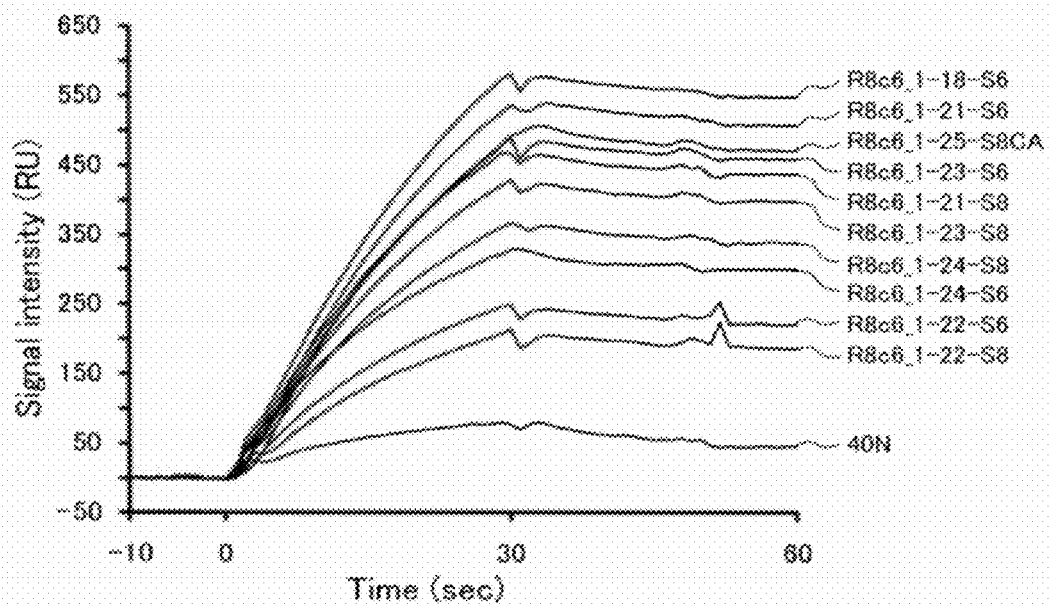
FIG. 15 is a graph showing the ability of each RNA aptamer to bind to His-tag-added HMGB1 in Example 11 of the present invention.

An analysis of ability to bind to His-tag added HMGB1 was carried out in the same manner as in (2) above of the aforementioned Example 1 except that the aforementioned RNA aptamers were used, and the concentration of the aforementioned His-tag-added HMGB1 was 150 nmol/L. Also, an analysis was carried on the aforementioned 40N as a comparative example in the same manner. FIG. 15 shows the results.

FIG. 15 is a graph showing the ability of each RNA aptamer to bind to the aforementioned His-tag-added HMGB1. In the graph of FIG. 15, the vertical axis indicates the signal intensity (RU) measured by the aforementioned BIACORE (registered trademark) X, and the horizontal axis indicates the analysis time (sec). In the horizontal axis, the time from −10 sec to 0 sec is the time of pre-washing with the aforementioned running buffer, the time at 0 see is when the injection of the aforementioned His-tag-added HMGB1 was started, the time from 0 sec to 30 sec is the injection time of the aforementioned His-tag-added HMGB1, and the time from 30 sec onward is the time of washing with the aforementioned running buffer.

As shown in FIG. 15, the RNA aptamers prepared by shortening R8c6_1 each exhibited an increase in signal intensity, and it was thus found that the RNA aptamers were bound to the aforementioned HMGB1.

Example 12

RNA aptamers were fluorinated, and their binding ability to HMGB1 was examined.
(1) RNA Aptamers
The RNA aptamers shown in Tables 9 and 10 below were each prepared according to a known nucleic acid synthesizing method using the aforementioned 2'-fluoro-CTP and the aforementioned 2'-fluoro-UTP, and used as fluorinated RNA aptamers of the example. The aforementioned fluorinated RNA aptamers have base sequences as shown in the aforementioned Tables 9 and 10 above but the cytosine nucleotide residue and the uracil nucleotide residue are fluorinated. The RNA aptamers in which the uracil nucleotide residue and the cytosine nucleotide residue were fluorinated were respectively designated as 2'F-R8c6_1-21-S6, 2'F-R8c6_1-22-S6, 2'F-R8c6_1-23-S6, 2'F-R8c6_1-24-S6, 2'F-R8c6_1-25-S6, 2'F-R8c6_1-26-S6, 2'F-R8c6_1-27-S6, 2'F-R8c6_1-21-S8, 2'F-R8c6_1-22-S8, 2'F-R8c6_1-23-S8, 2'F-R8c6_1-24-S8, 2'F-R8c6_1-25-S8, and 2'F-R8c6_1-25-S8CA.

TABLE 9

| Aptamer | Sequence | SEQ No. |
|---|---|---|
| R8c6_1-21-S6 | GGG ACAGUAAGACACGUAGCACCAGU GUGCCUGGACGUGCAGU | 96 |
| R8c6_1-22-S6 | GGG CAGUAAGACACGUAGCACCAGU GUGCCUGGACGUGCAGU | 97 |
| R8c6_1-23-S6 | GGG AGUAAGACACGUAGCACCAGU GUGCCUGGACGUGCAGU | 98 |
| R8c6 1-24-S6 | GGG GUAAGACACGUAGCACCAGU GUGCCUGGACGUGCAGU | 99 |
| R8c6_1-25-S6 | GGG UAAGACACGUAGCACCAGU GUGCCUGGACGUGCAGU | 100 |
| R8c6_1-26-S6 | GGG AAGACACGUAGCACCAGU GUGCCUGGACGUGCAGU | 101 |
| R8c6_1-27-S6 | GGG AGACACGUAGCACCAGU GUGCCUGGACGUGCAGU | 102 |

TABLE 10

| Aptamer | Sequence | SEQ No. |
|---|---|---|
| R8c6_1-21-S8 | GGG ACAGUAAGACACGUAGCACCAG UGCCUGGACGUGCAGU | 108 |
| R8c6_1-22-S8 | GGG CAGUAAGACACGUAGCACCAG UGCCUGGACGUGCAGU | 109 |
| R8c6_1-23-S8 | GGG AGUAAGACACGUAGCACCAG UGCCUGGACGUGCAGU | 110 |
| R8c6_1-24-S8 | GGG GUAAGACACGUAGCACCAG UGCCUGGACGUGCAGU | 111 |
| R8c6_1-25-S8 | GGG UAAGACACGUAGCACCAG UGCCUGGACGUGCAGU | 112 |
| R8c6_1-25-S8CA | GGG UAAGACACGUAG<u>A</u>ACCAG UG<u>A</u>CUGGA<u>A</u>GUGCAGU | 113 |

Figure 16:
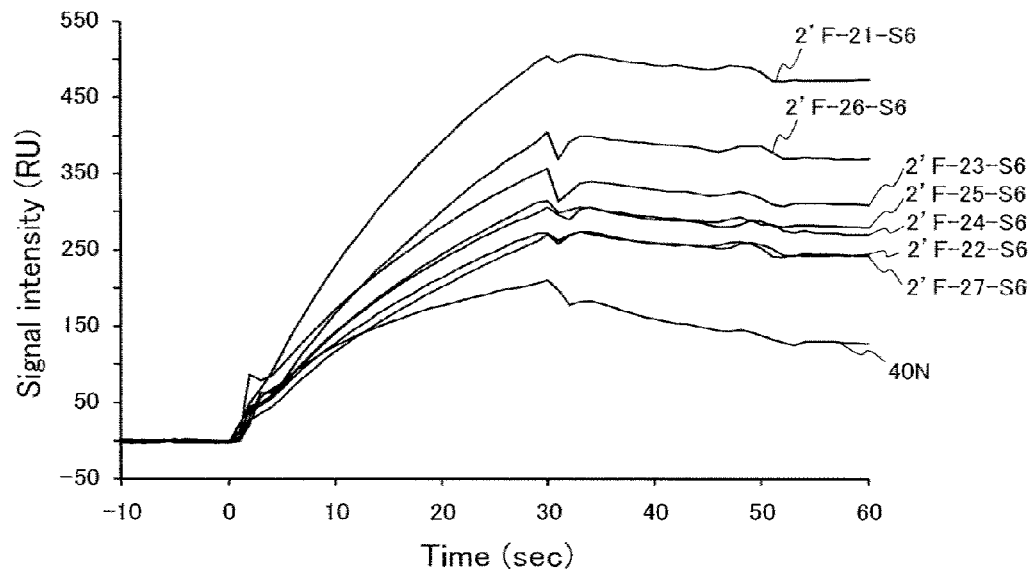
FIG. 16 is a graph showing the ability of each RNA aptamer to bind to His-tag-added HMGB1 in Example 12 of the present invention.
Figure 17:
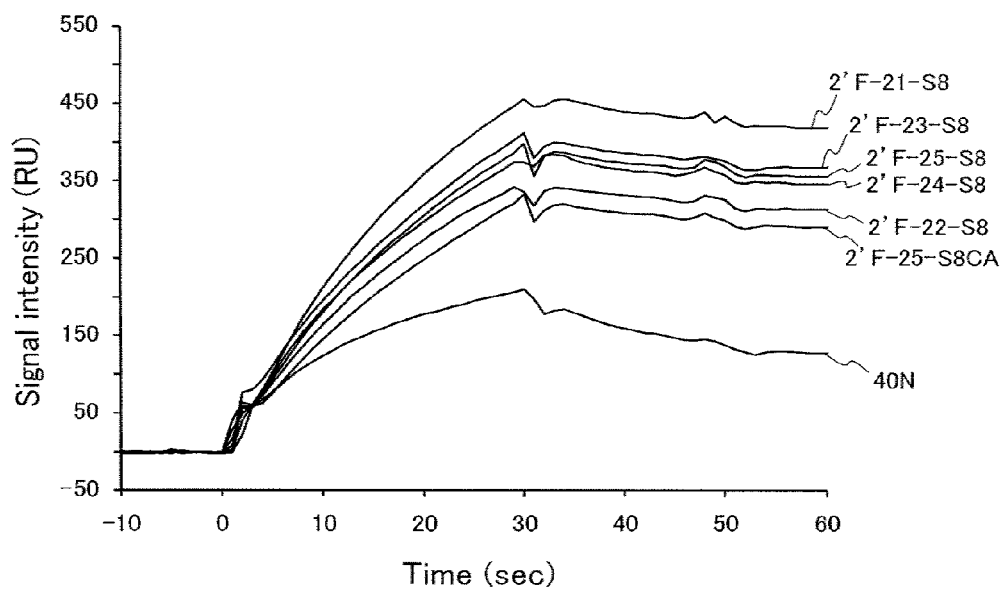
FIG. 17 is a graph showing the ability of each RNA aptamer to bind to His-tag-added HMGB1 in Example 12 of the present invention.

(2) Ability to Bind to His-tag-added HMGB1
An analysis of ability to bind to His-tag added HMGB1 was carried out in the same manner as in (2) above of the aforementioned Example 1 except that the aforementioned RNA aptamers were used, and the concentration of the aforementioned His-tag-added HMGB1 was 150 nmol/L. Also, an analysis was carried in the same manner on the aforementioned 40N that was unmodified as a comparative example. FIGS. 16 and 17 show the results. In FIGS. 16 and 17, "R8c6_1" is omitted from the name of each RNA aptamer.

FIGS. 16 and 17 are graphs showing the ability of each fluorinated RNA aptamer to bind to the aforementioned His-tag-added HMGB1. In the graphs of FIGS. 16 and 17, the vertical axis indicates the signal intensity (RU) measured by the aforementioned BIACORE (registered trademark) X, and the horizontal axis indicates the analysis time (sec). In the horizontal axis, the time from −10 sec to 0 sec is the time of pre-washing with the aforementioned running buffer, the time at 0 sec is when the injection of the aforementioned His-tag-added HMGB1 was started, the time from 0 sec to 30 sec is the injection time of the aforementioned His-tag-added HMGB1, and the time from 30 sec onward is the time of washing with the aforementioned running buffer.

As shown in FIGS. 16 and 17, the aforementioned shortened RNA aptamers each exhibited an increase in signal intensity, and it was thus found that the RNA aptamers were bound to the aforementioned HMGB1. In particular, 2'F-R8c6_1-21-S6 and 2'F-R8c6_1-21-S8 demonstrated excellent binding ability.

Example 13

An in reaction between an RNA aptamer R8c6_1-18-S6 (SEQ ID NO. 95) and HMGB1 was examined by the ELISA method.

An anti-his antibody (trade name: Penta-His Antibody, manufactured by QIAGEN) was diluted so as to attain 4 ug/mL using a carbonic acid buffer (pH 9.0). This antibody dilution was dispensed into each well of a 96-well plate (trade name: 96-well ELISA plate, manufactured by Asahi Techno Glass Corporation) in an amount of 50 μL per well and left to stand still at room temperature for 2 hours. Moreover, 1% BSA/TBS was dispensed into each well of the aforementioned plate in an amount of 50 μL per well and left to stand still over night. The aforementioned TBS was composed of 20 mmol/L Tris-HCl (pH 7.6) and 0.9% NaCl. In this manner, blocking treatment of the aforementioned plate was carried out. The wells of the aforementioned plate that had undergone blocking treatment were washed 3 times with 200 μL of a buffer. The aforementioned buffer were composed of 10 mmol/L HEPES, 500 mmol/L NaCl, 0.1 mmol/L $MgCl_2$, and 0.1% Triton X-100 (registered trademark), and the pH thereof was 7.2.

HMGB1 (trade name: HMG-1, manufactured by Sigma) was diluted with a buffer as mentioned above but that contained tRNA, so as to attain specific concentrations (1 μg/mL and 2 μg/mL), thus giving the aforementioned HMGB1 dilutions.

On the other hand, the aforementioned RNA aptamer was diluted with the aforementioned buffer, and the aforementioned RNA aptamer dilution was heat-treated at 95° C. for 5 minutes and then cooled to room temperature. Then, the aforementioned RNA aptamer dilution was mixed with an RNase inhibitor (trade name: RNase Inhibitor, manufactured by TOYOBO) and biotinylated deoxythymidine, thus giving an RNA aptamer mixture. As the aforementioned biotinylated deoxythymidine, 20-base-long deoxythymidine in which the 5' end was biotinylated was used. In the aforementioned RNA aptamer mixture, the concentration of the aforementioned RNA aptamer was 10 μg/mL or 20 μg/mL. Moreover, the aforementioned RNA aptamer mixture was set such that 50 μL thereof (i.e., one well) contained 0.2 μL of the aforementioned RNase inhibitor and 0.2 μL of the aforementioned biotinylation deoxythymidine.

Then, 50 μL of the aforementioned HMGB1 dilution was dispensed into each well of the aforementioned plate after the aforementioned washing, and the plate was left to stand still at 4° C. for 2 hours and then washed with 200 μL of the aforementioned buffer 3 times. Next, 50 μL of the aforementioned RNA aptamer mixture was further dispensed into each of the aforementioned wells, and a reaction was carried out at 4° C. for 2 hours. The ratios of the concentration of the aforementioned HMGB1 dilution (50 μL) to the concentration of the aforementioned RNA aptamer mixture (50 μL) added to each of the aforementioned wells were 1:20, 2:20, 1:10, and 2:10.

Figure 21:
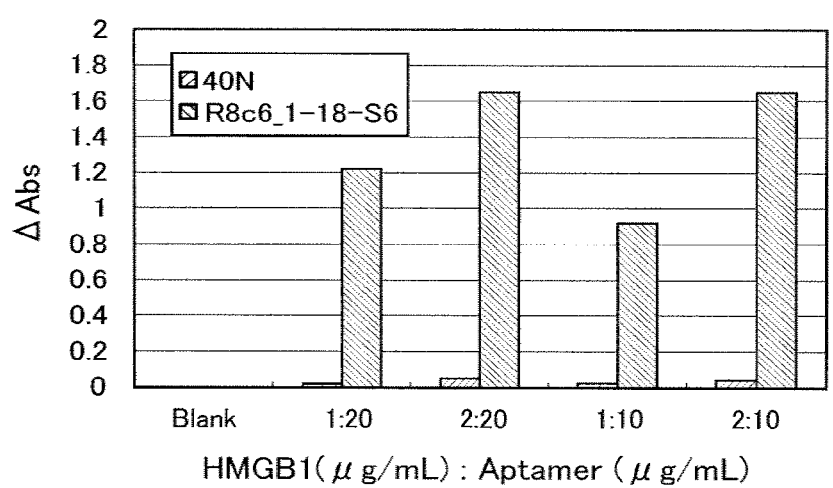
FIG. 21 is a graph showing an interaction between HMGB1 and an RNA aptamer in Example 13 of the present invention.

Then, avidin-added HRP (trade name: Streptavidin-Biotinylated Horseradish Peroxidase Complex, manufactured by GE Healthcare) was diluted 1000-fold with the aforementioned buffer and dispensed into each well in an amount of 50 ul, and a reaction was carried out at 4° C. for 1 hour. The aforementioned plate was washed 3 times with 200 μL of the aforementioned buffer, and TMB (trade name: 1-Srep™ Ultra TMB-ELISA, manufactured by Thermo Scientific) at ordinary temperature was dispensed into each well in an amount of 100 uL. The aforementioned plate was left to stand still at room temperature for 30 min while being shielded from light. 100 uL of 2 mol/L sulfuric acid was dispensed into each well to terminate the reaction. Then, the absorbance of each well at 450 nm was measured. In addition, as a control example, processing was performed in the same manner except that no RNA aptamer was added, and absorbance was measured. FIG. 21 shows the results.

FIG. 21 is a graph showing an interaction between HMGB1 and the aforementioned RNA aptamer, with the vertical axis indicating absorbance. As shown in FIG. 21, since the absorbance indicating binding between HMGB1 and the aforementioned RNA aptamer was increased, it was confirmed that the aforementioned RNA aptamer binds to HMGB1. Moreover, increasing the concentration of HMGB1 relative to the concentration of the aforementioned RNA aptamer increased the aforementioned absorbance. Accordingly, the HMGB1 binding nucleic acid molecule of the present invention enables quantification of HMGB1.

So far, the present invention has been described in reference to embodiments and examples, but the present invention is not limited to the aforementioned embodiments and examples. Various modifications can be made to the configuration and detail of the present invention that can be understood by those skilled in the art within the scope of the present invention.

Industrial Applicability

For example, binding of the aptamer of the present invention to HMGB1 enables prevention and treatment of diseases such as those mentioned above that are caused by HMGB1. Moreover, with the aptamer of the present invention to HMGB1, for example, determining the presence or absence of binding to HMGB1 enables detection of HMGB1, and the aptamer can be used in elucidation of the functions of HMGB1. Therefore, the aptamer is also useful as a novel research tool.

The invention claimed is:

1. An HMGB1 binding nucleic acid molecule that can bind to HMGB1 protein, the nucleic acid molecule comprising:
the base sequence of SEQ ID NO: 74,
wherein the nucleic acid molecule has a dissociation constant for the HMGB1 protein of $5 \times 10^{-7}$ or less.

2. The HMGB1 binding nucleic acid molecule according to claim 1, comprising a modified nucleotide residue.

3. The HMGB1 binding nucleic acid molecule according to claim 2, wherein the modified nucleotide residue is at least one selected from the group consisting of methylated nucleotide residues, fluorinated nucleotide residues, aminated nucleotide residues, and thio-modified nucleotide residues.

4. The HMGB1 binding nucleic acid molecule according to claim 2, wherein the modified nucleotide residue is at least one of nucleotide residues having cytosine and nucleotide residues having uracil.

5. The HMGB1 binding nucleic acid molecule according to claim 2, wherein the modified nucleotide residue is a nucleotide residue in which a ribose residue is modified.

6. The HMGB1 binding nucleic acid molecule according to claim 1, having the total number of bases of 40 to 100 bases.

7. The HMGB1 binding nucleic acid molecule according to claim 1, having a stem-loop structure.

8. The HMGB1 binding nucleic acid molecule according to claim 5, wherein the nucleic acid molecule comprises a Y region of base sequences, an X region including the base sequence of SEQ ID NO: 74, and a Y' region of base sequences, and wherein a part of at least one of the Y region and the Y' region forms a double-strand with a part of the X region, thereby forming a stem-loop structure.

9. The HMGB1 binding nucleic acid molecule according to claim 5, wherein the nucleic acid molecule comprises a Y region of base sequences, an X region including the base sequence of SEQ ID NO: 74, and a Y' region of base sequences, and wherein at least one of the Y region and the Y' region internally forms a double-strand, thereby forming a stem-loop structure.

10. A composition comprising an HMGB1 binding nucleic acid molecule of claim 1.

11. The composition according to claim 10, further comprising a carrier.

12. An HMGB1 detection reagent for detecting HMGB1 protein, comprising an HMGB1 binding nucleic acid molecule of claim 1.

13. An HMGB1 binding nucleic acid molecule that can bind to HMGB1 protein, the nucleic acid molecule comprising:
the base sequence of SEQ ID NO: 74,
wherein the nucleic acid molecule has a dissociation constant for the HMGB1 protein of $5 \times 10^{-7}$ or less,
wherein the nucleic acid molecule comprises a modified nucleotide residue selected from the group consisting of methylated nucleotide residues, fluorinated nucleotide residues, aminated nucleotide residues, and thio-modified nucleotide residues,
wherein the nucleic acid molecule comprises a total number of bases of 40 to 100 bases, and
wherein the nucleic acid molecule comprises a stem-loop structure.

* * * * *

SEQUENCE LISTING

```
<160> NUMBER OF SEQ ID NOS: 115

<210> SEQ ID NO 1
<211> LENGTH: 22
<212> TYPE: RNA
<213> ORGANISM: Artificial
<220> FEATURE:
<223> OTHER INFORMATION: aptamer

<400> SEQUENCE: 1
mmhbuaagmc acguagmacc ag                                              22

<210> SEQ ID NO 2
```

```
<211> LENGTH: 22
<212> TYPE: RNA
<213> ORGANISM: Artificial
<220> FEATURE:
<223> OTHER INFORMATION: aptamer

<400> SEQUENCE: 2
accguaagac acguagaacc ag                                                  22

<210> SEQ ID NO 3
<211> LENGTH: 22
<212> TYPE: RNA
<213> ORGANISM: Artificial
<220> FEATURE:
<223> OTHER INFORMATION: aptamer

<400> SEQUENCE: 3
aauuuaagcc acguagaacc ag                                                  22

<210> SEQ ID NO 4
<211> LENGTH: 22
<212> TYPE: RNA
<213> ORGANISM: Artificial
<220> FEATURE:
<223> OTHER INFORMATION: aptamer

<400> SEQUENCE: 4
acaguaagac acguagcacc ag                                                  22

<210> SEQ ID NO 5
<211> LENGTH: 22
<212> TYPE: RNA
<213> ORGANISM: Artificial
<220> FEATURE:
<223> OTHER INFORMATION: aptamer

<400> SEQUENCE: 5
cauguaagcc acguagaacc ag                                                  22

<210> SEQ ID NO 6
<211> LENGTH: 40
<212> TYPE: RNA
<213> ORGANISM: Artificial
<220> FEATURE:
<223> OTHER INFORMATION: aptamer

<400> SEQUENCE: 6
ucccaugauu guucaggcac ggccuuucgg uucccucaau                               40

<210> SEQ ID NO 7
<211> LENGTH: 40
<212> TYPE: RNA
<213> ORGANISM: Artificial
<220> FEATURE:
<223> OTHER INFORMATION: aptamer

<400> SEQUENCE: 7
agucccuuga cacguccguu uucuaacugg aauagaggcc                               40

<210> SEQ ID NO 8
<211> LENGTH: 40
<212> TYPE: RNA
<213> ORGANISM: Artificial
<220> FEATURE:
<223> OTHER INFORMATION: aptamer

<400> SEQUENCE: 8
```
gggcugcacc ucuccgcuac guugucguug gaggcaccau                          40

<210> SEQ ID NO 9
<211> LENGTH: 40
<212> TYPE: RNA
<213> ORGANISM: Artificial
<220> FEATURE:
<223> OTHER INFORMATION: aptamer

<400> SEQUENCE: 9
gguauuaaaa cucccucgua ggucauccgc ccggccuagc                          40

<210> SEQ ID NO 10
<211> LENGTH: 40
<212> TYPE: RNA
<213> ORGANISM: Artificial
<220> FEATURE:
<223> OTHER INFORMATION: aptamer

<400> SEQUENCE: 10
cauccuuauc acauggucau ccgcccggcc augcaauguu                          40

<210> SEQ ID NO 11
<211> LENGTH: 40
<212> TYPE: RNA
<213> ORGANISM: Artificial
<220> FEATURE:
<223> OTHER INFORMATION: aptamer

<400> SEQUENCE: 11
cauucuaaau ucuaucaagg gucauccgcc cggcccgcau                          40

<210> SEQ ID NO 12
<211> LENGTH: 49
<212> TYPE: RNA
<213> ORGANISM: Artificial
<220> FEATURE:
<223> OTHER INFORMATION: aptamer

<400> SEQUENCE: 12
cauucuaaau ucuaucaagg gucauccgcc cggccgcgcu cgccaguca                49

<210> SEQ ID NO 13
<211> LENGTH: 40
<212> TYPE: RNA
<213> ORGANISM: Artificial
<220> FEATURE:
<223> OTHER INFORMATION: aptamer

<400> SEQUENCE: 13
uggcauccuu gcucacucca ggcuaaaccu cucgguuccc                          40

<210> SEQ ID NO 14
<211> LENGTH: 40
<212> TYPE: RNA
<213> ORGANISM: Artificial
<220> FEATURE:
<223> OTHER INFORMATION: aptamer

<400> SEQUENCE: 14
ccaagcacuu caucgucuag gcaauugccu cucgguaccc                          40

<210> SEQ ID NO 15
<211> LENGTH: 40
<212> TYPE: RNA

<213> ORGANISM: Artificial
<220> FEATURE:
<223> OTHER INFORMATION: aptamer

<400> SEQUENCE: 15
ccacaagcuc gcacuaguuc caggcuuccu cucgguaccc          40

<210> SEQ ID NO 16
<211> LENGTH: 40
<212> TYPE: RNA
<213> ORGANISM: Artificial
<220> FEATURE:
<223> OTHER INFORMATION: aptamer

<400> SEQUENCE: 16
cauguauuuc ugcacguucc agagaauccu cucgguaccc          40

<210> SEQ ID NO 17
<211> LENGTH: 40
<212> TYPE: RNA
<213> ORGANISM: Artificial
<220> FEATURE:
<223> OTHER INFORMATION: aptamer

<400> SEQUENCE: 17
uacacugcac gcuccgcuuu gaacaucaau ggaggcccug          40

<210> SEQ ID NO 18
<211> LENGTH: 40
<212> TYPE: RNA
<213> ORGANISM: Artificial
<220> FEATURE:
<223> OTHER INFORMATION: aptamer

<400> SEQUENCE: 18
gcgcucgcuc auagucaagg ugaaaacccc cauagagacu          40

<210> SEQ ID NO 19
<211> LENGTH: 29
<212> TYPE: RNA
<213> ORGANISM: Artificial
<220> FEATURE:
<223> OTHER INFORMATION: aptamer

<400> SEQUENCE: 19
uagucaaggu gaaaaccccc auagagacu          29

<210> SEQ ID NO 20
<211> LENGTH: 40
<212> TYPE: RNA
<213> ORGANISM: Artificial
<220> FEATURE:
<223> OTHER INFORMATION: aptamer

<400> SEQUENCE: 20
ggccugugcu aacaugaguc auccguccgg cucgcaacuc          40

<210> SEQ ID NO 21
<211> LENGTH: 40
<212> TYPE: RNA
<213> ORGANISM: Artificial
<220> FEATURE:
<223> OTHER INFORMATION: aptamer

<400> SEQUENCE: 21
ccuagcacgu ccguuucugg aucugucagu uagaggccua          40

<210> SEQ ID NO 22
<211> LENGTH: 40
<212> TYPE: RNA
<213> ORGANISM: Artificial
<220> FEATURE:
<223> OTHER INFORMATION: aptamer

<400> SEQUENCE: 22
gcaucaaccu cuguaagagc gcgcuuugcu ucaccaaaaa         40

<210> SEQ ID NO 23
<211> LENGTH: 40
<212> TYPE: RNA
<213> ORGANISM: Artificial
<220> FEATURE:
<223> OTHER INFORMATION: aptamer

<400> SEQUENCE: 23
acgguccuua aaaucuuccu uaaccacgcc caggaucuua         40

<210> SEQ ID NO 24
<211> LENGTH: 40
<212> TYPE: RNA
<213> ORGANISM: Artificial
<220> FEATURE:
<223> OTHER INFORMATION: aptamer

<400> SEQUENCE: 24
auucaccuca gcauguccgc uugugacgau ggaggcaccu         40

<210> SEQ ID NO 25
<211> LENGTH: 40
<212> TYPE: RNA
<213> ORGANISM: Artificial
<220> FEATURE:
<223> OTHER INFORMATION: aptamer

<400> SEQUENCE: 25
gguccuuaaa aucuuccaau cuaaacgauc cagacacggc         40

<210> SEQ ID NO 26
<211> LENGTH: 40
<212> TYPE: RNA
<213> ORGANISM: Artificial
<220> FEATURE:
<223> OTHER INFORMATION: aptamer

<400> SEQUENCE: 26
aaaaacuacu gccgaaccgu aagacacgua gaaccaggca         40

<210> SEQ ID NO 27
<211> LENGTH: 40
<212> TYPE: RNA
<213> ORGANISM: Artificial
<220> FEATURE:
<223> OTHER INFORMATION: aptamer

<400> SEQUENCE: 27
gaccagguuc cugacaucuc ugaacuauac cuccaaaacg         40

<210> SEQ ID NO 28
<211> LENGTH: 40
<212> TYPE: RNA
<213> ORGANISM: Artificial
<220> FEATURE:

```
<223> OTHER INFORMATION: aptamer

<400> SEQUENCE: 28
caucugaauu uaagccacgu agaaccaggc ccuccacgcg                              40

<210> SEQ ID NO 29
<211> LENGTH: 40
<212> TYPE: RNA
<213> ORGANISM: Artificial
<220> FEATURE:
<223> OTHER INFORMATION: aptamer

<400> SEQUENCE: 29
uaauacgacu cacuauaggg acgcucacgu acgcucagug                              40

<210> SEQ ID NO 30
<211> LENGTH: 40
<212> TYPE: RNA
<213> ORGANISM: Artificial
<220> FEATURE:
<223> OTHER INFORMATION: aptamer

<400> SEQUENCE: 30
aaugagggcc cacuuccgga ucuuugguuu gcuuccuugc                              40

<210> SEQ ID NO 31
<211> LENGTH: 40
<212> TYPE: RNA
<213> ORGANISM: Artificial
<220> FEATURE:
<223> OTHER INFORMATION: aptamer

<400> SEQUENCE: 31
ucgcuuaugg augcccacuu ccacucacug uccugcgcaa                              40

<210> SEQ ID NO 32
<211> LENGTH: 40
<212> TYPE: RNA
<213> ORGANISM: Artificial
<220> FEATURE:
<223> OTHER INFORMATION: aptamer

<400> SEQUENCE: 32
uauuaauacc ucagcccucu ucucuuaguc uggugccgau                              40

<210> SEQ ID NO 33
<211> LENGTH: 40
<212> TYPE: RNA
<213> ORGANISM: Artificial
<220> FEATURE:
<223> OTHER INFORMATION: aptamer

<400> SEQUENCE: 33
ucucuuuucg aauuccguuc uggcucacuc cuuggguauu                              40

<210> SEQ ID NO 34
<211> LENGTH: 40
<212> TYPE: RNA
<213> ORGANISM: Artificial
<220> FEATURE:
<223> OTHER INFORMATION: aptamer

<400> SEQUENCE: 34
cugacaucuu uuacacugau uucguuggc ccacuucugu                               40
```

```
<210> SEQ ID NO 35
<211> LENGTH: 40
<212> TYPE: RNA
<213> ORGANISM: Artificial
<220> FEATURE:
<223> OTHER INFORMATION: aptamer

<400> SEQUENCE: 35
gaguacagua agacacguag caccagucug acguuugucg                              40

<210> SEQ ID NO 36
<211> LENGTH: 40
<212> TYPE: RNA
<213> ORGANISM: Artificial
<220> FEATURE:
<223> OTHER INFORMATION: aptamer

<400> SEQUENCE: 36
ugccaucacc auguaagcca cguagaacca gcacuacuag                              40

<210> SEQ ID NO 37
<211> LENGTH: 40
<212> TYPE: RNA
<213> ORGANISM: Artificial
<220> FEATURE:
<223> OTHER INFORMATION: aptamer

<400> SEQUENCE: 37
ugagucuuau agccguccgu uuacguuugu cuagaggcca                              40

<210> SEQ ID NO 38
<211> LENGTH: 40
<212> TYPE: RNA
<213> ORGANISM: Artificial
<220> FEATURE:
<223> OTHER INFORMATION: aptamer

<400> SEQUENCE: 38
gcuucuugca uuguccgcuu aguuucuaug gaggcauagu                              40

<210> SEQ ID NO 39
<211> LENGTH: 40
<212> TYPE: RNA
<213> ORGANISM: Artificial
<220> FEATURE:
<223> OTHER INFORMATION: aptamer

<400> SEQUENCE: 39
ccgaauauuu uugcaccguc cgauugccau gcauugaggc                              40

<210> SEQ ID NO 40
<211> LENGTH: 40
<212> TYPE: RNA
<213> ORGANISM: Artificial
<220> FEATURE:
<223> OTHER INFORMATION: aptamer

<400> SEQUENCE: 40
ugauauuuaa auuuggccgc guuuaaaaca uccccuacga                              40

<210> SEQ ID NO 41
<211> LENGTH: 40
<212> TYPE: RNA
<213> ORGANISM: Artificial
<220> FEATURE:
<223> OTHER INFORMATION: aptamer
```

```
<400> SEQUENCE: 41
gauuccguug cccuuccguu gaacugugcc aggcuuuuug                        40

<210> SEQ ID NO 42
<211> LENGTH: 40
<212> TYPE: RNA
<213> ORGANISM: Artificial
<220> FEATURE:
<223> OTHER INFORMATION: aptamer

<400> SEQUENCE: 42
accuuugccg caucucaccc acgucuuguc aggccguuuc                        40

<210> SEQ ID NO 43
<211> LENGTH: 20
<212> TYPE: RNA
<213> ORGANISM: Artificial
<220> FEATURE:
<223> OTHER INFORMATION: aptamer

<400> SEQUENCE: 43
gggacgcuca cguacgcuca                                              20

<210> SEQ ID NO 44
<211> LENGTH: 20
<212> TYPE: RNA
<213> ORGANISM: Artificial
<220> FEATURE:
<223> OTHER INFORMATION: aptamer

<400> SEQUENCE: 44
ucagugccug gacgugcagu                                              20

<210> SEQ ID NO 45
<211> LENGTH: 80
<212> TYPE: RNA
<213> ORGANISM: Artificial
<220> FEATURE:
<223> OTHER INFORMATION: aptamer

<400> SEQUENCE: 45
gggacgcuca cguacgcuca ucccaugauu guucaggcac ggccuuucgg uucccucaau   60
ucagugccug gacgugcagu                                              80

<210> SEQ ID NO 46
<211> LENGTH: 80
<212> TYPE: RNA
<213> ORGANISM: Artificial
<220> FEATURE:
<223> OTHER INFORMATION: aptamer

<400> SEQUENCE: 46
gggacgcuca cguacgcuca agucccuuga cacguccguu uucuaacugg aauagaggcc   60
ucagugccug gacgugcagu                                              80

<210> SEQ ID NO 47
<211> LENGTH: 80
<212> TYPE: RNA
<213> ORGANISM: Artificial
<220> FEATURE:
<223> OTHER INFORMATION: aptamer

<400> SEQUENCE: 47
gggacgcuca cguacgcuca gggcugcacc ucuccgcuac guugucguug gaggcaccau   60
```

```
ucagugccug gacgugcagu                                              80

<210> SEQ ID NO 48
<211> LENGTH: 80
<212> TYPE: RNA
<213> ORGANISM: Artificial
<220> FEATURE:
<223> OTHER INFORMATION: aptamer

<400> SEQUENCE: 48
gggacgcuca cguacgcuca gguauuaaaa cucccucgua ggucauccgc ccggccuagc   60
ucagugccug gacgugcagu                                              80

<210> SEQ ID NO 49
<211> LENGTH: 80
<212> TYPE: RNA
<213> ORGANISM: Artificial
<220> FEATURE:
<223> OTHER INFORMATION: aptamer

<400> SEQUENCE: 49
gggacgcuca cguacgcuca cauccuuauc acauggucau ccgcccggcc augcaauguu   60
ucagugccug gacgugcagu                                              80

<210> SEQ ID NO 50
<211> LENGTH: 80
<212> TYPE: RNA
<213> ORGANISM: Artificial
<220> FEATURE:
<223> OTHER INFORMATION: aptamer

<400> SEQUENCE: 50
gggacgcuca cguacgcuca cauucuaaau ucuaucaagg gucauccgcc cggcccgcau   60
ucagugccug gacgugcagu                                              80

<210> SEQ ID NO 51
<211> LENGTH: 89
<212> TYPE: RNA
<213> ORGANISM: Artificial
<220> FEATURE:
<223> OTHER INFORMATION: aptamer

<400> SEQUENCE: 51
gggacgcuca cguacgcuca cauucuaaau ucuaucaagg gucauccgcc cggccgcgcu   60
cgccagucau cagugccugg acgugcagu                                    89

<210> SEQ ID NO 52
<211> LENGTH: 80
<212> TYPE: RNA
<213> ORGANISM: Artificial
<220> FEATURE:
<223> OTHER INFORMATION: aptamer

<400> SEQUENCE: 52
gggacgcuca cguacgcuca uggcauccuu gcucacucca ggcuaaaccu cucgguuccc   60
ucagugccug gacgugcagu                                              80

<210> SEQ ID NO 53
<211> LENGTH: 80
<212> TYPE: RNA
<213> ORGANISM: Artificial
<220> FEATURE:
```

<223> OTHER INFORMATION: aptamer

<400> SEQUENCE: 53
gggacgcuca cguacgcuca ccaagcacuu caucgucuag gcaauugccu cucgguaccc    60
ucagugccug gacgugcagu    80

<210> SEQ ID NO 54
<211> LENGTH: 80
<212> TYPE: RNA
<213> ORGANISM: Artificial
<220> FEATURE:
<223> OTHER INFORMATION: aptamer

<400> SEQUENCE: 54
gggacgcuca cguacgcuca ccacaagcuc gcacuaguuc caggcuuccu cucgguaccc    60
ucagugccug gacgugcagu    80

<210> SEQ ID NO 55
<211> LENGTH: 80
<212> TYPE: RNA
<213> ORGANISM: Artificial
<220> FEATURE:
<223> OTHER INFORMATION: aptamer

<400> SEQUENCE: 55
gggacgcuca cguacgcuca cauguauuuc ugcacguucc agagaauccu cucgguaccc    60
ucagugccug gacgugcagu    80

<210> SEQ ID NO 56
<211> LENGTH: 80
<212> TYPE: RNA
<213> ORGANISM: Artificial
<220> FEATURE:
<223> OTHER INFORMATION: aptamer

<400> SEQUENCE: 56
gggacgcuca cguacgcuca uacacugcac gcuccgcuuu gaacaucaau ggaggcccug    60
ucagugccug gacgugcagu    80

<210> SEQ ID NO 57
<211> LENGTH: 80
<212> TYPE: RNA
<213> ORGANISM: Artificial
<220> FEATURE:
<223> OTHER INFORMATION: aptamer

<400> SEQUENCE: 57
gggacgcuca cguacgcuca gcgcucgcuc auagucaagg ugaaaacccc cauagagacu    60
ucagugccug gacgugcagu    80

<210> SEQ ID NO 58
<211> LENGTH: 69
<212> TYPE: RNA
<213> ORGANISM: Artificial
<220> FEATURE:
<223> OTHER INFORMATION: aptamer

<400> SEQUENCE: 58
gggacgcuca cguacgcuca uagucaaggu gaaaacccc auagagacuu cagugccugg    60
acgugcagu    69

```
<210> SEQ ID NO 59
<211> LENGTH: 80
<212> TYPE: RNA
<213> ORGANISM: Artificial
<220> FEATURE:
<223> OTHER INFORMATION: aptamer

<400> SEQUENCE: 59
gggacgcuca cguacgcuca ggccugugcu aacaugaguc auccguccgg cucgcaacuc    60
ucagugccug gacgugcagu                                                80

<210> SEQ ID NO 60
<211> LENGTH: 80
<212> TYPE: RNA
<213> ORGANISM: Artificial
<220> FEATURE:
<223> OTHER INFORMATION: aptamer

<400> SEQUENCE: 60
gggacgcuca cguacgcuca ccuagcacgu ccguuucugg aucugucagu uagaggccua    60
ucagugccug gacgugcagu                                                80

<210> SEQ ID NO 61
<211> LENGTH: 80
<212> TYPE: RNA
<213> ORGANISM: Artificial
<220> FEATURE:
<223> OTHER INFORMATION: aptamer

<400> SEQUENCE: 61
gggacgcuca cguacgcuca gcaucaaccu cuguaagagc gcgcuuugcu ucaccaaaaa    60
ucagugccug gacgugcagu                                                80

<210> SEQ ID NO 62
<211> LENGTH: 80
<212> TYPE: RNA
<213> ORGANISM: Artificial
<220> FEATURE:
<223> OTHER INFORMATION: aptamer

<400> SEQUENCE: 62
gggacgcuca cguacgcuca acgguccuua aaaucuuccu uaaccacgcc caggaucuua    60
ucagugccug gacgugcagu                                                80

<210> SEQ ID NO 63
<211> LENGTH: 80
<212> TYPE: RNA
<213> ORGANISM: Artificial
<220> FEATURE:
<223> OTHER INFORMATION: aptamer

<400> SEQUENCE: 63
gggacgcuca cguacgcuca auucaccuca gcauguccgc uugugacgau ggaggcaccu    60
ucagugccug gacgugcagu                                                80

<210> SEQ ID NO 64
<211> LENGTH: 80
<212> TYPE: RNA
<213> ORGANISM: Artificial
<220> FEATURE:
<223> OTHER INFORMATION: aptamer

<400> SEQUENCE: 64
```

```
gggacgcuca cguacgcuca gguccuuaaa aucuuccaau cuaaacgauc cagacacggc    60
ucagugccug gacgugcagu                                                80

<210> SEQ ID NO 65
<211> LENGTH: 80
<212> TYPE: RNA
<213> ORGANISM: Artificial
<220> FEATURE:
<223> OTHER INFORMATION: aptamer

<400> SEQUENCE: 65
gggacgcuca cguacgcuca aaaaacuacu gccgaaccgu aagacacgua gaaccaggca    60
ucagugccug gacgugcagu                                                80

<210> SEQ ID NO 66
<211> LENGTH: 80
<212> TYPE: RNA
<213> ORGANISM: Artificial
<220> FEATURE:
<223> OTHER INFORMATION: aptamer

<400> SEQUENCE: 66
gggacgcuca cguacgcuca gaccagguuc cugacaucuc ugaacuauac cuccaaaacg    60
ucagugccug gacgugcagu                                                80

<210> SEQ ID NO 67
<211> LENGTH: 80
<212> TYPE: RNA
<213> ORGANISM: Artificial
<220> FEATURE:
<223> OTHER INFORMATION: aptamer

<400> SEQUENCE: 67
gggacgcuca cguacgcuca caucugaauu uaagccacgu agaaccaggc ccuccacgcg    60
ucagugccug gacgugcagu                                                80

<210> SEQ ID NO 68
<211> LENGTH: 74
<212> TYPE: RNA
<213> ORGANISM: Artificial
<220> FEATURE:
<223> OTHER INFORMATION: aptamer

<400> SEQUENCE: 68
gggacgcuca cguacgcuca uaauacgacu cacuauaggg acgcucacgu acgcucagug    60
ccuggacgug cagu                                                      74

<210> SEQ ID NO 69
<211> LENGTH: 80
<212> TYPE: RNA
<213> ORGANISM: Artificial
<220> FEATURE:
<223> OTHER INFORMATION: aptamer

<400> SEQUENCE: 69
gggacgcuca cguacgcuca aaugagggcc cacuuccgga ucuuugguuu gcuuccuugc    60
ucagugccug gacgugcagu                                                80

<210> SEQ ID NO 70
<211> LENGTH: 80
<212> TYPE: RNA
<213> ORGANISM: Artificial
```

```
<220> FEATURE:
<223> OTHER INFORMATION: aptamer

<400> SEQUENCE: 70
gggacgcuca cguacgcuca ucgcuuaugg augcccacuu ccacucacug uccugcgcaa      60
ucagugccug gacgugcagu                                                  80

<210> SEQ ID NO 71
<211> LENGTH: 80
<212> TYPE: RNA
<213> ORGANISM: Artificial
<220> FEATURE:
<223> OTHER INFORMATION: aptamer

<400> SEQUENCE: 71
gggacgcuca cguacgcuca uauuaauacc ucagcccucu ucucuuaguc uggugccgau      60
ucagugccug gacgugcagu                                                  80

<210> SEQ ID NO 72
<211> LENGTH: 80
<212> TYPE: RNA
<213> ORGANISM: Artificial
<220> FEATURE:
<223> OTHER INFORMATION: aptamer

<400> SEQUENCE: 72
gggacgcuca cguacgcuca ucucuuuucg aauccguuc uggcucacuc cuugggu auu      60 ucagugccug gacgugcagu                                                  80

<210> SEQ ID NO 73
<211> LENGTH: 80
<212> TYPE: RNA
<213> ORGANISM: Artificial
<220> FEATURE:
<223> OTHER INFORMATION: aptamer

<400> SEQUENCE: 73
gggacgcuca cguacgcuca cugacaucuu uuacacugau uucguuggc ccacuucugu       60 ucagugccug gacgugcagu                                                  80

<210> SEQ ID NO 74
<211> LENGTH: 80
<212> TYPE: RNA
<213> ORGANISM: Artificial
<220> FEATURE:
<223> OTHER INFORMATION: aptamer

<400> SEQUENCE: 74
gggacgcuca cguacgcuca gaguacagua agacacguag caccagucug acguuugucg      60
ucagugccug gacgugcagu                                                  80

<210> SEQ ID NO 75
<211> LENGTH: 80
<212> TYPE: RNA
<213> ORGANISM: Artificial
<220> FEATURE:
<223> OTHER INFORMATION: aptamer

<400> SEQUENCE: 75
gggacgcuca cguacgcuca ugccaucacc auguaagcca cguagaacca gcacuacuag      60
ucagugccug gacgugcagu                                                  80
```

```
<210> SEQ ID NO 76
<211> LENGTH: 80
<212> TYPE: RNA
<213> ORGANISM: Artificial
<220> FEATURE:
<223> OTHER INFORMATION: aptamer

<400> SEQUENCE: 76
gggacgcuca cguacgcuca ugagucuuau agccguccgu uuacguuugu cuagaggcca      60
ucagugccug gacgugcagu                                                 80

<210> SEQ ID NO 77
<211> LENGTH: 80
<212> TYPE: RNA
<213> ORGANISM: Artificial
<220> FEATURE:
<223> OTHER INFORMATION: aptamer

<400> SEQUENCE: 77
gggacgcuca cguacgcuca gcuucuugca uuguccgcuu aguuucuaug gaggcauagu      60
ucagugccug gacgugcagu                                                 80

<210> SEQ ID NO 78
<211> LENGTH: 80
<212> TYPE: RNA
<213> ORGANISM: Artificial
<220> FEATURE:
<223> OTHER INFORMATION: aptamer

<400> SEQUENCE: 78
gggacgcuca cguacgcuca ccgaauauuu uugcaccguc cgauugccau gcauugaggc      60
ucagugccug gacgugcagu                                                 80

<210> SEQ ID NO 79
<211> LENGTH: 80
<212> TYPE: RNA
<213> ORGANISM: Artificial
<220> FEATURE:
<223> OTHER INFORMATION: aptamer

<400> SEQUENCE: 79
gggacgcuca cguacgcuca ugauauuuaa auuuggccgc guuuaaaaca uccccuacga      60
ucagugccug gacgugcagu                                                 80

<210> SEQ ID NO 80
<211> LENGTH: 80
<212> TYPE: RNA
<213> ORGANISM: Artificial
<220> FEATURE:
<223> OTHER INFORMATION: aptamer

<400> SEQUENCE: 80
gggacgcuca cguacgcuca gauuccguug cccuuccguu gaacugugcc aggcuuuuug      60
ucagugccug gacgugcagu                                                 80

<210> SEQ ID NO 81
<211> LENGTH: 80
<212> TYPE: RNA
<213> ORGANISM: Artificial
<220> FEATURE:
<223> OTHER INFORMATION: aptamer

<400> SEQUENCE: 81
```

```
gggacgcuca cguacgcuca accuuugccg caucucaccc acgucuuguc aggccguuuc    60
ucagugccug gacgugcagu                                                80

<210> SEQ ID NO 82
<211> LENGTH: 80
<212> TYPE: RNA
<213> ORGANISM: Artificial
<220> FEATURE:
<223> OTHER INFORMATION: control RNA
<220> FEATURE:
<221> NAME/KEY: misc_feature
<222> LOCATION: (21)..(60)
<223> OTHER INFORMATION: n stands for any base

<400> SEQUENCE: 82
gggacgcuca cguacgcuca nnnnnnnnnn nnnnnnnnnn nnnnnnnnnn nnnnnnnnnn    60
ucagugccug gacgugcagu                                                80

<210> SEQ ID NO 83
<211> LENGTH: 79
<212> TYPE: RNA
<213> ORGANISM: Artificial
<220> FEATURE:
<223> OTHER INFORMATION: aptamer

<400> SEQUENCE: 83
gggacgcuca cguacgcuca gaguacagua agacacguag caccagucug acguuugucg    60
ucagugccug gacgugcag                                                 79

<210> SEQ ID NO 84
<211> LENGTH: 77
<212> TYPE: RNA
<213> ORGANISM: Artificial
<220> FEATURE:
<223> OTHER INFORMATION: aptamer

<400> SEQUENCE: 84
gggacgcuca cguacgcuca gaguacagua agacacguag caccagucug acguuugucg    60
ucagugccug gacgugc                                                   77

<210> SEQ ID NO 85
<211> LENGTH: 76
<212> TYPE: RNA
<213> ORGANISM: Artificial
<220> FEATURE:
<223> OTHER INFORMATION: aptamer

<400> SEQUENCE: 85
gggacgcuca cguacgcuca gaguacagua agacacguag caccagucug acguuugucg    60
ucagugccug gacgug                                                    76

<210> SEQ ID NO 86
<211> LENGTH: 65
<212> TYPE: RNA
<213> ORGANISM: Artificial
<220> FEATURE:
<223> OTHER INFORMATION: aptamer

<400> SEQUENCE: 86
gggcagagua caguaagaca cguagcacca gucugacguu ugucgucagu gccuggacgu    60
gcagu                                                                65
```

```
<210> SEQ ID NO 87
<211> LENGTH: 62
<212> TYPE: RNA
<213> ORGANISM: Artificial
<220> FEATURE:
<223> OTHER INFORMATION: aptamer

<400> SEQUENCE: 87
gggaguacag uaagacacgu agcaccaguc ugacguuugu cgucagugcc uggacgugca      60
gu                                                                    62

<210> SEQ ID NO 88
<211> LENGTH: 60
<212> TYPE: RNA
<213> ORGANISM: Artificial
<220> FEATURE:
<223> OTHER INFORMATION: aptamer

<400> SEQUENCE: 88
ggguacagua agacacguag caccagucug acguuugucg ucagugccug gacgugcagu      60

<210> SEQ ID NO 89
<211> LENGTH: 59
<212> TYPE: RNA
<213> ORGANISM: Artificial
<220> FEATURE:
<223> OTHER INFORMATION: aptamer

<400> SEQUENCE: 89
gggacaguaa gacacguagc accagucuga cguuugucgu cagugccugg acgugcagu       59

<210> SEQ ID NO 90
<211> LENGTH: 55
<212> TYPE: RNA
<213> ORGANISM: Artificial
<220> FEATURE:
<223> OTHER INFORMATION: aptamer

<400> SEQUENCE: 90
ggguaagaca cguagcacca gucugacguu ugucgucagu gccuggacgu gcagu           55

<210> SEQ ID NO 91
<211> LENGTH: 50
<212> TYPE: RNA
<213> ORGANISM: Artificial
<220> FEATURE:
<223> OTHER INFORMATION: aptamer

<400> SEQUENCE: 91
gggcacguag caccagucug acguuugucg ucagugccug gacgugcagu                 50

<210> SEQ ID NO 92
<211> LENGTH: 46
<212> TYPE: RNA
<213> ORGANISM: Artificial
<220> FEATURE:
<223> OTHER INFORMATION: aptamer

<400> SEQUENCE: 92
ggguagcacc agucugacgu uugucgucag ugccuggacg ugcacc                     46

<210> SEQ ID NO 93
<211> LENGTH: 58
<212> TYPE: RNA
<213> ORGANISM: Artificial
```

```
<220> FEATURE:
<223> OTHER INFORMATION: aptamer

<400> SEQUENCE: 93
gggaguacag uaagacacgu agcaccaguc gcguuugucg cgugccugga cgugcagu        58

<210> SEQ ID NO 94
<211> LENGTH: 54
<212> TYPE: RNA
<213> ORGANISM: Artificial
<220> FEATURE:
<223> OTHER INFORMATION: aptamer

<400> SEQUENCE: 94
gggaguacag uaagacacgu agcaccaguc guuugucgug ccuggacgug cagu            54

<210> SEQ ID NO 95
<211> LENGTH: 46
<212> TYPE: RNA
<213> ORGANISM: Artificial
<220> FEATURE:
<223> OTHER INFORMATION: aptamer

<400> SEQUENCE: 95
gggaguacag uaagacacgu agcaccagug ugccuggacg ugcagu                     46

<210> SEQ ID NO 96
<211> LENGTH: 43
<212> TYPE: RNA
<213> ORGANISM: Artificial
<220> FEATURE:
<223> OTHER INFORMATION: aptamer

<400> SEQUENCE: 96
gggacaguaa gacacguagc accagugugc cuggacgugc agu                        43

<210> SEQ ID NO 97
<211> LENGTH: 42
<212> TYPE: RNA
<213> ORGANISM: Artificial
<220> FEATURE:
<223> OTHER INFORMATION: aptamer

<400> SEQUENCE: 97
gggcaguaag acacguagca ccagugugcc uggacgugca gu                         42

<210> SEQ ID NO 98
<211> LENGTH: 41
<212> TYPE: RNA
<213> ORGANISM: Artificial
<220> FEATURE:
<223> OTHER INFORMATION: aptamer

<400> SEQUENCE: 98
gggaguaaga cacguagcac cagugugccu ggacgugcag u                          41

<210> SEQ ID NO 99
<211> LENGTH: 40
<212> TYPE: RNA
<213> ORGANISM: Artificial
<220> FEATURE:
<223> OTHER INFORMATION: aptamer

<400> SEQUENCE: 99
gggguaagac acguagcacc agugugccug gacgugcagu                            40
```

```
<210> SEQ ID NO 100
<211> LENGTH: 39
<212> TYPE: RNA
<213> ORGANISM: Artificial
<220> FEATURE:
<223> OTHER INFORMATION: aptamer

<400> SEQUENCE: 100
ggguaagaca cguagcacca gugugccugg acgugcagu                              39

<210> SEQ ID NO 101
<211> LENGTH: 38
<212> TYPE: RNA
<213> ORGANISM: Artificial
<220> FEATURE:
<223> OTHER INFORMATION: aptamer

<400> SEQUENCE: 101
gggaagacac guagcaccag ugugccugga cgugcagu                               38

<210> SEQ ID NO 102
<211> LENGTH: 37
<212> TYPE: RNA
<213> ORGANISM: Artificial
<220> FEATURE:
<223> OTHER INFORMATION: aptamer

<400> SEQUENCE: 102
gggagacacg uagcaccagu gugccuggac gugcagu                                37

<210> SEQ ID NO 103
<211> LENGTH: 38
<212> TYPE: RNA
<213> ORGANISM: Artificial
<220> FEATURE:
<223> OTHER INFORMATION: aptamer

<400> SEQUENCE: 103
ggguaagcac guagcaccag ugugccugga cgugcagu                               38

<210> SEQ ID NO 104
<211> LENGTH: 37
<212> TYPE: RNA
<213> ORGANISM: Artificial
<220> FEATURE:
<223> OTHER INFORMATION: aptamer

<400> SEQUENCE: 104
ggguaagaca cguagcaccg ugugccggac gugcagu                                37

<210> SEQ ID NO 105
<211> LENGTH: 38
<212> TYPE: RNA
<213> ORGANISM: Artificial
<220> FEATURE:
<223> OTHER INFORMATION: aptamer

<400> SEQUENCE: 105
ggguaagaca cguagcacca gugugccugg acgugcgu                               38

<210> SEQ ID NO 106
<211> LENGTH: 38
<212> TYPE: RNA
<213> ORGANISM: Artificial
<220> FEATURE:
<223> OTHER INFORMATION: aptamer
```

```
<400> SEQUENCE: 106
ggguaagaca cguagaccag ugugccugga cgugcagu                                38

<210> SEQ ID NO 107
<211> LENGTH: 38
<212> TYPE: RNA
<213> ORGANISM: Artificial
<220> FEATURE:
<223> OTHER INFORMATION: aptamer

<400> SEQUENCE: 107
ggguaagaca cguagcacca gugugccugg agugcagu                                38

<210> SEQ ID NO 108
<211> LENGTH: 41
<212> TYPE: RNA
<213> ORGANISM: Artificial
<220> FEATURE:
<223> OTHER INFORMATION: aptamer

<400> SEQUENCE: 108
gggacaguaa gacacguagc accagugccu ggacgugcag u                            41

<210> SEQ ID NO 109
<211> LENGTH: 40
<212> TYPE: RNA
<213> ORGANISM: Artificial
<220> FEATURE:
<223> OTHER INFORMATION: aptamer

<400> SEQUENCE: 109
gggcaguaag acacguagca ccagugccug gacgugcagu                              40

<210> SEQ ID NO 110
<211> LENGTH: 39
<212> TYPE: RNA
<213> ORGANISM: Artificial
<220> FEATURE:
<223> OTHER INFORMATION: aptamer

<400> SEQUENCE: 110
gggaguaaga cacguagcac cagugccugg acgugcagu                               39

<210> SEQ ID NO 111
<211> LENGTH: 38
<212> TYPE: RNA
<213> ORGANISM: Artificial
<220> FEATURE:
<223> OTHER INFORMATION: aptamer

<400> SEQUENCE: 111
gggguaagac acguagcacc agugccugga cgugcagu                                38

<210> SEQ ID NO 112
<211> LENGTH: 37
<212> TYPE: RNA
<213> ORGANISM: Artificial
<220> FEATURE:
<223> OTHER INFORMATION: aptamer

<400> SEQUENCE: 112
ggguaagaca cguagcacca gugccuggac gugcagu                                 37

<210> SEQ ID NO 113
```

```
<211> LENGTH: 37
<212> TYPE: RNA
<213> ORGANISM: Artificial
<220> FEATURE:
<223> OTHER INFORMATION: aptamer

<400> SEQUENCE: 113
ggguaagaca cguagaacca gugacuggaa gugcagu                              37

<210> SEQ ID NO 114
<211> LENGTH: 18
<212> TYPE: RNA
<213> ORGANISM: Artificial
<220> FEATURE:
<223> OTHER INFORMATION: aptamer
<220> FEATURE:
<221> NAME/KEY: misc_feature
<222> LOCATION: (5)..(17)
<223> OTHER INFORMATION: n stands for any base

<400> SEQUENCE: 114
uaagncacgu agnaccng                                                   18

<210> SEQ ID NO 115
<211> LENGTH: 17
<212> TYPE: RNA
<213> ORGANISM: Artificial
<220> FEATURE:
<223> OTHER INFORMATION: aptamer

<400> SEQUENCE: 115
acgcucacgu acgcuca                                                    17
```